United States Patent
Thastrup et al.

(10) Patent No.: US 9,150,899 B2
(45) Date of Patent: Oct. 6, 2015

(54) IDENTIFICATION OF COMPOUNDS MODIFYING A CELLULAR RESPONSE

(75) Inventors: Ole Thastrup, Birkerod (DK); Morten Meldal, Copenhagen Nv (DK); Grith Hagel, Dragor (DK); Jens Chr. Norrild, Birkerod (DK); Morten Hentzer, Holbæk (DK)

(73) Assignee: 2cureX, Birkerod (DK)

( * ) Notice: Subject to any disclaimer, the term of this patent is extended or adjusted under 35 U.S.C. 154(b) by 405 days.

(21) Appl. No.: 13/441,091

(22) Filed: Apr. 6, 2012

(65) Prior Publication Data

US 2013/0123140 A1    May 16, 2013

Related U.S. Application Data

(63) Continuation of application No. 11/569,597, filed as application No. PCT/DK2005/000347 on May 25, 2005, now abandoned.

(30) Foreign Application Priority Data

May 25, 2004  (DK) ................................ 2004 00821
May 25, 2004  (DK) ................................ 2004 00822

(51) Int. Cl.
   C40B 30/06    (2006.01)
   C12Q 1/02     (2006.01)
   C07K 1/04     (2006.01)
   C07K 5/103    (2006.01)
   (Continued)

(52) U.S. Cl.
   CPC .............. *C12Q 1/025* (2013.01); *C07K 1/047* (2013.01); *C07K 5/1008* (2013.01); *C07K 7/06* (2013.01); *C07K 7/08* (2013.01); *G01N 33/5023* (2013.01); *G01N 33/54313* (2013.01); *G01N 33/6845* (2013.01); *C40B 30/06* (2013.01); *G01N 2035/00158* (2013.01); *G01N 2500/10* (2013.01)

(58) Field of Classification Search
   None
   See application file for complete search history.

(56) References Cited

U.S. PATENT DOCUMENTS 4,266,032 A    5/1981   Miller et al.
4,293,654 A    10/1981  Levine et al.
(Continued)

FOREIGN PATENT DOCUMENTS

WO    WO-2003/038431    5/2003
WO    WO-2005/045430    5/2005

OTHER PUBLICATIONS

A. Borchardt et al., Small Molecule-Dependent Genetic Selection in Stochastic Nanodroplet as a Means of Detecting Protein-Ligand Interactions on a Large Scale; *Chemistry and Biology*; 4:961; Dec. 1997.

(Continued)

*Primary Examiner* — Christian Boesen
(74) *Attorney, Agent, or Firm* — Gifford, Krass, Sprinkle, Anderson & Citkowski, P.C.

(57) ABSTRACT

The present invention relates to methods for identifying compounds capable of modulating a cellular response. The methods involve attaching living cells to solid supports comprising a library of test compounds. The test compounds are linked to the solid support via cleavable linkers and may thus be released from the solid supports. Solid supports comprising cells, wherein the cellular response of interest has been modulated are selected and the test compound of the solid support can then be identified. The cellular response may for example be changes in complex formation between proteins.

7 Claims, 10 Drawing Sheets

(51) Int. Cl.

| | |
|---|---|
| *C07K 7/06* | (2006.01) |
| *C07K 7/08* | (2006.01) |
| *G01N 33/50* | (2006.01) |
| *G01N 33/543* | (2006.01) |
| *G01N 33/68* | (2006.01) |
| *G01N 35/00* | (2006.01) |

(56) References Cited

U.S. PATENT DOCUMENTS

| | | | |
|---|---|---|---|
| 5,436,128 | A | 7/1995 | Harpold et al. |
| 5,510,240 | A | 4/1996 | Lam et al. |
| 6,670,142 | B2 | 12/2003 | Lau et al. |
| 2002/0155507 | A1 | 10/2002 | Bruchez et al. |
| 2003/0059764 | A1 | 3/2003 | Ravkin et al. |
| 2004/0096906 | A1 | 5/2004 | Lam et al. |
| 2005/0153321 | A1 | 7/2005 | Saba |

OTHER PUBLICATIONS

P.M. Cardarelli et al., The Collagen Receptor , from MG-63 and HT1080 Cells, Interacts With a Cyclic RGD Peptide; *The Journal of Biological Chemistry*; 267(32): 23159-23164; Nov. 1992.

M.H.S. Cezari et al., Cathepsin B Carboxydipeptidase Specificity Analysis Using Internally Quenched Fluorescent Peptides; *Biochem. J.*; 368: 365-369; 2002.

R.E. Dolle, Comprehensive Survey of Combinatorial Library Synthesis; 2002; *Journal Combinatorial Chememistry*; 5: 693-753; 2003.

C.K. Jayawickreme et al., Generation of Multiuse Peptide Libraries for Functional Screenings, Humana Press, pp. 107-128; 1998.

C.K. Jayawickreme et al., Use of a Cell-Based, Lawn Format Assay to Rapidly Screen a 442,368 Bead-Based Peptide Library, *J. Pharmacol. Toxicol*; 42: 189-197; 1999.

W.A.S. Judice et al., Carboxydipeptidase Activities of Recombinant Cysteine Peptidases; *Eur. J. Biochem*; 271:1046-1053; 2004.

K.S. Lam et al,. A One-Bead One-Peptide Combinatorial Library Method for B-Cell Epitope Mapping; *Methods: A Companion to Methods in Enzymology*; 9: 482-493; 1996.

D.E. Lau et al., Identifying Peptide Ligands for Cell Surface Receptors Using Cell-Growth-On-Bead Assay and One-Bead One-Compound Combinatorial Library; *Biotechnology Letters*; 24: 497-500; 2002.

M. Meldal, Multiple Column Synthesis of Quenched Solid-Phase Bound Fluorgenic Substrates for Characterization of Endoprotease Specificity; *Methods: A Companion to Methods in Enzymology*; 6: 417-424; 1994.

M.E. Pennington et al., The Use of Combinatorial Library Method to Isolate Human Tumor Cell Adhesion Peptides; Molecular Diversity; 2: 19-28; 1996.

Chemical Abstracts Service, Columbus, OH, U.S. Accession No. 98:107766, May 12, 1984; Abstract of Damirov, A.G. et al., Fragmentary conformational analysis of the Arg6-Lys13 segment of the dynorphin molecule, Doklady—Akademiya Nauk Azerbaidzhanskoi SSR, 38(6): 53-7.

Merrifield, R. et al., Solid Phase Peptide Synthesis. I. The Synthesis of a Tetrapeptide, *Synthesis of a Tetrapeptide,* 85: 2149-54, Jul. 20, 1963.

Van Wezel, A., Growth of Cell-strains and Primary Cells on Microcarriers in Homogeneous Culture, *Nature,*16: 64-65, Oct. 7, 1967.

Amholt, K. et al., Changes in intracellular cAMP reported by a Redistribution assay using a cAMP-dependent protein kinase-green fluorescent protein chimer, *Cellular Signalling,* 16: 907-920, 2004.

Evans, B. et al., Identification of a Potent and Selective Oxytocin Antagonist, from Screening a Fully Encoded Differential Release Combinatorial Chemical Library, *Bioorganic & Medicinal Chemistry Letters,* 11: 1297-1300 (2001).

Harpur, A. et al., Imaging FRET between spectrally similar GFP molecules in single cells, *Nature Biotechnology,* 19: 167-9, Feb. 2001.

Lam, K. et al., Synthesis and Screening of "One-Bead One-Compound" Combinatorial Peptide Libraries, *Methods in Enzymology,* 369: 298-322, 2003.

Nagy, S. et al., Identification of Novel Ah Receptor Agonists Using a High-Throughput Green Fluorescent Protein-Based Recombinant Cell Bioassay, *Biochemistry,* 41: 861-8, 2002.

Park, S. et al., The use of one-bead one-compound combinatorial library method to identify peptide ligands for α4β1 integrin receptor in non-Hodgkin's lymphoma, *Letters in Peptide Science,* 8: 171-8, 2002.

Seluanov, A., DNA end joining becomes less efficient and more error-prone during cellular senescence, *PNAS*, 101(20): 7624-9, May 18, 2004.

Meldal, M., The One-Bead Two-Compound Assay for Solid Phase Screening of Combinatorial Libraries, *Biopolymers* (Peptide Science), 66: 93-100, 2002.

Fredriksson, S. et al., Protein detection using proximity-dependent DNA ligation assays, *Nature Biotechnology,* 20(5): 473-7, May 2002.

Mousses, S, et al., RNAi microarray analysis in cultured mammalian cells, *Genome Research*, 13(10): 2341-47, Oct. 2003.

Mousses, S, et al., RNAi microarray analysis in cultured mammalian cells, *Genome Research*, 13(10): 2341-47, Oct. 2003, supplemental information 1.

Mousses, S, et al., RNAi microarray analysis in cultured mammalian cells, *Genome Research*, 13(10): 2341-47, Oct. 2003, supplemental information 2.

Mousses, S, et al., RNAi microarray analysis in cultured mammalian cells, *Genome Research*, 13(10): 2341-47, Oct. 2003, supplemental information 3.

I)

II)

Structure
elucidation

Hits ready for structure
elucidation

I)

II)

Structure
elucidation

Hits ready for structure elucidation

A

Wang linker

B

Rink linker

C

HMBA linker

D

Rich photolabile linker

E

NBA-type photo linkers

F

Holmes photolabile linker

| | | | | | | | Difference | Calc. | |
|---|---|---|---|---|---|---|---|---|---|
| | | | | | | | | | |
| 440,2372 | | | | | | | −0,0177 | 440,2549 | |
| 309,1569 | 131,0803 | | | | | | −0,0143 | 131,0946 | |
| 281,1514 | 159,0858 | 28,0055 | | | | C6H13NO2 | −0,0037 | 159,0895 | 27,9949 |
| 182,0832 | 258,154 | 127,0737 | 99,0682 | | | CO | 0,0106 | 127,0759 | 99,0684 |
| 169,0765 | 271,1607 | 140,0804 | 112,0749 | 13,0067 | | C5H9NO | −0,0022 | 112,0762 | 13,0078 |
| 115,0546 | 325,1826 | 194,1023 | 166,0968 | 67,0286 | | CH | −0,0013 | 67,0422 | 54,0344 |
| | | | | 54,0219 | | C3H4N | −0,0136 | 115,0548 | |
| | | | | 115,0546 | | C9H7 | −0,0002 | | |

Several beads covered with cells: 5x objective

One bead covered with cells: 20x objective

IDENTIFICATION OF COMPOUNDS MODIFYING A CELLULAR RESPONSE

REFERENCE TO RELATED APPLICATIONS

This application is a continuation of U.S. patent application Ser. No. 11/569,597, filed Nov. 27, 2006, which is the U.S. national stage application of PCT/DK2005/000347, filed May 25, 2005, which claims priority to Denmark application Nos. PA200400821 and PA200400822, both filed May 25, 2004. The entire content of all of which is incorporated herein by reference.

FIELD OF INVENTION

The present invention relates to a method and tools for extracting information relating to an influence, for example on intracellular molecule(s), in particular an influence caused by contacting a cellular molecule with a substance, which has been released from a solid support to which a cell expressing the cellular component is attached. In particular the method related to a solid support that allow chemical synthesis of individual substances on beads of the solid support The method of the invention may be used as a very efficient procedure for testing or discovering the influence of a library of substances on a physiological process, for example in connection with screening for new drugs, testing of substances for toxicity, identifying drug targets for known or novel drugs. Other valuable uses of the method and technology of the invention will be apparent to the skilled person on the basis of the following disclosure

BACKGROUND OF INVENTION

Combinatorial synthesis of peptide as well as small-molecule libraries has proven very useful as a method for generating vast numbers of highly diverse compounds (see for example Comprehensive Survey of Combinatorial Library Synthesis: 2002 Roland E. Dolle J. Comb. Chem., 2003, pp. 693-753). To fully exploit this high capacity of combinatorial chemistry to produce huge numbers of compounds several technologies have been developed that allow screening directly on the solid support (M. Meldal, 1994, METHODS: A companion to methods of enzymology 6:417-424). In the field of drug discovery such methods have successfully been applied for example for the identification of enzyme modulators. The library can be synthesized on resin beads that each carry one specific compound, and these "one-bead-one compound" libraries are then screened against the purified biological component of interest (e.g. cellular proteins or peptides), Before progressing active compounds, identified though such procedure, further in the drug discovery process, the compound will have to be re-synthesized and tested for efficacy in a cell-based or in-vivo test system.

Novel ways to screen combinatorial libraries in a physiological more correct way are assumed to greatly accelerate the drug discovery process, and show importance in areas like chemo-genomics and chemo-proteomics.

Screening of combinatorial libraries in intact cells have been done by capturing mammalian or yeast cells together with a limited number of resin-beads in a "nanodroplet" (Borchart et al. Chem Biol 1997 4:961). Compounds immobilized on the resin are released through disruption of a photo-cleavable linker and the compound-associated effects on the intact cells are monitored.

In an alternative method the compounds are released through acidolysis resin-beads carrying the library members area are spread out on a lawn of mammalian cells, and the spatial localization of a cellular response is monitored and beads in that region is isolated, and the remaining compound is structure elucidated Jayawickreme et al, 1998, Combinatorial peptide Library Protocols, Ed. Shmuel Cabilly, Humana Press, p. 107-128). WO03/038431 describes methods for screening combinatorial bead libraries by capturing cells from body fluids. Beads comprising a compound enabling cells to adhere to said bead may be selected.

US2003/0059764 describes multiplexed cell analysis systems using non-positional or positional arrays of coded carriers.

SUMMARY OF INVENTION

It is of great importance to provide new and efficient methods for identification of compounds influencing specific cellular processes. In particular, such methods wherein a very large quantity of candidate compounds may be tested for a specific effect on a cell within a relatively short period of time.

It is therefore an object of the present invention to provide very efficient procedures for testing or discovering the influence of compounds of a library on a physiological process in a cell. In particular, the methods provides means for testing very large numbers of different compounds for one or more physiological effects within a rather short time period. This may be obtained by attaching living cells to resin beads coupled to a test compound. The test compounds may be released from the resin beads and thus influence physiological processes in said cells. Said influence(s) may be detected and beads containing cells displaying the desired influence(s) may be selected. Once selected the compounds coupled to the selected beads may be identified. These methods may for example be very useful in connection with screening for new drugs, testing of substances for toxicity, identifying drug targets for known or novel drugs.

Accordingly, it is a first objective of the invention to provide methods of identifying a compound modifying at least one cellular response, wherein each cellular response is linked to different reporter systems generating detectable outputs, said method comprising the steps of:
 (a) Providing multiple resin beads capable of supporting growth of cells, wherein each resin bead is linked to multiple copies of a member of a library of test compounds via a cleavable linker and wherein at least two beads comprise different library members; and
 (b) Attaching cells comprising said reporter system(s) onto said resin beads; and
 (c) Releasing a proportion of said library member from the resin bead; and
 (d) Screening said resin beads for beads comprising cells meeting at least one predetermined selection criterion, wherein said selection criterion is linked directly or indirectly to said detectable output; and
 (e) Selecting beads comprising cells meeting said at least one selection criterion; and
 (f) Identifying the library member remaining linked to the selected resin bead, thereby identifying a compound modifying said at least one cellular response.

The method involves release of a proportion of library member. The released library member may enter into cells in the immediate surroundings and thus influence cellular responses within said cells. In practical terms, the cells present in the immediate surroundings, will be the cells attached to the resin bead, from which the library member is released. Thus resin beads comprising cells, wherein the particular cellular response has been modified may be selected and the library member remaining bound to said resin beads can be identified.

The invention furthermore relates to methods of manufacturing a compound modifying at least one cellular response, wherein said method comprises the steps of:
a) Identifying said a compound modifying a cellular response according to the methods described herein
b) Preparing said compound by chemical synthesis
c) Thereby manufacturing said compound The invention also relates to methods of modulating the interaction between two cellular molecules comprising the steps of
a) Identifying a modulating interaction between two cellular molecules according to the methods described herein
b) Incubating said compound together with cells expressing said two cellular molecules
c) Thereby modulating the interaction between the two cellular molecules Depending on the nature of the two cellular molecules, specific cellular responses may be inhibited/activated. This may in particular be interesting for use of the compounds in therapy.

The invention furthermore relates to compounds identified by the methods disclosed herein.

DEFINITIONS

Figure 1A:
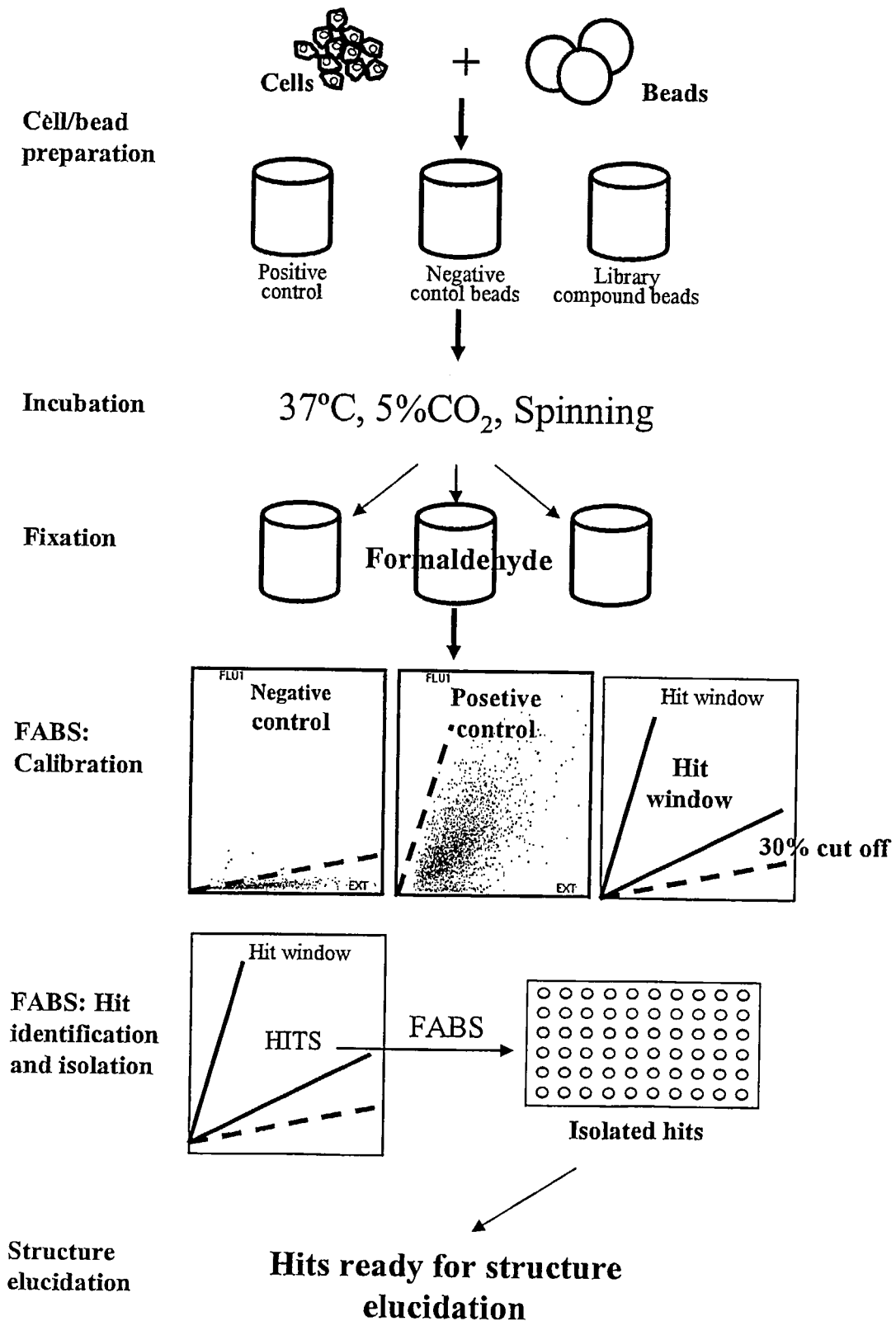
FIG. 1A illustrates a method of identifying a resin bead comprising a compound influencing a cellular response linked to a reporter system generating a fluorescent output. The method involves cultivating cells on resin beads, fixing cells. FABS calibration using a positive and a negative control, identification and isolation of positive hits.

Naturally occurring amino acids are named herein using either their 1-letter or 3-letter code. If nothing else is specified amino acids may be of D or L-form. In the description (but not in the sequence listing) 3-letter codes starting with a capital letter indicate amino acids of L-form, whereas 3-letter codes in small letters indicate amino acids of D-form. Three- and one-letter abbreviations for amino acids are used according to the recommendations from IUPAC, see for example http://www.chem.qmw.ac.uk/iupac.

The term "a" as used herein, can mean one or more, depending on the context in which it is used.

In the present context, the term "green fluorescent protein" or (GFP) is intended to indicate a protein which, when expressed by a cell, emits fluorescence upon exposure to light of the correct excitation wavelength (cf. [(Chalfie et al. 1994)]). "GFP" as used herein means any protein or fragment thereof capable of fluorescing when excited with appropriate radiation. This includes fluorescent proteins that are either naturally occurring or engineered and proteins that have been modified to be fluorescent. Naturally occurring fluorescent proteins have been isolated from the jellyfish, *Aequorea vistoria*, the sea pansy. *Renilla reniformis, Phialidium gregarium* and *Discosoma coral* (W. W. Ward et al. (1982) Photochem. Photobiol, 35:803-808; Levine et al. (1982) Biochem. Physiol., 72B:77-85; Fradkov et al. (2000), FEBS Lett. 479:127-130). GFPs have also been engineered to emit different colors and to fluoresce more intensely in mammalian organisms (U.S. Pat. No. 5,625,048; WO 97/28261; WO 96/23810; EP0851874; U.S. Pat. No. 6,172,188; WO01/98338).

A variety of *Aequorea*-related fluorescent proteins have been engineered to have different excitation and emission spectra by modifying the naturally occurring amino acid sequence (D. C. Prasher et al. (1992) Gene 111:229-233; Heim et al. (1994) Proc. Natl. Acad. Sci. USA 91: 12501-12504; U.S. Pat. No. 5,625,048; WO 96/23810 and PCT/US97/14593).

The term "living cell" is used to indicate a cell which is considered living according to standard criteria for that particular type of cell such as maintenance of normal membrane potential, cell membrane integrity and energy metabolism The terms "image processing" and "image analysis" are used to describe a large family of digital data analysis techniques or combination of such techniques which reduce ordered arrays of numbers (images) to quantitative information describing those ordered arrays of numbers. When said ordered arrays of numbers represent measured values from a physical process, the quantitative information derived is therefore a measure of the physical process.

The term "fluorescent probe" is used to indicate a fluorescent fusion polypeptide comprising a GFP or any functional part thereof which is N- or C-terminally fused to a biologically active polypeptide as defined herein, optionally via a peptide linker consisting of one or more amino acid residues, where the size of the linker peptide in itself is not critical as long as the desired functionality of the fluorescent probe is maintained. A fluorescent probe according to the invention is expressed in a cell and basically mimics the physiological behaviour of the biologically active polypeptide moiety of the fusion polypeptide.

The term "determining the fluorescence" is used to describe the process used to monitor a change in fluorescence properties.

The term "bioluminescence" is used to describe a process where light is produced through a chemical reaction that natively is occurring in a biological system. For the reaction to occur at least two chemicals are required: the one that produces the light (called "luciferin") and the other (called "luciferase") that catalyzes the reaction. Sometimes the luciferin and luciferase are brought together in one single unit (called "photoprotein" an example of the last group is aequorin.

The term "FRET" is used to describe the occurrence of Fluorescence resonance energy transfer between a fluorophore donor and an acceptor fluorophore. It is a distance-dependent interaction between the electronic excited states of two fluorophores in which excitation is transferred from a donor fluorophore to an acceptor fluorophore without emission of a photon. The efficiency of FRET is dependent on the inverse sixth power of the intermolecular separation, making it useful over distances comparable with the dimensions of biological macromolecules. Thus. FRET is an important technique for investigating interactions between cellular molecules for example complex formation.

The term "BRET" is used to describe a process that is related to FRET, but differs from FRET in that donor is a bioluminescent protein like luciferase that generates its own luminescence emission in the presence of a substrate, and that can pass the energy to an acceptor fluorophore. For either BRET or FRET to work, the donor's emission spectrum must overlap the acceptor's absorption spectrum, their transition dipoles must be in an appropriate orientation, and the donor and acceptor must be in close proximity (usually within 30-80 Å of each other, depending on the degree of spectral overlap).

The term "Scintillation Proximity Assay" is used to describe an assay determining the distance between two compounds, wherein one compound (bound to a bead) will emit light when radiation from an isotope occurs in close proximity and the other compound is containing a radioactive isotope.

The term "Proximity ligation" is used to describe an assay determining the presence of a target molecule through the convergence of two different protein-binding reagents that specifically recognise said target molecule. Attached to each protein-binding reagent are nucleic acid sequences that when broad into close proximity will create a DNA reporter sequence through a ligation reaction (see Gullberg et al. Curr Opinion Biotechnology 2003, 14:82)

The term "mammalian cell" is intended to indicate any cell of mammalian origin. The cell may be an established cell line, many of which are available from The American Type Culture Collection (ATCC, Virginia, USA) or a primary cell with a limited life span derived from a mammalian tissue, including tissues derived from a transgenic animal, or a newly established immortal cell line derived from a mammalian tissue including transgenic tissues, or a hybrid cell or cell line derived by fusing different celltypes of mammalian origin e.g. hybridoma cell lines. The cells may optionally express one or more non-native gene products, e.g. receptors.

The phrase "fluorescence properties" means absorption properties, such as wavelength and extension, and spectral properties of the emitted light, such as wavelength, fluorescence lifetime, intensity or polarisation, or the intracellular localisation of the fluorophore. It may thus be localised to a specific cellular component (e.g. organelle, membrane, cytoskeleton, molecular structure) or it may be evenly distributed throughout the cell or parts of the cell.

The term "fixed cells" is meant to cover cells treated with a cytological fixative such as glutaraldehyde, methanol, acetone or formaldehyde, treatments which serve to chemically cross-link and/or stabilize soluble and insoluble proteins within the structure of the cell or to dehydrate cells. Once in this state, such proteins cannot be lost from the structure of the now-dead cell.

The term "cell line" is meant to cover a group of cells, wherein the cells of that group are essentially genetically indistinguishable from each other. The cells of a cell line are thus all progeny of the same cell.

The term "comprising" should be understood in an inclusive manner. Hence, by way of example, a composition comprising compound X, may comprise compound X and optionally additional compounds.

The term "multiple" should be understood as "at least two".

The term "library of test compounds" should be understood as a collection of test compounds comprising at least 2 different test compounds.

The term "small organic molecules or compounds" refers herein to non-oligomeric, carbon containing compounds producible by chemical synthesis and generally having a size of less than 600 mass units.

The term split/mix refer herein to the process of i) dividing a bead assembly into m portions and reacting each portions with a different building block followed by mixing the resin into one portion providing an even distribution throughout the assembly of beads containing said building blocks, ii) preparing (activating) the resin for attachment of the next building block and repeating the process n times of dividing, reacting, mixing and activating, thus providing an exponential growth of the number ($m^n$) of distinct molecular entities of complexity n each attached to separate beads.

The term "one bead-one compound library" refers to libraries immobilised on resin beads, wherein each individual resin bead does not comprise more than one library member in one or multiple copies. In a particular form of such libraries each member is represented by multiple fragments of said member obtained by ladder synthesis encoding.

The term "one bead-two compound library" refers to libraries immobilised on resin beads, wherein each individual resin bead does not comprise more than one library member in one or multiple copies and wherein each individual resin bead in addition to said library member also comprises an adhesion compound. All beads may comprise identical adhesion compounds.

The term "cleavable linker" is used to describe any chemical moiety which may be used to attach any molecule to a solid support either covalently or via complex formation and thereafter release said molecule by the action of either acid, base, electrophiles, nucleophiles, oxidative agents, reductive agents, metals, heat or light.

DETAILED DESCRIPTION OF THE INVENTION

Library of Test Compounds

In the present invention, libraries of compounds are used to screen for compounds having a desired physiological influence on a living cell. As used herein, the term "library" means a collection of molecular entities or test compounds, herein also designated "library members" obtained after a series of chemical transformation.

In preferred embodiments of the present invention the library is a combinatorial library. Non-limiting examples of combinatorial libraries that may be used with the present invention and methods of producing such libraries are given in: Comprehensive Survey of Combinatorial Library Synthesis: 1998 Roland E. Dolle and Kingsley H. Nelson, Jr. J. Comb. Chem., 1999, pp 235-282; Comprehensive Survey of Combinatorial Library Synthesis: 1999 Roland E. Dolle J. Comb. Chem., 2000, pp 383-433; Comprehensive Survey of Combinatorial Library Synthesis: 2000 Roland E. Dolle J. Comb. Chem., 2001, pp 477-517; Comprehensive Survey of Combinatorial Library Synthesis: 2001 Roland E. Dolle J. Comb.

Chem., 2002, pp 369-418 and Comprehensive Survey of Combinatorial Library Synthesis: 2002 Roland E. Dolle J. Comb. Chem., 2003, pp 693-753. The skilled person will appreciate that these protocols may be easily be adapted to specific need of a particular embodiment of the present invention.

In one embodiment, these molecular entities can be natural oligomers (oligomers of building blocks occurring in Nature) such as peptides, glycopeptides, lipopeptides, nucleic acids (DNA or RNA), or oligosaccharides. By way of example, a natural oligomer may be any peptide consisting of naturally occurring amino acid, even if said peptide comprises a sequence not present in nature. The libraries may comprise different natural oligomers or the libraries may comprise only one kind of natural oligomer, for example the library may be a peptide library. In another embodiment, they can be unnatural oligomers (oligomers comprising one or more building blocks not occurring in Nature) such as chemically modified peptides, glycopeptides, nucleic acids (DNA or RNA), or, oligosaccharides, and the like. Said chemical modification may for example be the use of unnatural building blocks connected by the natural bond linking the units (for example, a peptide amide linkage), the use of natural building blocks with modified linking units (for example, oligoureas as discussed in Boeijen et al, 2001, J. Org. Chem., 66: 8454-8462; oligosulfonamides as discussed in Monnee et al, 2000, Tetrahedron Lett., 41: 7991-95), or combinations of these (for example, statine amides as discussed in Dolle et al, 2000, J. Comb. Chem., 2: 716-31.). Preferred unnatural oligomers include oligomers comprising unnatural building blocks connected to each other by a naturally occurring bond linking. Said oligomers may thus comprise a mixture of naturally occurring and unnatural building blocks linked to each other by naturally occurring bonds. By way of example, the oligomer may comprise naturally occurring amino acids and unnatural building blocks linked by peptide bonds f.x. PNA or LNA. Thus, in one embodiment of the invention preferred oligomers comprise modified amino acids or amino acid (mimics). Other preferred unnatural oligomers include, for example oligoureas, poly azatides, aromatic C—C linked oligomers and aromatic C—N linked oligomers. Still other preferred oligomers comprise a mixture of natural and unnatural building blocks and natural and unnatural linking bonds. For example, the unnatural oligomer may be any of the oligomers mentioned in recent reviews see: Graven et al., 2001, J. Comb. Chem., 3: 441-52; St. Hilaire et al., 2000, Angew. Chem. Int. Ed. Engl., 39: 1162-79; James, 2001, Curr. Opin. Pharmacol., 1: 540-6; Marcaurelle et al., 2002, Curr. Opin. Chem. Biol., 6: 289-96; Breinbauer et al., 2002, Angew. Chem. Int. Ed. Engl., 41: 2879-90. The libraries of the invention may also comprise cyclic oligomers, for example cyclic natural oligomers, such as cyclic peptides or cyclic unnatural oligomers. In certain embodiments of the invention, libraries of cyclic oligomers may be advantageous to use due to the rigid structure. This may result in higher selectively and affinity.

In yet another embodiment, the molecular entities may comprise non-oligomeric molecules such as peptidomimetics or other small organic molecules. Peptidomimetics are compounds that mimic the action of a peptidic messenger, such as bicyclic thiazolidine lactam peptidomimetics of L-proplyl-L-leucyl-glycinamide (Khalil et al, 1999, J. Med. Chem., 42: 2977-87). In a preferred embodiment of the invention, the library comprises or even more preferably consists of small organic molecules. Small organic molecules are non-oligomeric compounds of less than about 600 mass units containing any of a variety of possible functional groups and are the product of chemical synthesis, or isolated from nature, or isolated from nature and then chemically modified, and include, for example, Bayer's urea-based kinase inhibitors (Smith et al., 2001, Bioorg. Med. Chem. Lett., 11: 2775-78). Small organic compounds may for example be selected from the group consisting of alcohols, ethers, carboxylic acids, aryloxy, acyloxy, thiol, alkylthio, arylthio, heteroarylthio, sulphonyl, sulphoxy, amino, alkylamino, dialkylamino, acylamino, diacylamino, alkoxycarbonylamino, amides, alkyl, branched alkyl, aryl, heteroaryl, nitro, cyano, halogeno, silyloxy, keto, heterocycles, fused ring systems, fused heterocycles and mixtures thereof, wherein each of the aforementioned may be substituted independently on each position with one or more groups selected from the group consisting of —H, —OH, —SH, halogen, carboxyl, carbonyl, alkoxy, aryloxy, acyloxy, alkylthio, arylthio, heteroarylthio, sulphonyl, sulphoxy, amino, alkylamino, dialkylamino, acylamino, diacylamino, alkoxycarbonylamino, amides, alkyl, aryl, heteroaryl, nitro, cyano, halogeno, silyloxy, keto, heterocycles, fused ring systems, and fused heterocycles.

Non-limiting examples of small organic molecule libraries that may be used with the present invention and methods of producing them may for example be found in the reviews Thompson et al., 1996, Chem. Rev., 96: 555-600; Al-Obeidi et al., 1998, Mol. Biotechnol., 9: 205-23; Nefzi et al., 2001, Biopolymers, 60: 212-9; Dolle, 2002, J. Comb. Chem., 4: 369-418.

The libraries according to the invention may comprise at least 20, such as at least 100, for example at least 1000, such as at least 10,000, for example at least 100,000, such as at least 1,000,000 different test compounds. Preferably, the libraries comprises in the range of 20 to $10^7$, more preferably 50 to 7,000,000, even more preferably 100 to 5,000,000, yet more preferably 250 to 2,000,000 different compounds. In a very preferred embodiment of the present invention the libraries comprises in the range of 1000 to 20,000 or for example in the range of 20,000 to 200,000 different test compounds.

In preferred embodiments of the invention the library comprises in the range of 10,000 to 1,000,000 different test compounds.

Preferably, the libraries to be used with the present invention are immobilised on resin beads. Said resin beads may be any of the beads described herein below. At least 2, preferably at least 20, more preferably at least 100, even more preferably at least 1000, yet more preferably at least 10,000, for example at least 100,000, such as at least 1,000,000 resin beads comprising different library members, i.e. different test compounds may be used with the methods according to the invention. Preferably, the in the range of 20 to $10^7$, more preferably 100 to 7,000,000, even more preferably 1000 to 5,000,000, yet more preferably 5000 to 2,000,000, even more preferably 10,000 to 1,000,000 resin beads comprising different library members, are used with the methods according to the invention.

In one very preferred embodiment of the invention, each resin bead does not comprise more than one library member in one or more copies, i.e. each resin bead only comprises one kind of test compound, however said test compound may be present on the resin bead in multiple copies. Such libraries may also be designated one-bead-one-compound libraries. Preferably, each resin beads comprises sufficient copies of said library member in order to exert the desired influence of cells attached to said resin bead and in order to analyse the chemical structure of the compound. Such libraries may be prepared by different methods, for example by a split/mix method or by coupling individually a specific compound to a bead. One-bead-one compound libraries offer the advantage that once a resin bead has been selected according to the methods described herein, the desired compound may easily be identified (see useful methods herein below).

The libraries may in one preferred embodiment be synthesized directly on resin beads using a split/mix method (vide infra) which gives rise to one-bead-one-compound libraries. Split/mix methods in general comprise the steps of:
1. Providing several pools of resin beads
2. Performing one or more different chemical synthesis steps on each pool of resin beads
3. Mixing pools of resin beads, thereby obtaining a mixed pool.
4. Splitting the mixed pool of resin beads thereby obtaining new pools.
5. Optionally repeating step 1 and 4

Alternatively steps 3 and 4 may be as follows:
3. Splitting said pools to obtain fractions
4. Mixing fractions from different pools, thereby obtaining new pools One-bead-one-compound libraries may for example be prepared as described in M. Meldal, Multiple column synthesis of quenched solid-phase bound fluorogenic substrates for characterization of endoprotease specificity in Methods: A Companion to Methods in Enzymology 6:417-424, 1994 or in M. Meldal, The One-bead Two-Compound Assay for Solid Phase Screening of Combinatorial Libraries in Biopolymers, Peptide Science 66:93-100, 2002; or in Combinatorial peptide library protocols, Ed. by Shmuel Cabilly, Humana Press, 1998, p. 1-24 and 51 to 82.

In one embodiment of the invention the library may be a library of oligomers of amino acids immobilised on resin beads, wherein said amino acids may be naturally occurring amino acids or any other kind of amino acid or a mixture of both. In general, oligomers of amino acids are referred to as peptides, regardless whether they comprise naturally occurring or not naturally occurring amino acids or a mixture, unless it is clear from the context that the term only cover oligomers of naturally occurring amino acids. For example, the oligomers may comprise or consist of at least 3, such as at least 4, for example at least 5, such as at least 6, for example at least 7, such as at least 10, for example at least 20, such as in the range of 3 to 5, for example in the range of 4 to 10, such as in the range of 5 to 15, for example in the range of 10 to 20 amino acids, such as in the range of 15 to 30, for example in the range of 3 to 50, such as in the range of 3 to 25, for example in the range of 4 to 15 amino acids. Such libraries may for example be prepared as described in example 1 herein below.

The library of oligomers of amino acids may in one embodiment comprise an appended sequence. Thus, every library member may share a common sequence, i.e. the appended sequence. In addition every library member comprises an individual sequence. The appended sequence may be a sequence of amino acids, for example in the range of 3 to 5, for example in the range of 4 to 10, such as in the range of 5 to 15, for example in the range of 10 to 20 amino acids, such as in the range of 15 to 30, for example in the range of 3 to 50, such as in the range of 3 to 25, for example in the range of 4 to 15 amino acids.

In another embodiment of the invention the library may be a one-bead-two-compounds library. Each individual resin bead of such a library comprises only one library member in one or more copies. In addition each individual resin bead comprises a second compound, such as a cell adhesion compound. The cell adhesion compound could for example be any of the cell adhesion compounds mentioned herein below. It is comprised within the invention that several library resin beads, such as all library resin beads comprises identical adhesion compound(s) in one or more copies. One-bead-two-compound libraries may for example be prepared by a method involving the steps of:
1. Providing resin beads comprising a plurality of reactive groups
2. Reacting said reactive groups with two chemical moeities comprising different and preferably orthogonal protective groups
3. Deprotecting a subset of the reactive groups by removal of one kind of protective groups, preferably selective removal of one kind of protective group,
4. Attaching or synthesizing a split/mix library of test compounds to the deprotected reactive group
5. Deprotecting the remaining reactive groups by removal the other kind of protective group
6. Attaching the second compound to the deprotected reactive groups The method may also be performed by first attaching the second compound and then synthesizing the library. Accordingly, the steps of the method may be performed in the following order: 1, 2, 3, 6, 5 and 4. The library of test compounds may be first synthesized and then attached to the resin beads or it may be synthesized directly into the resin bead. Similarly, the second compound may be first synthesized and then attached to the resin beads or it may be synthesized directly into the resin bead.

Preferred resin beads are described in the section "resin beads" herein below. The reactive group may be any suitable reactive group, preferably however, the reactive group is either a hydroxyl group, a thiol or a primary amino group. The reactive group may also preferably be an azido or a secondary amino group. The protective group may be any suitable protective group known to the person skilled in the art, such as acid labile, alkaline labile, fluoride labile, oxidation labile, reduction labile or photolabile protective groups, preferably the protective group is selected from the group consisting of Fmoc, Boc, Alloc and $N_3$. It is preferred that the different protective groups may be removed by different treatment, for example that if one protective group is acid labile, then the other is not acid labile, but instead for example alkaline labile or photo labile. In an preferred embodiment one protective group is Fmoc and the other protective group is Alloc or $N_3$. Step 3 may for example be performed by a split/mix method as described herein above, thereby generating a one-bead-one-compound library. The second compound is preferably a cell adhesion compound.

In yet another embodiment of the invention the library may be a mixed compound library, wherein each individual resin bead comprises a plurality of library members.

Selection of an appropriate library is dependent upon the specific embodiment of the invention. For example, a totally random library designed to contain interesting and greatly diverse compounds may be used with the invention. An advantage of this approach is that the outcome of the screening is not prejudiced in any specific manner or at least less prejudiced. Since the invention permits screening of millions of diverse compounds, for example, immobilized on resin beads, a large number, for example in the range of 3 to 5 million, of random molecules can be used in the ligand library.

Alternatively, a smaller, targeted library (hundreds to thousands of compounds) can be used, for example, starting with a known compound or compounds, and providing numerous variations of these known compounds for targeted screening. For example, in embodiments of the invention wherein compounds modulating the activity of a specific cell surface molecule, a compound known to modulate said specific cell surface molecule may be used as starting compound for the preparation of a targeted library. Alternatively, a smaller targeted library of compounds mimicking a compound known to modulate the activity of said cell surface molecule may be prepared, for example using computer aided modelling followed by chemical synthesis. The smaller, targeted library can also comprise random molecules. Examples of libraries and methods of preparing such libraries, which may useful in embodiments of the invention, wherein the cellular response is mediated through an intracellular signalling pathway are known to the skilled person. The library may contain a parallel array of random modifications of one or more test compounds. In one embodiment, the library may be formed as a parallel array of random modifications to a known compound or compounds. The term "parallel array" is meant to cover synthesis of a library by subjecting a given compound to a known set of reactions in an isolated vessel or well. Thus, the nature of a compound in a given container or well is known. The array of test compounds is preferably prepared directly on resin beads using techniques known by those skilled in the art. Briefly, the resin may be portioned into a number of vessels or wells, usually less than 500 and the reagents added. There is in general no mixing step and after the appropriate washing steps, subsequent reactions are carried out by addition of additional reagents to the wells. There is no exponential increase in the number of compounds generated and that is equal to the number of vessels used. The compound can be easily identified by keeping track of the reagent added to each well.

The library may also have been prepared by parallel synthesis using a tag to enable identification of, what chemical synthesis steps the individual resin bead has been submitted to. This may for example be done by IRORI or radiofrequency tag. Alternatively, chemical synthesis steps may be performed in parallel to preparing a polymeric tag. Identification of the tag will thus provide knowledge of the compound.

Attachment of a label to a compound may alter the properties of said compound. Hence, in one embodiment of the present invention, the compounds of the library are not labelled, i.e. the compounds are not connected to a detectable label, such as a fluorescent component, a nucleic acid or a nucleic acid homologue such as PNA, a dye, a probe comprising a reactive moiety or the like. In particular it is preferred that all compounds are not connected to the same detectable label.

The peptides used for preparation of any of the libraries mentioned above may be oligomers of naturally occurring or not naturally occurring amino acids or a mixture of both, preferably they are oligomers of the 20 amino acids naturally present in proteins, wherein said amino acids may be in either D- or L-form. It is preferred that each peptide (or peptide mimetic) is immobilised on a solid support, such as any of the solid supports mentioned herein below. More preferably the solid support is resin beads and it is preferred that each resin bead comprises only one library member in one or more copies.

Preferably at least 2, such as at least 10, for example at least 100, such as at least 1000, for example at least 10,000 different peptides and/or peptide mimetics are provided. Each peptide may comprise in the range of 2 to 100 amino acids, such as in the range of 2 to 50 amino acids, for example 2 to 25 amino acids, such as in the range of 2 to 15 amino acids, for example 2 to 10 amino acids, such as in the range of 3 to 8 amino acids, for example 4 to 6 amino acids, The invention also relates to libraries prepared by any of the methods described above. Libraries of heterocyclic compounds obtained by cyclisation of a peptide aldehyde through an intramolecular Pictet-Spengler reaction may also be used with the present invention. Such libraries may for example be any of the libraries described in Danish patent application PA 2003 00967, which is hereby incorporated by reference.

In one embodiment of the invention the library comprises oligomers of amino acids, such as oligomers of 3 to 10 amino acids, such as oligomers of 3 to 6 amino acids, for example oligomers of 3 to 4 amino acids, wherein the oligomer optionally may comprise additional moieties, such as 1 to 4, for example 1 to 3, such as 1 to 2, for example 1 additional moiety, which is not an amino acid. The additional moiety may be an acyl moiety, such as an acyl halide. The additional moiety is preferably situated at one end of the oligomer, preferably at the C-terminus. The amino acids may be either naturally occurring or not naturally occurring amino acids or a mixture of both. They are preferably linked via peptide bonds. In one embodiment the library comprising compounds consisting of 3 amino acids linked via peptide bonds and an additional moeity which may be an amino acid or for example an acyl halid. Such libraries may for example be useful for identifying compounds capable of interacting with inhibitors of apoptosis, such as ML-IAP or XIAP. Examples of such libraries and methods of preparing such libraries are described herein below in Examples 4, 5a, 5b and 5c. In one embodiment libraries prepared essentially as described in examples 5b or 5c are preferred.

In one embodiment the library may comprise or essentially consist of oligomers of amino acids, such as oligomers of in the range of 3 to 6 amino acids, for example oligomers of 4 amino acids, wherein the amino acids are selected from the group of amino acids mentioned in table 3, table 4, table 5 and table 6. A preferred example of such a library is given in example 4.

Resin Beads

The library members of this invention are preferably bound to a solid support. Preferred solid supports to be used with the present invention are resin beads (see herein below). The solid support may however also be a spot or region on a surface or a plated gel or a membrane. A spot or a region is a defined area on said surface, to which the library member is bound via a cleavable linker. One can therefore envisage one surface comprising a plurality of spots or regions, wherein each such spot or region is covalently attached to only one library member in one or more copies. Said surface could for example be a silicium wafer, a glass surface, a plastic surface or a gel. Plastic surface may for example be prepared from polystyrene, polycarbonate polypropylene, ethylene and/or teflon. Gels could be prepared from for example poly acrylamid or PEGA.

In this invention however, the compounds of the library are preferably bound to a resin bead, conferring the advantage of compartmentalized "mini-reaction vessels" for attachment of cells.

In general more compounds may be screened and several of the steps in the procedure may be performed on one bead with sufficient material. Hence, preferably, the library is bound to resin beads. Each member of the library is a unique compound and is physically separated in space from the other compounds in the library, preferably, by immobilizing the library on resin beads, wherein each bead at the most comprises one member of the library. Depending on the mode of library synthesis, each library member may contain, in addition, fragments of the library member. Since ease and speed are important features of this process invention, it is preferred that the screening step take place on the same solid support used for synthesis of the library, and also that identification of the members of the binding pair can take place on the same support, such as on a single resin bead. Thus, preferred solid supports useful in the process invention satisfy the criteria of not only being suitable for organic synthesis, but are also suitable for screening procedures, such as "onbead" screening as well as suitable for attachment of cells. It is furthermore preferred that the resin bead is suitable for "on-bead" identification of library members as described herein below. The resin bead may be prepared from any suitable material such as polystyrene, polyethylene, polyacrylamide, controlled pore glass or PEG. The resin bead could thus for example be selected from the group consisting of Toyopearl, sepharose, sephadex, CPG, silica, POPOP, PEGA, SPOCC, Expansin, Tentagel, Argogel, Polystyrene, Jandagel, polydimethylacrylamide resin, Polyacrylamide resin, kieselghur supported resins and polystyrene supported resins.

Hydrophilic supports are preferred. Examples of preferred hydrophilic resin beads includes TentaGel (commercially available from Rapp polymere, Tübingen, Germany), Argo-Gel (commercially available from Argonaut Technologies Inc., San Carlos, Calif.), PEGA (commercially available from VersaMatrix, Copenhagen), POEPOP (Renil et al., 1996, Tetrahedron Lett., 37: 6185-88; available from Versamatrix, Copenhagen, Denmark) and SPOCC (Rademann et al, 1999, J. Am. Chem. Soc., 121: 5459-66; available from Versamatrix, Copenhagen, Denmark). Examples of on-bead screening attempts are described in the following references: Chen et al., 1996, Methods Enzymol., 267: 211-19; Leon et al., 1998, Bioorg. Med. Chem. Lett., 8: 2997-3002; St. Hilaire et al., 1999, J. Comb. Chem., 1: 509-23; Smith et al., 1999, J. Comb. Chem., 1: 326-32; Graven et al., 2001, J. Comb. Chem. 3: 441-52; Park et al., 2002, Lett. Peptide Sci., 8: 171-78). TentaGel and ArgoGel are made up of polyethylene glycol chains grafted on to a polystyrene core. However, use of these supports in biological screening is limited by a size restriction, and by denaturation of certain proteins, particularly enzymes.

Preferred resin beads according to the present invention are resin beads, useful for on-bead library synthesis, screening and identification of ligand/protein. Hence, preferred resins according to the present invention are resin comprising polyethylene glycol. More preferably, the resin is PolyEthyleneGlycol Acrylamide copolymer (PEGA), Super Permeable Organic Combinatorial Chemistry (SPOCC) resin or PolyOxyEthylene-PolyOxyPropylene (POEPOP) resin. Another preferred resin comprises a crosslinked polyacrylamide resin.

PEGA (PolyEthyleneGlycol Acrylamide copolymer; Meldal M., 1992, Tetrahedron Lett., 33: 3077-80), POEPOP (PolyOxyEthylene-PolyOxyPropylene resin; Renil et al., 1996, Tetrahedron Lett., 37: 6185-88) and SPOCC (Super Permeable Organic Combinatorial Chemistry resin; Rademann et al, 1999, J. Am. Chem. Soc., 121: 5459-66) resins are made primarily of polyethylene glycol and swell well in organic as well as aqueous solvents. Because they have very reduced or no non-specific binding, PEGA and SPOCC resins have been effectively used in the screening of myriad proteins including enzymes of different classes. Furthermore, these resins are available in different pore sizes and can allow large proteins to enter while retaining activity. For example, PEGA6000 resins allow proteins up to 600 kDa to enter. In the Examples below, PEGA4000 and PEGA1900 resin with a molecular weight cut off of 200 and 90 kDa, respectively, were used for screening. In principle, any hydrophilic support that is useful for compartmentalized synthesis, retains the activity of the proteins, and has minimal non-specific binding, may be used in this process invention.

One aspect of the invention relates to a method comprising the step of providing multiple resin beads capable of supporting growth of cells. Preferably, all resin beads provided are capable of supporting growth of cells. In one preferred embodiment all resin beads are similar and each is capable of supporting growth of cells, wherein the resin beads only differs by comprising different library members. In embodiments of the invention wherein the resin beads comprise a cell adhesion molecule, it is preferred that at least 10%, more preferably at least 20%, even more preferably at least 30%, yet more preferably at least 40%, even more preferably at least 50%, yet more preferably at least 60%, %, even more preferably at least 70%, yet more preferably at least 90%, even more preferably essentially all, yet more preferably all resin beads comprise the cell adhesion molecule as well as a library member.

Release of Library Compounds or of Adhesion Compound

The library of test compounds is preferably linked to the resin beads or solid supports by a cleavable linker. Hence in one embodiment of the invention, a proportion of the library members may be released from the resin beads, preferably by cleaving the cleavable linker. The thus released library members may then interact with cells in the immediate proximity, i.e. normally with cells attached to the same bead, and it is even possible that the library member may enter the cells and interact with intracellular compounds. Later selection of a single bead allows elucidation of the structure of the specific library member remaining attached to said bead.

Preferably, "releasing a proportion of a library member" means releasing one or more copies of the library member attached to a solid support or resin bead. Preferably, said copies of the library member are released by cleaving the cleavable linker. Preferably, in the range of 5 to 95% of all copies of a library member attached to a resin bead are released, more preferably in the range of 10 to 90%, even more preferably in the range of 20 to 80%, such as in the range of 30 to 70%, for example in the range of 40 to 60%, such as at least 5%, for example at least 10%, such as at least 20%, such as at least 30%, for example at least 40%, such as at least 50%, for example at least 60%, such as at least 70%, for example at least 80%, such as at least 90%, for example at least 95%, such as at the most 5%, for example at the most 10%, such as at the most 20%, such as at the most 30%, for example at the most 40%, such as at the most 50%, for example at the most 60%, such as at the most 70%, for example at the most 80%, such as at the most 90%, for example at the most 95% of all copies of a library member attached to a resin bead are released.

It is also comprised within the invention that the adhesion compound may be attached to the resin bead via a cleavable linker. Cleavage of said cleavable linker may release the adhesion compound as well as cells attached to said adhesion compound. When the cleavable linkers linking the library compound and the adhesion compound, respectively, are differentially cleavable, then selective release of either library compound or adhesion compound may be achieved.

The cleavable linker may be any chemical moiety which may be used to attach any molecule to a solid support either covalently or via complex formation, and thereafter release said molecule by the action of either acid, base, electrophiles, nucleophiles, oxidative agents, reductive agents, metals or light. Preferably, the cleavable linker attaches the library member to the solid support covalently. Depending on the nature of the cleavable linker, a person skilled in the art will be capable of controlling cleavage of the cleavable linker, so only a proportion of the copies of a library member are released. A comprehensive review describing state of the art for "cleavable linkers" is "Linkers and Cleavage Strategies in Solid-Phase Organic Synthesis and Combinatorial Chemistry", F. Guillier, D. Orain, and M. Bradley, Chem. Rev. 2000, 100, 2091-2157. Any of the cleavable linkers described therein may be used with the present invention.

Figure 4:
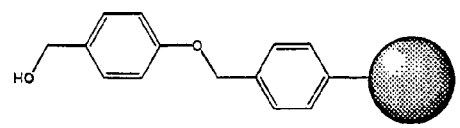
FIG. 4 illustrates examples of cleavable linkers useful with the present invention.
Figure 4:
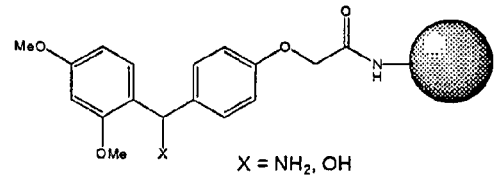
Figure 4:
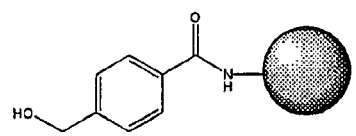
Figure 4:
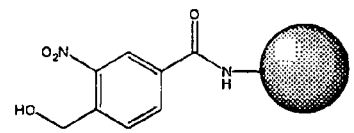
Figure 4:
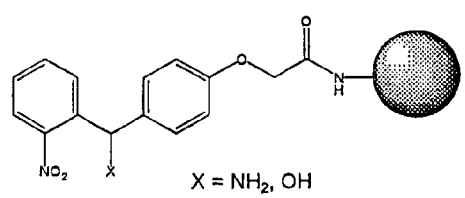
Figure 4:
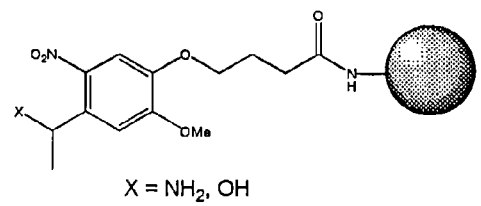

Examples of useful acid labile linkers include the most commonly used linkers for acidic detachment from a solid support, the Wang and Rink linkers (FIGS. 4A and B). Detachment of peptide esters from Wang linkers require up to 95% TFA in DCM whereas detachment of Rink esters (FIG. 4B, X=OH) may be cleaved under milder conditions (AcOH-DCM 1:9) which does not cleave the normal protection groups on the peptides. The Rink amides (FIG. 4A, X=NH$_2$) require 95% TFA (aq). Partial detachment of the compounds attached to the resin may also be achieved using gaseous acids such as HCL or TFA vapour in a sealed container. The use of gases allow rigorous control of the degree of cleavage obtained with concentration of acid and time of exposure. The skilled person may readily establish a suitable concentration of acid and time of exposure to obtain a desired degree of cleavage.

Examples of useful base-labile linkers includes Wang and HMBA linkers, which may be cleaved under alkaline conditions. Saponification with 0.1 M NaOH may be applied but even milder conditions such as potassium carbonate in MeOH are applicable. The HMBA linker is stable to TFA under normal conditions.

In a preferred embodiment the cleavable linker is a light sensitive cleavable linker which, upon the action of light with a given wave length and intensity, may release any active compound from the solid support.

Photo-labile linkers provide a tool for solid phase synthesis which enables the detachment of the synthesized molecules in the presence of acid or base-sensitive functionalities within the molecules. In 1973 Rich proposed the use of o-nitrobenzyl type of linkers (nitrated analogs of the Wang linker). Irradiation with UV-light gave detachment of the free acids or amides although only in moderate yields. Detachment yields could be improved by applying the NBA type linkers (see FIG. 4E). Even better result have been obtained with the Holmes-type linkers (FIG. 4F). Detachment from photolabile linkers is performed by illuminating the resins with ultraviolet light, preferable at 365 nm. The wave length and intensity of the light and the time of exposure might need optimization for the individual case. A person skilled in the art can readily establish conditions wherein a desired proportion of copies of a library member are released. Detachment yields may be over 90% under ideal conditions.

Example of a preferred photo sensitive cleavable linker:

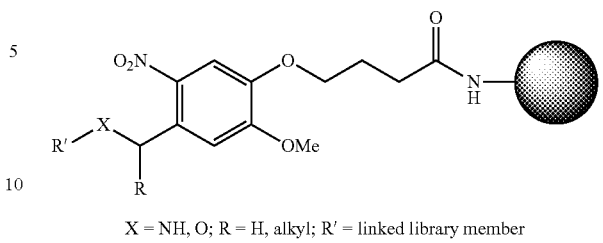

X = NH, O; R = H, alkyl; R' = linked library member

Depending on the nature of the cleavable linker, the library member may be released using different methods. For example, if the linker is photo labile, the library member may be released by illumination. The release should preferably be partial, so that only a proportion of the library member is released. The person skilled in the art will readily be able to establish the conditions required for partial release using a specific cleavable linker. An example of how to achieve partial release is given in example 6 herein below.

It is also comprised within the present invention that a library member may be linked to a resin bead via different cleavable linker. For example some copies of a library member may be linked to a resin bead via a first kind of cleavable linker, whereas other copies of the same library member may be linked to the resin bead via a second kind of cleavable linker. Preferably, the first kind of cleavable linker is cleavable by another method than the second kind of cleavable linker. By way of example, the first cleavable linker could be acid or base labile, whereas the second kind of cleavable linker could be photolabile. Thus, some copies of the library member could be released during the screening procedure of the invention, for example during step c) in the method outlined in the "Summary" herein above, whereas other copies could be retained on the resin beads and released during the identification, for example during step f) in the method outlined in the "Summary" herein above. Thus, releasing a proportion of a library member could be controlled by using different cleavable linkers.

Cells

The cells to be used with the present invention may be any useful cells available or prepared for the purpose. Preferably, the cells are selected from the group consisting of mammalian cells. For example the cells may be human cells. The cells may be cells capable of growing in suspension or they may be adherent cells. Adherent cells may preferably be cultivated directly on the resin beads used with the invention (see also herein below). It is preferred that the cells are adherent cells. Cells with a better adherence are preferred over cells with a poorer adherence. Cells which adhere well to resin beads comprising an adhesion compound as described herein above are very preferred.

Cells could for example be primary cells or established cell lines. Preferred cell lines include but are not limited to those mentioned in table 1.

TABLE 1

| Cell line | Species | Tissue | Morphology |
| --- | --- | --- | --- |
| 3T3-L1 | Mouse | Embryonic fibroblast | Fibroblast |
| 3T3-Swiss albino (CCL-92) | Mouse | Embryo | Fibroblast |
| A10 | Rat | thoracic aorta | Myoblast |

TABLE 1-continued

| Cell line | Species | Tissue | Morphology |
|---|---|---|---|
| Att 20 | Mouse | Pituitary | Small round cells |
| BAE | Cow | Aorta | Endothelial |
| Balb/c | Mouse | Embryonic fibroblast | Fibroblast |
| BHK:R P.1#4aa PTP1B fl | | | |
| BHK-21 | Hamster | Kidney | Fibroblast |
| BHK467 | Hamster | Kidney | |
| BHK570 | Hamster | Kidney | Fibroblast |
| BJ | Human | Foreskin | Fibroblast |
| C2C12 | Mouse | Muscle | Myoblast |
| Caki-1 | Human | Kidney | Epithelial |
| CAL-54 | Human | Kidney | Epithelial |
| CHOhIR | Chinese hamster | Ovary | Fibroblast |
| CHO-K1 | Hamster | Ovary | Epithelial |
| COS 1 | Monkey | Kidney | Fibroblast |
| COS 7 | Monkey | Kidney | Fibroblast |
| G-8 | Mouse | Muscle | Myoblast |
| GT1-7 | | | |
| HCT 116 | Human | Colorectal | Epithelial |
| HEK293 | Human | Embryonic kidney | Epithelial |
| Hela | Human | Cervix adenocarcinoma | Epithelial |
| HEP-G2 | Human | Liver | Epithelial |
| HT-1080 | Human | Fibrosarcoma | Epithelial |
| HT-29 | Human | Colon | Epithelial |
| HUVEC | Human | umbilical vein | Endothelial |
| Ins-1 | | | |
| Jurkat clone E6-1 | Human | T lymphocyte | Lymphoblastoid |
| K-562 | Human | Bone marrow | Lymphoblastoid |
| L-6 | Rat | Muscle | Myoblast |
| MCF 7 | Human | Mammary Gland | Epithelial |
| MDA-MB-231 | Human | Adenocarcinoma | Epithelial |
| MDA-MB-468 | Human | Mammary Gland | Epithelial |
| MDCK | Canine | Kidney | Epithelial |
| Min 6 | | | |
| Mv 1 Lu (NBL-7) | Mink | Lung | Epithelial |
| NIH-3T3 | Mouse | Embryo | Fibroblast |
| PAE | Pig | Aorta | |
| PC 12 | Rat | Adrenal gland | |
| PC-3 | Human | Prostate | Epithelial |
| RAT2 | Rat | Normal | Fibroblast |
| RAW 264.7 | Mouse | | Monocyte |
| RIN | Rat | | Epithelial |
| SK-ML-28 | Human | Melanoma | |
| SK-N-AS | Human | Neuroblastoma | Epithelial |
| SK-N-DZ | Human | Neuroblastoma | Epithelial |
| SK-N-F1 | Human | Brain | Epithelial |
| SK-NM-C | Human | Neuroepithelioma | Epithelial |
| SK-N-SH | Human | Caucasian neuroblastoma | Epithelial |
| SW480 | Human | Colorectal | Epithelial |
| U-2 OS | Human | Bone, osteosarcoma | Epithelial |
| U-87 MG | Human | Brain | Epithelial |
| U937 | Human | Lymphoma | Monocyte |
| VERO | Monkey | Kidney | Fibroblast-like |
| WI-38 | Human | Lung | Fibroblast |
| WM-266-4 | Human | Skin | Epithelial |
| WEHI | Human | | |

In one embodiment of the invention the cells have been genetically or otherwise modified in order to enhance their usability with the present invention. The modification may be stable or only transient or a mixture of both. For example, the cells may have been modified to contain one or more of the reporter systems described herein below. Depending on the nature of the reporter system this may be achieved by a number of different methods. For example, if the reporter system comprises a nucleic acid, said nucleic acid may be inserted into said cell by conventional recombinant techniques (see below).

In another preferred example the cell comprises nucleic acid comprising first nucleotide sequences encoding cellular proteins or polypeptides being part of an intracellular signal transduction pathway operationally linked to a reporter system detecting the enzymatic activity or subcellular localization of said first sequences, or detecting direct interactions between these first sequences.

Useful second sequences includes for example promoters active in the particular cells, for example mammalian promoters, viral promoters or synthetic promoters. A large number of useful eukaryotic promoters are known to the person skilled in the art, useful promoters are for example described in "Mechanism of Transcription" (1998) Cold Spring Harbor Symposia on Quantitative Biology Vol. LXIII; Cold Spring Harbor Laboratory Press Such promoters may be constitutively active or they may be active only temporarily. In one example the promoter may be regulated by an external signal, for example the promoter may be inducible or repressable.

The nucleic acid may be inserted into the cells by any useful method, for example by conventional recombinant techniques, such as any of the techniques described in Sambrook et al., Molecular Cloning: A Laboratory Manual, 1989, Cold Spring Harbor Laboratory, New York, USA In another embodiment the cells are primary cells. Primary cells are cells with a limited life span that preferably are derived from a mammalian tissue. Preferred primary cells are cells which are adherent. The mammalian tissue may for example be a human tissue, such as healthy or diseased tissue. In one embodiment the tissue is or comprises a neoplastic tissue, for example tissue removed from a cancer patient by surgery, for example from a patient suffering from melanoma, breast cancer or colon cancer. The tissue may also be hypertrophic cells, such as cardiac myocytes. Preferably said cancer patient has not been subjected to radiotherapy prior to surgery. In embodiments of the invention wherein the cells are primary cells it is preferred that the reporter system is endogenous to said primary cells.

Cell Attachment to Resin Beads and Cell Cultivation

The present invention relates to methods comprising the step of attaching cells comprising a reporter system(s) to resin beads. The cells may for example attach to said resin beads directly or by attaching a second compound conferring adhesion to the resin bead.

The resin beads useful for the present invention should preferably be able to support cell growth. The resin beads may per se be able to support cell growth, however frequently the resin beads will comprise a cell adhesion compound that enables the resin beads to support growth of cells. Said cell adhesion compound may be coupled to said resin beads by any useful means known to the person skilled in the art depending on the nature of the cell adhesion compound.

Any cell adhesion compound known to the person skilled in the art may be used with the present invention. It is frequently an advantage if the cell adhesion compound comprises at least one positively charged moiety at neutral pH, more preferably the cell adhesion compound has a positive overall netcharge at neutral pH.

In one preferred embodiment of the invention the cell adhesion compound comprises a peptide or a polypeptide, more preferably the cell adhesion compound consists of a peptide. Such peptides are herein also designated "adhesion peptides".

Said peptide preferably consists of in the range of 3 to 100, preferably in the range of 3 to 75, more preferably in the range of 3 to 50, even more preferably in the range of 3 to 30, yet more preferably in the range of 3 to 25, even more preferably in the range of 3 to 20, yet more preferably in the range of 3 to 15, such as in the range of 3 to 10, for example in the range of 3 to 8, for example in the range of 6 to 7 amino acids. In general, it is sufficient if the peptide comprises at least 3 amino acids.

It is preferred that the peptide comprises at least one amino acid selected from the group consisting of arginine and lysine, more preferably the peptide comprises at least 2 basic amino acids, such as 3 basic amino acids selected from the group consisting of Arg and Lys, even more preferably the peptide has an overall positive netcharge. In one preferred embodiment the peptide comprises the following sequence of 4 amino acids: basic-basic-lipophilic-basic. Basic amino acids may for example be selected from the group consisting of arginine and lysine, whereas the lipophilic amino acid may be selected from the group consisting of Gly, Ala, Val, Leu, Ile, Phe, Trp, Pro and Met of either D or L-form. Preferably, the peptide comprise at least 1, preferably at least 2, more preferably at least 3, even more preferably at least 4 amino acid on the D-form, yet more preferably all amino acids are on the D-form. Preferably D-amino acids are used to enhance the metabolic stability but also L-amino acids may be used.

Preferred examples of peptides useful as cell adhesion compounds are given in table 2 herein below:

TABLE 2

| No | 1 | 2 | 3 | 4 | 5 | 6 | 7 | SEQ ID NO |
|---|---|---|---|---|---|---|---|---|
| 1 | ala | arg | ile | arg | ile | gln | his | SEQ ID: 1 |
| 2 | ala | lys | cys | arg | trp | cys | met | SEQ ID: 2 |
| 3 | ala | lys | ala | arg | cys | lys | ser | SEQ ID: 3 |
| 4 | ala | lys | tyr | trp | ser | tyr | lys | SEQ ID: 4 |
| 5 | ala | his | leu | tyr | arg | asn | lys | SEQ ID: 5 |
| 6 | ala | arg | arg | cys | phe | arg | asp | SEQ ID: 6 |
| 7 | ala | ala | arg | his | cys | tyr | tyr | SEQ ID: 7 |
| 8 | ala | tyr | tyr | cys | gln | gln | arg | SEQ ID: 8 |
| 9 | ala | asp | leu | lys | arg | pro | met | SEQ ID: 9 |
| 10 | ala | gly | gly | lys | arg | lys | phe | SEQ ID: 10 |
| 11 | ala | pro | arg | lys | arg | cys | gly | SEQ ID: 11 |
| 12 | ala | thr | arg | arg | val | ala | arg | SEQ ID: 12 |
| 13 | ala | gly | lys | lys | asn | lys | asn | SEQ ID: 13 |
| 14 | ala | ala | lys | arg | trp | lys | phe | SEQ ID: 14 |
| 15 | ala | arg | trp | pro | tyr | arg | gly | SEQ ID: 15 |
| 16 | ala | leu | tyr | trp | thr | trp | arg | SEQ ID: 16 |
| 17 | ala | ala | tyr | arg | trp | tyr | arg | SEQ ID: 17 |
| 18 | ala | arg | cys | ile | arg | gly | asp | SEQ ID: 18 |
| 19 | ala | thr | lys | cys | lys | gly | arg | SEQ ID: 19 |
| 20 | ala | val | tyr | met | arg | asn | ile | SEQ ID: 20 |
| 21 | ala | arg | lys | arg | ile | arg | gln | SEQ ID: 21 |
| 22 | ala | lys | ile | arg | glu | lys | arg | SEQ ID: 22 |
| 23 | ala | arg | arg | phe | lys | met | tyr | SEQ ID: 23 |
| 24 | | arg | arg | phe | lys | | | SEQ ID: 24 |
| 25 | | arg | arg | ile | arg | | | SEQ ID: 25 |
| 26 | leu | arg | his | arg | Leu | lys | | SEQ ID: 26 |
| 27 | lys | phe | gly | gln | lys | (cys) | | SEQ ID: 27 |
| 28 | lys | val | tyr | met | his | lys | | SEQ ID: 28 |
| 29 | ile | arg | tyr | arg | leu | arg | | SEQ ID: 29 |
| 30 | ala | gln | arg | pro | arg | trp | | SEQ ID: 30 |
| | trp | tyr | ala | lys | arg | arg | | SEQ ID: 31 |
| | lys | arg | ile | arg | gln | arg | leu arg | SEQ ID: 32 |
| | lys | arg | ile | arg | gln | arg | lys | SEQ ID: 33 |
| | | arg | ile | arg | gln | arg | | SEQ ID: 34 |
| | | arg | gln | arg | ile | arg | | SEQ ID: 35 |

| No | 1 | 2 | 3 | 4 | 5 | 6 | 7 | SEQ ID NO |
|---|---|---|---|---|---|---|---|---|
| | lys | phe | gly | gln | lys | cys | | SEQ ID: 36 |
| | arg | arg | leu | leu | pro | ile | | SEQ ID: 37 |
| | pro | phe | arg | lys | lys | cys | | SEQ ID: 38 |
| | tyr | arg | trp | arg | ile | Ala | | SEQ ID: 39 |
| | arg | ser | lys | arg | ile | Asn | | SEQ ID: 40 |
| | arg | ser | ala | lys | arg | cys | | SEQ ID: 41 |
| | lys | lys | gln | phe | trp | Phe | | SEQ ID: 42 |
| | arg | met | lys | leu | his | lys | | SEQ ID: 43 |
| | arg | his | trp | gly | arg | ile | | SEQ ID: 44 |
| | thr | lys | arg | leu | lys | thr | | SEQ ID: 45 |

TABLE 2-continued

| | | | | | | | |
|---|---|---|---|---|---|---|---|
| thr | lys | gly | lys | ala | lys | | SEQ ID: 46 |
| ala | lys | thr | arg | his | arg | | SEQ ID: 47 |
| asn | arg | pro | arg | val | arg | | SEQ ID: 48 |
| val | pro | arg | lys | val | gln | | SEQ ID: 49 |
| lys | met | arg | tyr | cys | gln | | SEQ ID: 50 |
| ile | arg | lys | his | leu | ile | | SEQ ID: 51 |
| pro | arg | arg | val | val | ile | | SEQ ID: 52 |
| lys | arg | glu | ser | lys | arg | | SEQ ID: 53 |
| ser | arg | lys | asp | arg | lys | | SEQ ID: 54 |
| arg | cys | lys | lys | leu | ile | | SEQ ID: 55 |
| arg | lys | leu | arg | val | asn | | SEQ ID: 56 |
| val | arg | thr | val | arg | val | | SEQ ID: 57 |
| arg | ala | phe | lys | tyr | tyr | | SEQ ID: 58 |
| ile | thr | arg | arg | thr | gln | | SEQ ID: 59 |
| lys | met | pro | lys | lys | asn | | SEQ ID: 60 |
| lys | pro | lys | met | met | cys | | SEQ ID: 61 |
| lys | lys | met | arg | phe | trp | | SEQ ID: 62 |
| lys | lys | lys | phe | tyr | tyr | | SEQ ID: 63 |
| lys | ser | asn | lys | val | arg | | SEQ ID: 64 |
| lys | trp | pro | his | his | arg | | SEQ ID: 65 |
| arg | his | ile | gln | trp | tyr | | SEQ ID: 66 |
| leu | arg | leu | lys | pro | lys | | SEQ ID: 67 |
| glu | arg | lys | arg | cys | thr | | SEQ ID: 68 |
| arg | arg | ala | arg | gln | asp | | SEQ ID: 69 |
| arg | glu | lys | gly | ala | arg | | SEQ ID: 70 |

Furthermore, preferred peptide may be any of the peptides identified by any of SEQ ID: 1 to 70, preferably any of SEQ ID: 1 to 23 and 26 to 35, such as SEQ ID: 1 to 23, for example SEQ ID: 25 to 35, wherein 3 amino acids, preferably 2 amino acids, more preferably 1 amino acid have been substituted for another amino acid. Preferably, said substitution is a conservative substitution, i.e. substitution for an amino acid with similar characteristics. Said characteristic could for example be acidic/basic properties, polarity or lipophilicity. It is also comprised within the invention that the peptide may be a peptide of above mentioned size comprising any of the peptides identified by SEQ ID: 1 to 70. In particular, in order to immobilised the peptide on a resin bead it may be useful to synthesise the adhesion peptide on an amino acid immobilized on the resin bead, for example a Gly.

In one embodiment the peptide is preferably selected from the group consisting of peptides identified by SEQ ID: 21 to 23 and 36 to 35, more preferably from the group consisting of 26 to 35, even more preferably SEQ ID:35. In another embodiment the peptide defined by SEQ ID:21 is preferred.

In one embodiment of the invention it is preferred that the peptide has low or essentially no fluorescent properties. It is particularly preferred that the peptide has low or essentially no fluorescent properties when attached to a solid support, such as a resin bead. By "essentially no fluorescent properties" is meant that the peptide does not emit any detectable fluorescence. This is in particularly relevant for embodiments of the invention wherein the detectable output is fluorescence (see herein below). Preferred peptides to use with this embodiment of the invention may be selected from the group consisting of SEQ ID:26 to 35.

Peptides useful as cell adhesion compounds may be identified using any suitable method. Said method may for example include the steps of
i) synthesizing or coupling a test peptide on to a resin bead;
ii) incubating said resin bead with cells under cell cultivation conditions;
iii) testing whether said cells attach to said resin bead
iv) identification of the peptide sequence
wherein the test peptide is useful as cell adhesion compound If more cells attach to said resin bead in the presence, than in the absence of said test peptide. Preferably, the test peptide is useful as cell adhesion compound If at least 200, more preferably at least 500, even more preferably at least 1000 cells attach to said resin bead after incubation. This is in particular the case in embodiments of the invention, wherein the resin beads are PEGA beads. For example useful test peptides may be identified as described in example 1 herein below.

In embodiments of the invention wherein it is preferred that the peptide has no or low fluorescence it is preferred that the method comprises an additional step performed at any point subsequent to step i), such as immediately subsequent to step i) prior to step ii). Said additional step comprises testing whether said peptide has fluorescent properties. This may for example be performed by sorting resin beads in a FABS or manually with the aid of a fluorescence microscope. If this is done prior to step ii) then only resin beads with no or low fluorescence properties are incubated with cells, A non-limiting example of a useful method is described in example 2b.

The peptide may be coupled to the resin bead by any useful method, for example by synthesising the peptide directly onto an amino functionalised resin bead using a standard Fmoc-protocol for peptide synthesis. Other protective groups may be used instead of Fmoc, for example Boc. $N_3$ or Alloc. In one embodiment Alloc is the preferred protective group. It is preferred that different protecting groups are used for synthesis of the adhesion peptide or for library synthesis. The peptide may also be synthesised by anchoring an Fmoc amino acid to a hydroxyl functionalised resin bead, such as a hydroxymethylbenzoic acid (HMBA) derivatised PEGA resin followed by peptide assembly using standard Fmoc technology as described in B. Blankemeyer-Menge, M. Nimtz, and R. Frank, An Efficient method for anchoring Fmoc-amino acids to hydroxyl-functionalised solid supports. Tetrahedron Lett. 31:1701-1704, 1990 and A. Dryland and R. C. Sheppard. Peptide synthesis. Part 11. A system for continuous flow solid phase peptide synthesis using fluorenyl-methoxycarbonyl-amino acid pentafluorophenyl esters. *Tetrahedron* 44(3):859-876, 1988 Sidechains may be protected with acid labile protecting groups such as t-Bu, Trt, Pmc, Boc etc. The protected peptide may for example be cleaved off the resin using alkaline conditions or hydrazine and the structure may be determined e.g. by on bead Edman Degradtion. The HMBA-linked peptide may also be cleaved under mild alkaline condition.

In one embodiment the peptide may be linked to the resin bead via a linker, which may be a cleavable linker. This may for example be achieved by synthesizing the linker directly on resin beads or coupling the linker to the resin beads and subsequently coupling or synthesizing the library onto the resin beads. Thus, before coupling of the library the linker preferably comprises a protective group as described herein above. The cleavable linker may be any of the cleavable linkers described herein above. If the resin beads are coupled to the library via a cleavable linker it is preferred that the cleavable linker linking the adhesion compound is differentially cleavable.

In embodiments wherein cells adhere to the resin bead via the adhesion compound and the adhesion compound is attached to the resin bead via a cleavable linker, cells may be at least partially or even essentially fully released from the resin bead by cleavage of the cleavable linker.

Testing whether cells attach to resin beads may be done by any conventional methods, such as by manual inspection with the aid of a light microscope. If the cells have fluorescent properties, for example if the cells express a fluorescent protein, then resin beads with attached cells may be identified using a fluorescent microscope or a FABS, preferably a fluorescent microscope.

In one preferred embodiment of the invention, the cells may be cultivated directly on the resin beads. In general, a method of cultivating cells on resin beads may comprise the steps of Providing resin beads capable of supporting growth of cells
Seeding cells onto said resin bead
Incubating said resin beads comprising said cells in a cell culture medium under cell cultivation conditions
Optionally allowing said cells to divide on said resin bead
Thereby cultivating cells on resin beads The cells may adhere actively to the resin beads and will then generally be referred to as adherent cells.

Cells cultivation conditions depends on the specific cells. For a large number of mammalian cells, such conditions comprise high humidity, preferably close to 100%, approximately 5% $CO_2$ and around 37° C. It is often desirable to keep the resin beads immersed in a suitable cultivation medium and frequently it is also desirable that the resin beads can be circulated within said medium, for example by stirring or rotation. Said stirring or rotation may be continuous or in intervals. It is also possible that the container comprising the resin beads is simply rocked gently a few times every now and then.

In one embodiment of the invention more than one cell line or type of primary cell is attached to or cultivated on the beads. Hence for example 2, such as 3, for example 4, such as 5, for example 6, such as 7, for example 8, such as 9, for example 10, such as in the range of 10 to 20, for example in the range of 20 to 50, such as more than 50 different cell lines may be attached to or cultivated on said beads. Also different specific primary cells may be attached to the cultivated beads.

It is possible that a subgroup of resin beads only comprise one cell line or a specific kind of primary cells and another subgroup of resin beads comprises another cell line or another specific kind of primary cell and so forth. However, it is also possible that in principle every resin beads comprises all the different cell lines and/or different primary cells.

Intermediates between these two extremes may also be envisaged. Preferably, said different cell lines and/or primary cells comprise different reporter systems, hence it is possible that the different cell lines are derived from the same parent cell lined by insertion of different reporter systems. However, the different cell lines and/or primary cells may also be unrelated.

Cellular Molecules

In one particularly preferred embodiment of the invention the methods of the invention involve identification of compounds modulating a cellular response, which is mediated through an interaction between cellular molecules, more preferably through an interaction between intracellular molecules. Cellular molecules may be any cellular molecule, such as proteins, polypeptides, DNA, RNA, molecules of non-protein nature or metal-ions. In preferred embodiment, the cellular molecule is a protein or polypeptide. Intracellular molecules are molecules that are not accessible from the extracellular surface of intact cells. Intracellular molecules may for example be proteins, polypeptides, DNA. RNA, molecules of non-protein nature or metal-ions. In one preferred embodiment, intracellular molecules are proteins or polypeptides not accessible from the extracellular surface of intact cells.

In one embodiment, the cellular response is mediated through an interaction between cellular molecules of a cellular signal transduction pathway. Hence, the invention, for example may be useful for identifying compounds modulating the activity of a signal transduction pathway. Such compounds could for example activate or repress a signal transduction pathways by modulating the interaction between different or the same cellular molecules, modulating the catalytic activity of enzymes, modulating the synthesis or degradation of cellular molecules, modulating transcriptional activity, modulating the localization or movement of cellular molecules.

modulating the level of cellular molecules (i.e. in a specific cellular compartment or on average throughout the whole cell)

Within the context of the present invention the term "signal transduction pathway" should be understood in its common cell biological meaning, i.e. modulation of an intracellular event triggered by a cell surface receptor.

Signal transduction pathways may for example involve steps of changed catalytic activity of enzymes, phosphorylation, cleavage of proteins, synthesis of cAMP, activation of transcription, inhibition of transcription, change i intracellular $Ca^{2+}$ concentration, change in membrane potential, subcellular relocalisation of cellular components, complex formation of cellular components, degradation of cellular components and/or change in energy metabolism The signal transduction pathway could for example be a pathway activated/repressed by a cell surface receptor selected from the group consisting of G-protein coupled receptors (GPCR), protein kinase coupled receptors, receptor kinases with intrinsic kinase activity, orphan receptors or transmembrane channels. The signal transduction pathway may also be a pathway resulting in modulation of transcription, for example modulation of transcription regulated by a response element, for example a response element selected from the group consisting of CRE, SRE, TRE and AP-1 In one embodiment of the invention the signal transduction pathway is a pathway resulting in apoptosis.

Preferably the cellular molecules are proteins or parts thereof or derivatives thereof, more preferably the cellular molecules are proteins. Even more preferably the cellular molecules belong to the classes of: serine/threonine protein kinases; tyrosine protein kinases, protein phosphatases, phospholipid dependent serine/threonine protein kinases, calmodulin dependent serine/threonine protein kinases, mitogenactivated serine/threonine protein kinases, cycline dependent serine/threonine protein kinases, transcription factors, structural proteins, protein scaffolds, proteases, such as caspases, metallo-matrix-proteases, rennin, cathepsins, viral proteases, secretases or ADAM family proteases, or hydrolases, nucleases, synthases, isomerases, polymerises, oxidoreductases, ATPases or GTPases.

The cellular molecules are more preferably proteins that are known to participate in protein-protein interactions or complex formations. Such proteins can be selected from proteins listed in databases like BIND (Biomolecular Interaction Network Database) http://bind.ca.

In one embodiment of the invention the cellular molecules are involved in regulation of apoptosis. Thus the cellular molecules may be proteins or functional fragments thereof involved in regulation of apoptosis. Proteins involved in apoptosis includes for example caspases, inhibitors of apoptosis (IAPs) or Smac. Inhibitors of apoptosis may for example be XIAP, cIAP1/BIRC2, ML-IAP/BIRC7, DIAP1, DIAP2, OPIAP3, cIAP2, NAIP, Apollon or Survivin (see also Vaux and Silke, 2005, Nature Reviews, 6:287-297). Thus, in one example proteins involved in protein-protein interaction may be Smac and XIAP or ML-IAP or a Smac binding fragment thereof. Smac binding fragments of XIAP preferably comprises the BIR3 domain of XIAP, whereas Smac binding fragments of ML-IAP preferably comprises the BIR domain. The domain structure of IAPs is well described, see for example Wu, G., Chai, J., Suber, T. L., Wu, J.-W., Du, C., Wang, X., and Shi, Y. (2000) Nature 408, 1008-1012; Matthew C. Franklin et al., *Biochemistry* 2003, 42, 8223-8231; and Liston et al. Oncogene. 2003 Nov. 24; 22(53):8568-80

A cell surface receptor within the meaning of the present invention is preferably a protein, more preferably a protein that is accessible from the extracellular surface. Yet more preferably, the cell surface molecule is a cell surface protein receptor (herein also merely designated "receptor"). A "receptor" within the meaning of the present invention, is a molecule, which at least sometimes is localised at the cell surface and which is capable or associating with at least one ligand. The ligand binding site is accessible from the extracellular surface. Frequently, association with said ligand may alter the activity of the receptor.

Cellular Response

The invention relates to methods of identifying compounds modulating, such as activating or inhibiting, a cellular response linked to a reporter system. The reporter system may be any of the reporter systems described herein below. The methods disclosed by the present invention may be used to identify compounds modifying any cellular response, which is or may be linked to a reporter system generating a detectable output. The person skilled in the art will appreciate that the specific methods disclosed herein may be adapted to any such cellular response. Below, non-limiting examples of cellular responses are described.

In a particularly preferred embodiment of the invention, the cellular response is mediated through interaction between cellular molecules, such as intracellular molecules. The cellular molecules may for example be components of a signal transduction pathway, and thus the cellular response may be activation or repression of a signal transduction pathway. Hence, the cellular response may for example be modulation of a signal transduction pathway within a cell, such as modulation of a signal transduction pathway mediated by a cell surface molecule. By "activation of a receptor" is meant that the receptor is influenced in a manner that it activates downstream signalling events. Accordingly, the methods according to the present invention may be employed to identify activators or inhibitors of signal transduction pathways.

Examples of modulations of signal transduction pathway includes:

Upregulation or downregulation of the level of a member of the pathway

Relocalisation of a member of the pathway

Complex formation between members of the pathway or between members of the pathway with other cellular compounds Enhanced or reduced transcription from genes regulated by the pathway Modification by for example phosphorylation of a member of the pathway Activation or inhibition of an enzyme of the pathway Degradation of a cellular compounds due to upregulation or downregulation of the pathway Altered secretion of a compound Change in ion-flux Morphological changes Change in viability In a preferred embodiment the modulation of a signal transduction pathway can for example be monitored by measuring:
- the enzymatic activity of an enzyme being part of said signal transduction pathway
- the level of cyclic nucleotides, i.e. cAMP or cGMP
- the activity of transcription factors
- the level of specific proteins as quantified through standard proteomics techniques
- the level of inositol or lipid phosphates
- the level of phosphorylation of specific proteins as quantified through standard proteomics techniques
- the binding between two or more proteins or polypeptides
- the cellular localization of proteins or polypeptides The enzymatic activity could for example be the enzymatic activity of serine/threonine protein kinases or of tyrosine protein kinases or of protein phosphatases or of phospholipid dependent serine/threonine protein kinases or of calmodulin dependent serine/threonine protein kinases or of mitogenactivated serine/threonine protein kinases or of cycline dependent serine/threonine protein kinases or of proteases or of hydrolases or of nucleases or of synthases or of isomerases or of polymerises or of oxido-reductases or of ATPases or of GTPases.

The cellular response may in one embodiment be modulation of transcriptional activity, such as activation or reduction of transcription of one or more genes. In particular, activation or reduction of transcription of genes regulated by a response element. Said response element could for example be selected from the group consisting of CRE, SRE, TRE and AP-1.

Hence, the cellular response may also be an increased or decreased level of a particular mRNA within a cell.

By the term "regulated by a response element" is meant that transcription is modulated by said response element, however other elements may also modulate transcription of said gene. By the term "activation of response element" is meant increased transcription of genes regulated by said response element.

In another embodiment of the invention the cellular response is:
- change in the intracellular level of a compound; or
- change in the level of a compound within a specific cellular compartment, for example within the cytoplasm, in the golgi, in the endoplasmatic reticulum, in lysosomes, in endosomes or in the nucleus The compound may be any compound, preferably a naturally occurring compound. Frequently, the compound is a compound endogenous to the cell. The compound may thus for example be a salt, an ion, a nucleotide or a derivative thereof, a peptide, a saccharide, a lipid or a biomacromolecule. Biomacromolecules includes for example RNA such as mRNA, polypeptides and proteins. An example of an ion is $Ca^{2+}$ and an example of a nucleotide derivative is cAMP.

In yet another embodiment of the invention the cellular response is relocalisation of a compound. Relocalisation may for example be
- concentration of a compound otherwise dispersed in one or more specific locations
- relocalisation from one cellular compartment to another, for example relocalisation from the cellular membrane to the cytoplasma.
- relocalisation from one location within a compartment to another location within the same compartment
- internalisation of an extracellular compound The compound may be any compound, such as any of the compounds mentioned in the section above. In one preferred embodiment the compound, which is relocalised is a biomacromolecule, such as RNA, polypeptides or proteins. For example, the compound may be a cell surface receptor (receptor). The cellular response may thus be internalisation of said receptor or relocalisation of said receptor from the cellular membrane to the cytoplasma.

In one embodiment of the invention the cellular response is change in the activity of a compound, such as an increase or a decrease in the activity of a compound. Said compound may for example be an enzyme. The cellular response may for example be induction of the activity of a caspase. Preferred caspases are Caspase 3 or 7.

In another embodiment of the invention the cellular response is change in phosphorylation of a compound.

In another embodiment of the invention the cellular response is formation or disruption of a complex between compounds.

In another embodiment of the invention the cellular response is change in the concentration of a compound.

The cellular response may also be altered secretion of a compound, such as increased or decreased secretion of a compound. Said compound could for example be a biomacromolecule, such as a protein, a polypeptide, a peptide, a hormone, a cytokine, or the like.

In another embodiment of the invention the cellular response is change in pH in an intracellular compartment, for example in the cytoplasm.

In yet another embodiment the cellular response is a change in a membrane potential, for example a change in membrane potential over the cell membrane or over the mitochondria membrane.

In an even further embodiment of the invention the cellular response is change in morphology, such as change in size or shape. The cellular response may also be change in viability (e.g. apoptosis or necrosis), such as change in viability under specific conditions.

In a preferred embodiment of the present invention the cellular response is change in interaction between two or more cellular molecules, preferably between two cellular molecules, such as establishment of an interaction between two or more cellular molecules or disruption of an interaction between two or more cellular molecules. Thus the cellular response may be formation of a complex or disruption of a complex. The cellular molecules may be any of the cellular molecules mentioned above, however, preferably the cellular molecules are proteins or fragments thereof.

In one embodiment of the present invention the cellular response is induction or facilitation of apoptosis in living cells, such as induction or facilitation of apoptosis in tumour cells, preferably induction of apoptosis. The cellular response may also be induction or facilitation of apoptosis in cells that have undergone an apoptosis promoting treatment. The cellular response may also be induction or facilitation of apoptosis in cells that have undergone an apoptosis inhibiting treatment, In another embodiment of the invention the cellular response is inhibition or reduction of apoptosis, for example reduction of apoptosis in cells prone to undergo apoptosis or reduction in apoptosis in cells that have undergone an apoptosis promoting treatment.

The apoptosis promoting treatment may be contacting cells with an inducer of apoptosis. The inducer of apoptosis may be any compound known to be capable of inducing apoptosis, for example the compound may be staurosporine (STS). Alternatively, the apoptosis promoting treatment may be illumination with radiation, such as with UV-light with a predetermined wave length and intensity.

The methods according to the invention may also include identification of compounds modulating more than one cellular response, such as 2, for example 3, such as 4, for example 5, such as more than 5 different cellular responses. Said cellular responses may be any of the responses discussed above.

Reporter System

The reporter system to be used with the present invention should be selected according to the particular cellular response. The reporter system should be capable of generating a detectable output.

In some embodiments of the invention the reporter system may be identical to the cellular response. This is in particular true when the cellular response may be detected without the aid of an additional reporter system, for example when the cellular response is an increase/decrease in the level of a compound, relocalisation of a compound, change in membrane potential, change in pH, change in morphology or the like.

Hence, the reporter system may be a system endogenous to said cells. For example, the reporter system may comprise the endogenous system regulating the intracellular level of an endogenous compound. By way of example, the reporter system may be the endogenous system of a cell regulating the intracellular $Ca^{2+}$ level.

In another example, the reporter system comprises the intracellular localisation of an endogenous compound.

In yet another example, the reporter system may comprise the activity of an enzyme. This may in particular be relevant when the cellular response is modulation of an enzymatic activity or modulation of a signal transduction pathway which modulates an enzymatic activity. Then the reporter system could be direct detection of for example the enzymatic activity of serine/threonine protein kinases or of tyrosine protein kinases or of protein phosphatases or of phospholipid dependent serine/threonine protein kinases or of calmodulin dependent serine/threonine protein kinases or of mitogenactivated serine/threonine protein kinases or of cycline dependent serine/threonine protein kinases or of proteases, such as caspases, metallo-matrix-proteases, rennin, cathepsins, viral proteases, secretases or ADAM family proteases or of hydrolases or of nucleases or of synthases or of isomerases or of polymerises or of oxido-reductases or of ATPases or of GTPases.

It is preferred that said enzymatic activity may be detected for example because the enzymatic activity leads to formation of a coloured compound, a fluorescent compound, a radioactive compound or the like. This may be achieve by the use of appropriate substrates. If the enzyme is a protease, the enzymatic activity may for example be detected by use of a substrate, which generates a detectable output when cleaved by said protease. For example the substrate could be a peptide or a polypeptide comprising a fluorescent moeity and a quencher, wherein cleavage would lead to formation of two peptides/polypeptides, wherein one comprises the fluorescent moeity and the other comprises the quencher. Fluorescence would thus be detectable only in the presence of an active protease.

In embodiments wherein the enzyme is a caspase, the reporter system may be a substrate for said caspase. Useful caspase substrates are known to the skilled person and several caspase substrates are commercially available, for example from Beckman Coulter Inc. Examples of Caspase substrates are Caspase 3 and/or 7 substrates. It is preferred that cleavage of the substrates is readily detectable. Thus fluorogenic substrates comprising a quenching group which may be cleaved of by caspases may be useful. Cleavage of such substrate can simply be detected by determining fluorescence. Non-limiting examples of fluorogenic caspase substrates are the Cell-Probe HT Caspase 3/7 Whole Cell Assay, Beckman Coulter, Inc, or any of the substrates described in U.S. Pat. No. 6,342,611. It is not required that such a reporter system is introduced permanently into living cells. Thus the substrate may be added directly to the cell culture medium or to an assay buffer comprising resin beads with cells. Thus such a reporter system may also be useful in embodiments of the invention wherein primary cells are employed. A non-limiting example of a useful Caspase assay is given in example 12 herein below.

However, the reporter system may also be heterologous to the cell, i.e. a reporter system which has been inserted into the cell for example by recombinant techniques.

In several embodiments of the invention the reporter system comprises a fusion protein comprising a first protein and detectable polypeptide. The detectable polypeptide may for example be an enzyme or part thereof, a transcription factor or part thereof or a bioluminiscent protein, such as a fluorescent protein. Preferred detectable polypeptides are luciferase or fluorescent proteins. The first protein may be selected according to the cellular response. If the cellular response is change in level or location of a given protein, the first protein could be that particular protein. If the cellular response is change in interaction between two or more proteins, the first protein could be one of the proteins taking part in that interaction.

In embodiments of the invention, wherein the cellular response is modulation of transcription from gene(s) regulated by a response element, it is preferred that the report system comprises a nucleic acid comprising a nucleotide sequence encoding a detectable polypeptide operably linked to a response element, the activity of which is modulated by the cellular response.

In embodiments of the invention, wherein the cellular response is modulation of a signal transduction pathway, the reporter system may comprises a nucleic acid comprising a nucleotide sequence encoding a detectable polypeptide operably linked to a response element, the activity of which is modulated by said signal transduction pathway.

For example, if the cellular response is modulation of a signal transduction pathway influencing the activity of CRE and/or SRE, then the reporter system may comprise a nucleic acid comprising a nucleotide sequence encoding a detectable polypeptide operably linked to a response element selected from the group consisting of cAMP response element (CRE) and serum response element (SRE). Examples of such signal transduction pathways include the signal transduction pathways modulated by GPCR of the rhodopsin family or secretin family and by protein kinase receptors and receptors belonging to the family of receptor kinases.

By way of example: 1) If the cellular response is activation of a signal transduction pathway activated by a GPCR coupled to a $G_S$ (see herein above) that stimulates adenylate cyclase, then the reporter system may be a nucleic acid comprising a nucleotide sequence encoding a detectable polypeptide operably linked to CRE. Activation of said GPCR may then be detected by detection of increased levels of said detectable polypeptide. 2) If the cellular response is activation of signal transduction pathway activated by a GPCR coupled to a $G_I$ (see herein above) that inhibits adenylate cyclase, then the reporter system may be a nucleic acid comprising a nucleotide sequence encoding a detectable polypeptide operably linked to CRE. Activation of said GPCR may then be detected by detection of decreased levels of said detectable polypeptide.

Similarly, if the cellular response is modulation of a signal transduction pathway that influences the activity of TRE, then the reporter system may comprise a nucleic acid comprising a nucleotide sequence encoding a detectable polypeptide operably linked to TPA response element (TRE). Examples are GPCRs that are linked to activation of Protein Kinase C such as Gq coupled receptors (see herein above).

Similarly, if the cellular response is modulation of a signal transduction pathway that influences the activity of SRE, then the reporter system may comprise a nucleic acid comprising a nucleotide sequence encoding a detectable polypeptide operably linked to SRE. Examples of such signal transduction pathways include the signal transduction pathways modulated by growth hormones or cytokines through protein kinase receptors and receptors belonging to the family of receptor kinases.

Similarly, if the cellular response is modulation of a signal transduction pathway that influences the activity of AP-1, then the reporter system may comprise a nucleic acid comprising a nucleotide sequence encoding a detectable polypeptide operably linked to AP-1. Examples of such signal transduction pathways include the signal transduction pathways modulated by cytokines or growth factors cytokines through protein kinase receptors and receptors belonging to the family of receptor kinases The detectable polypeptide may be any detectable polypeptide, however preferably the detectable polypeptide is selected from the group consisting of fluorescent proteins and enzymes.

Fluorescent proteins may for example be green fluorescent protein (GFP) and fluorescent mutants thereof, such as yellow fluorescent protein (YFP) or cyan fluorescent protein (CFP). The fluorescent protein can also be a protein complex, e.g. a di- or tetramer of a fluorescent protein, such as dsRed. Enzymes may for example be selected from the group consisting of luciferase, CAT, galactosidase, alkaline phosphatase and beta-lactamase.

In one embodiment of the invention the reporter system may comprise a bioluminescent moiety. For example, if the cellular response is relocalisation of a compound, then the reporter system may for example be said compound linked to a luminescent moiety, such as a fluorescent moiety. Hence, for example if the cellular response is relocalisation of a polypeptide the reporter system may be a chimeric protein made up of said polypeptide and a fluorescent protein, such as GFP, YFP or CFP. In one preferred embodiment said polypeptide may be receptor.

In one embodiment of the invention the reporter system may detect the level of a cellular molecule, such as a protein. This may for example be achieved by quantifying the amount of a compound i.e. an antibody that specifically binds to the cellular molecule. The quantification can for example be achieved by covalently coupling a fluorescent, bioluminescent or coloured moiety to said compound. The quantification could be confined to a specific cellular compartment.

In one embodiment of the invention the reporter system may detect the level of modification of a cellular molecule for example but not limited to phosphorylation, glycosylation or ubiquitination. This may for example be achieved by quantifying the amount of a compound i.e. an antibody that specifically binds to the modified cellular molecule. The quantification can for example be achieved by covalently coupling a fluorescent, bioluminescent or coloured moiety to said compound. The quantification could be confined to a specific cellular compartment.

In one embodiment of the invention the reporter system may detect complex formation or disruption between two cellular proteins (designated first protein and second protein in this paragraph). This is in particular relevant when the cellular response is change in interaction between two cellular proteins. Several different reporter systems may be used to detect interaction between a first and a second protein. Below preferred reporter systems are described, however, the invention is not limited to these specific reporter systems.

The reporter system may for example comprise the first protein linked to a bioluminescent moiety, such as luciferase and the other protein linked to a fluorescent moiety, such as a fluorescent protein. Such reporter systems are referred to as "BRET reporter systems" herein. The bioluminescent moiety should preferably be able to directly or indirectly generate light of a wavelength capable of exciting the fluorescent moiety. The skilled person will readily be able to select useful bioluminescent moeities and fluorescent moeities. Preferably, the BRET reporter system comprises a first chimeric protein comprising the first protein linked to a bioluminescent protein, preferably luciferase and a second chimeric protein comprising the second protein linked to a fluorescent protein. Such a reporter system may be introduced into a cell by introducing nucleic acids encoding the first and the second chimeric proteins under control of suitable promoters into said cell. Direct interaction between the proteins can after expression of the two chimeric proteins be detected through occurrence of BRET (Bioluminescence Resonance Energy Transfer). In one embodiment, BRET2 technology may be used which is based on energy transfer between a bioluminescent donor (a Renilla luciferase (Rluc) fusion protein) and a fluorescent acceptor (a Green Fluorescent Protein (GFP2) fusion protein). In presence of its substrate DeepBlueC™ (a coelenterazine derivative). Rluc emits blue light (~395 nm). Thus the reporter system may comprise a first chimeric protein comprising the first protein and Rluc and a second chimeric protein comprising the second protein and GFP2. A protein-protein interaction between Rluc and GFP2 chimeric proteins allows energy transfer to GFP2, which reemits green light (510 nm). Expression of Rluc alone, in the presence of the substrate DeepBlueC™, gives an emission spectrum with a peak at ~395 nm, whereas when the Rluc and GFP2 chimeric proteins interact, there is efficient energy transfer between Rluc and GFP2 and the 510 nm signal represents a major peak.

In another similar reporter system the first protein and the second protein are linked to different fluorescent moieties, preferably a fluorescent proteins. Such reporter systems are referred to as "FRET reporter systems" herein. Preferably, one fluorescent moiety is capable of emitting light of a wavelength capable of exciting the other fluorescent moeity. FRET reporter systems preferably comprise a first chimeric protein comprising the first protein and a fluorescent protein and a second chimeric protein comprising the second protein and another fluorescent protein. It is then possible to detect the complex formation through the occurrence of FRET (Fluorescence Resonance Energy Transfer). BRET or FRET according to the present invention may for example be performed as described in (Nicolas B, R Jockers, and T Issad *Trends in Pharmacological Sciences* 23 (8):351-354, 2002; and/or A. Roda, M. Guardigli, P. Pasini, and M. Mirasoli. *Anal. Bioanal. Chem* 377 (5):826-833, 2003)

Complex formation may also be detected by proximity ligation. In such an embodiment the reporter system comprises two affinity probes raised against the first and the second protein. Such reporter systems are designated "proximity ligation reporter systems" herein. When the two proteins come in close proximity a ligation reaction creates a DNA reporter sequence that can be amplified. The amplified sequence can be detected by any useful method, for example it may be detected through photolabelling. Preferably, the DNA reporter sequence is amplified by PCR, rolling circle replication or ligation chain reaction. In order to detect the amplified sequence, the sequence may for example be amplified using primers labelled with a detectable label, such as a fluorescent label or the sequence may be detected using a detectably labelled probe, such as a fluorescently labelled probe. The affinity probes in general comprise or consist of a binding moeity and a nucleic acid moeity. The binding moiety of the affinity probes can be any molecule that binds either the first or the second protein with high affinity. Preferably, the binding moeity is capable of specifically recognising and binding either the first or the second protein. Examples of useful binding moieties of affinity probes are monoclonal- or polyclonal antibodies or antigen binding fragments thereof, chimeric antibodies, recombinant antibodies, single chain antibodies or aptamers. Antibodies may be prepared using any conventional method known to the person skilled in the art. Aptamers may be prepared by any method known to the skilled person, for example by iterative cycles of screening nucleic acid libraries for compounds capable of binding a tare nucleic acid molecules selected for their ability to specifically bind a target. Aptamers may for example be produced using a SELEX process (Sun S Curr Opin Mol Ther 2000 Feb. 2:100-5; Jayasena S D Clin Chem 1999 September 45:1628-50). The nucleic acid moeity may comprise or consist of any nucleic acid sequence, preferably a sequence, which when ligated to another nucleic acid moeity creates a DNA reporter sequence, which can be amplified by PCR, rolling cycle amplification or ligase chain reaction using appropriate primers. A person skilled in the art can design useful nucleic acid moeity sequences and corresponding primers. The affinity probes can be introduced into cells by a number of different methods, for example they may be introduced into the cells after said cells have been fixed and permeabilized or they can be introduced by using traditional cDNA transfection methods, for example by using standard procedure for Fugene6 transfection. Proximity ligation may for example be carried out as described in Frederiksson et al. Nature Biotechnology 2002, 20: 473; Gullberg et al. Curr Opinion Biotechnology 2003, 14: 82. The reporter system may also be a "two-hybrid reporter system". Two-hybrid reporter systems comprises two chimeric proteins, wherein the first chimeric protein comprises the first protein fused to a DNA binding domain and the second chimeric protein comprises the second protein fused to a transactivating domain. Furthermore, the two hybrid reporter system comprises a reporter construct comprising a nucleic acid sequence encoding a detectable polypeptide the expression of which is controlled by the transactivating/DNA binding domain. Thus if the first protein interacts with the second protein the DNA binding domain and the transactivating domain are brought into close proximity and may activate transcription from the reporter construct. Interaction can then be determined by detection of the detectable polypeptide. The detectable polypeptide may be any of the detectable polypeptides mentioned herein above. Two-hybrid reporter systems are well described in the art, see for example U.S. Pat. No. 5,283,173.

The reporter system may also be an enzyme complementation reporter system. Enzyme complementation reporter systems comprises two chimeric proteins, wherein the first chimeric protein comprises the first protein fused to a first part of an enzyme and the second chimeric protein comprises the second protein fused to a second part of an enzyme. The first and the second part of an enzyme should together constitute a functional enzyme. Thus, when the first protein interacts with the second protein the first part and the second part of an enzyme will form a functional enzyme, the activity of which may be determined.

One example of an enzyme useful for enzyme complementation system is DHFR (dihydrofolate reductase), where the activity of the reconstituted enzyme is monitored as a fluorescent read-out based on stoichiometric binding of fluorescein-methotrexate to reconstituted DHFR (Remy I, Michnick S W Proc Natl Acad Sci USA 1999 May 96:5394-9).

Hence, if the cellular response is relocalisation of a cell surface molecule, then the reporter system may comprise a fluorescent moiety covalently coupled to said cell surface molecule.

In some embodiments of the invention the cellular response is modulation of a signal transduction pathway involving activation of phospholipase C. Phospholipase C may for example be activated by GPCRs coupled to $G_Q$ (see herein above). Activation of phospholipase C in general leads to increase in the intracellular level of $Ca^{2+}$ and thus in such embodiments the reporter system may be the intracellular $Ca^{2+}$ level. This reporter system may thus be endogenous to the cell.

When the cellular response is induction/facilitation of apoptosis a number of reporter systems may be employed. Induction/facilitation of apoptosis may be determined by determining caspase activity as described herein above. Induction/facilitation of apoptosis may also be determined by determining cell growth/number of cells, for example cell growth/number of cells after cultivation of for example normal cells or tumour cells, such as cells expressing high levels of XIAP or ML-IAP. Other methods of determining apoptosis are well known to the skilled person.

Detectable Output

The detectable output may be any output, which is detectable directly or indirectly. For example the detectable output may be the concentration of a compound within a cell, localisation of a compound within a cell, luminiscense, activity of an enzyme or the like.

In preferred embodiments of the invention the detectable output is luminiscense, fluorescence, bioluminescence, FRET or BRET. Bioluminiscence may be detected by any conventional methods, for example with the aid of a Plate reader. BRET or FRET may for example be detected using FABS, a plate reader, a fluorescence microscope or the like.

Alternatively, the detectable output may preferably be linked (directly or indirectly) to a bioluminescent signal.

However, the detectable output could also be radioactivity, a coloured compound or a colour signal, a heavy metal, an electrical potential, a redox potential, a temperature or the detectable output may be linked to a radioactive signal, a coloured compound or a colour signal or a heavy metal or an electrical potential, or a redox potential or a temperature. Said radioactive signal could for example be $^{35}S$, $^{32}P$, $^{3}H$. The coloured compound could for example be the product of any of the enzymatic reaction described herein elsewhere. The heavy metal could for example be gold.

In embodiments of the invention, wherein the cellular response is change in the intracellular level of a compound or change in the level of a compound within a specific cellular compartment, then the detectable output may be said level of said compound. Depending on the nature of the compound, said level may be detected directly or indirectly.

If the compound for example is a fluorescent compound, the level of said compound may be determined by determining the fluorescence properties. This may be done by any suitable means, for example by the aid of a fluorescence microscope, a FACS (Fluorescence Activated Cell Sorter), a FABS (Fluorescence Activated Bead Sorter), fluorescence plate-reader or a fluorescence spectrometer, If the compound for example is an enzyme then the level of said compound may be determined by determining the activity of said enzyme. By way of example, if the enzyme catalyses a reaction leading to a product, which is directly detectable, for example by colorimetric or chemiluminescent detection techniques, the activity of said enzyme may be detected by detecting said compound. For example, if the enzyme is luciferase, the activity of said enzyme may be detected by detecting emission of light upon oxidation of the added substrate, luciferin.

Several other enzymes such as CAT, β-galactosidase, alkaline phosphatase, horseradish peroxidase and beta-lactamase are, when provided with suitable substrates, capable of catalysing reactions leading to coloured or chemiluminescent products, which may be detected using any colorimetric or chemiluminescent detection technique.

If the compound for example is $Ca^{2+}$, then the intracellular concentration of said ion can be measured by using any suitable method, for example by inserting into the cells $Ca^{2+}$ binding fluorescent compounds like Fura-2, Fluo-3 or Fluo-4 (Molecular Probes), which change fluorescent properties according to a changed $Ca^{2+}$ concentration. A non-limiting example of a method of determining cytosolic free $Ca^{2+}$ is given in example 13 herein below. Other ion concentrations can be monitored using suitable fluorescent compounds, which for example are available from Molecular Probes Inc.

If the compound for example is a protein, then it may for example be detected using a first specific binding partner. Said first specific binding partner could be a second protein capable of specifically interacting with said protein, such as a specific antibody or said first specific binding partner could be an aptamer. Said first specific binding partner could be conjugated to a directly detectable compound, such as a fluorescent compound, a radioactive compound or a heavy metal or to an indirectly detectable compound, such as an enzyme, which for example could be any of the enzymes mentioned herein above. It is also possible that the first specific binding partner may be detected with a second specific binding partner, capable of interacting specifically with the first specific binding partner. Said second specific binding partner may be conjugated to a directly or indirectly detectable compound similarly to the first specific binding partner. Additional specific binding partners may be used.

In embodiments of the invention wherein the cellular response is relocalisation of a compound the detectable output could be a detectable label conjugated to said compound. In particular, the compound may be conjugated to a directly detectable label, such as a fluorescent label or a heavy metal. Thus the localisation of the compound may be directly detected, for example using a fluorescence microscope. Fluorescent plate-reader, fluorescence spectrometer, a FACS or a FABS instrument In one preferred embodiment the compound is a fusion protein comprising a protein of interest and a fluorescent protein, such as GFP. The compound may thus be a fluorescent probe. Thus the detectable output may be localisation of a fluorescent signal. Alternatively, the compound is a fusion protein comprising the protein of interest and a tag. Said tag could be a tag specifically interacting with a specific binding partner, for example the tag could be an HA-tag or a flash domain. Alternatively, localisation of a compound may be determined with the aid of a specific binding partner as outlined above. Intracellular localisation may also be detected using methods capable of detecting distance between two compounds, for example BRET or FRET.

In embodiments of the invention wherein the cellular response is change of activity of a compound, the detectable output may be a product of said activity. I.e. when said compound is an enzyme the detectable output could be a product of a reaction catalysed by said enzyme. Said product could thus be a coloured product or a chemiluminiscent product as discussed herein above.

In embodiments of the invention wherein the cellular response is enhanced or reduced transcription from one or more genes, then the cellular response could be mRNA transcribed from said gene, a protein encoded by said gene or in case the protein is an enzyme, the detectable output could be a product of a reaction catalysed by said enzyme. The enzyme and the products could be any of the enzymes or products discussed herein above.

mRNA may be detected by any useful means, for example with the aid of a probe capable of hybridising specifically with said mRNA. Said probe could be labelled with a directly detectable label, for example a radioactive compound, a fluorescent compound or a heavy metal or an indirectly detectable label such as an enzyme or a specific binding partner.

Said protein may be detected with the aid of specific binding partners as outlined herein above. However, in a preferred embodiment the protein is a fluorescent protein and may thus be detected directly. Hence, the detectable output could be bioluminescence, such as fluorescence.

In embodiments of the invention wherein the cellular response is modification by for example phosphorylation of a compound this can be detected through binding of an antibody that specifically bind the phosphorylated protein said antibody can then be quantified by specific fluorescence labelling.

In embodiments of the invention wherein the cellular response is change in pH in an intracellular compartment, the detectable output will in general be said pH. The pH may be determined using any suitable method, for example using a pH indicator or a pH-meter. For example the pH may be determined using a fluorescent indicator for intracellular pH. Suitable compounds are compounds with a fluorescent excitation profile which is pH-dependent, such as BCECF (available from Molecular Probes).

In embodiments of the invention wherein the cellular response is a change in a membrane potential, the detectable output will in general be said membrane potential. The membrane potential may be determined using any suitable method such as applying a fluorescent molecule to cells that distribute over the membrane dependent upon the membrane potential. Examples of such compounds are DiBAC, various ANEP dyes, JC-1 and JC-9 (Molecular Probes). For example, JC-1 and JC-9 are cationic dyes that exhibit potential-dependent accumulation in mitochondria leading to a shift in fluorescence emission from green to red. Thus mitochondrial depolarization may for example be determined by decrease in red/green fluorescence intensity ratio (see also product information from Molecular Probes). ANEP dyes are in particularly useful for detection of changes in membrane potential. The fluorescence can be read for instance by a fluorescence microscope, a fluorescence plate-reader, a FACS, or a FABS instrument.

In embodiment of the invention wherein the cellular response is change in morphology, the detectable output will in general be the morphology of the cell. The morphology may be observed using any suitable method for example by the aid of a microscope, using a FACS or FABS.

In embodiments of the invention where the cellular response is change in an interaction between two cellular proteins, the detectable outout may for example be BRET or FRET, which is detectable by determining the occurrence of fluorescence of a given wavelength. BRET or FRET may for example be detected using a FABS. FACS, fluorescent microscope or any other equipment useful for detection of fluorescence.

In embodiments of the invention wherein the reporter system is proximity ligation the detectable output is dependent on the detectable label used to label the amplified DNA reporter sequence. In embodiments, wherein the DNA reporter sequence is amplified using fluorescently labelled primers, the detectable output will be said fluorescent label, which may be detected using a FABS. FACS, fluorescent microscope or any other equipment useful for detection of fluorescence.

Depending on the detectable output, it will frequently be an advantage to fix cells prior to detecting said detectable output. However, in some embodiments of the invention it is preferred that the cells are not fixed. Cells may be fixed according to any useful protocol (see also definitions herein above)

Selection

The methods according to the invention involves screening resin beads for beads comprising cells meeting at least one predetermined selection criterion, wherein said selection criterion is linked directly or indirectly to said detectable output. Hence, the selection criterion will be dependent on the detectable output.

For example the predetermined selection criterium may be a quantitative criterium, such as a quantitative level of bioluminescence above or below a specific threshold value.

In embodiments of the invention, wherein the detectable output is fluorescence or the detectable output may be linked to a fluorescent signal, then the predetermined selection criterion could be any fluorescence property. For example, the selection criterion could be intensity of said fluorescence above or below a predetermined threshold value or emission of light of a specific wavelength or absorption of light of a specific wavelength or intensity of emitted light of a specific wavelength above or below a predetermined threshold value. The selection criterion could also be based on Fluorescence lifetime and/or fluorescence polarization The selection criterion could also be a specific localisation of the fluorescent signal, such as intensity of a fluorescent signal in a specific cellular compartment above or below a predetermined threshold value. The selection criterion could also be a predetermined change in fluorescence lifetime or in fluorescence polarization. Fluorescence intensity and/or localisation may for example be determined using image processing and/or image analysis, a fluorescence microscope, FACS, FABS or fluorescence plate reader.

In one embodiment of the invention the selection criterion is high fluorescence intensity. This may for example be the case, when the cellular response is activation of a signal transduction pathway and the reporter system comprises a gene encoding a fluorescent protein, where activation of the signal transduction pathway leads to increased expression of said gene. This may also be the case when the cellular response is establishment of interaction between two cellular proteins, wherein the reporter system is a FRET or BRET reporter system. After release of a proportion of the library members to be tested, resin beads may be selected using a method comprising the steps of:

1. Determining the fluorescence intensity of positive control resin beads and setting this fluorescence intensity to 100%
2. Determining the fluorescence intensity of negative control resin beads and setting this fluorescence intensity to 0%
3. Selecting resin beads having a fluorescence intensity corresponding to at least 5%, preferably at least 10%, more preferably at least 20%, even more preferably at least 30%, such as at least 40%, for example at least 50%, such as at least 60%, for example at least 70%, such as at least 80%, for example at least 90%, such as in the range of 5 to 100%, for example in the range of 10 to 100%, such as in the range of 20 to 100%, for example in the range of 30 to 100%, such as in the range of 40 to 100%, for example in the range of 50 to 100%.

The positive control may for example be a resin bead (or optionally several resin beads kept in a separate container or well) comprising a compound known to influence the cellular response. By way of example, if the cellular response is activation of an intracellular signal transduction pathway, then the positive control may be a resin bead comprising a known compound that stimulate one or multiple components of said intracellular signal transduction pathway. The positive control signal is then obtained after release from the resin of the compound. Alternatively the positive control may be a resin bead comprising a known ligand of a receptor activating the signal transduction pathway, for example a naturally occurring ligand. The negative control may be a resin bead (or optionally several resin beads kept in a separate container or well) optionally comprising a cell adhesion compound, but otherwise comprising no library member or other test compound.

In another embodiment of the selection criterion is low fluorescence. This may for example be the case, when the cellular response is inhibition of a signal transduction pathway and the reporter system comprises a gene encoding a fluorescent protein, where an active signal transduction pathway leads to expression of said gene. This may also be the case when the cellular response is disruption of interaction between two cellular proteins, wherein the reporter system is a FRET or BRET reporter system. After release of a proportion of the library members to be tested, resin beads may be selected using a method comprising the steps of:

1. Determining the fluorescence intensity of positive control resin beads and setting this fluorescence intensity to 0%
2. Determining the fluorescence intensity of negative control resin beads and setting this fluorescence intensity to 100%
3. Selecting resin beads having a fluorescence intensity corresponding to at least 5%, preferably at least 10%, more preferably at least 20%, even more preferably at least 30%, such as at least 40%, for example at least 50%, such as at least 60%, for example at least 70%, such as at least 80%, for example at least 90%, such as in the range of 5 to 100%, for example in the range of 10 to 100%, such as in the range of 20 to 100%, for example in the range of 30 to 100%, such as in the range of 40 to 100%, for example in the range of 50 to 100%.

The positive control may for example be a resin bead(s) comprising a compound known to influence the cellular response. By way of example, if the cellular response is inhibition of an intracellular signal transduction pathway, then the positive control may be a resin bead(s) comprising a compound known to inhibit one or multiple components of signal transduction pathway. The control signal is then obtained after release from the resin of the compound. Alternatively the positive control may be a resin bead comprising a known antagonist of a receptor known to activate said signal transduction pathway. If the cellular response is induction of apoptosis, then the positive control may be a resin bead comprising a compound known to induce apoptosis The negative control may be a resin bead optionally comprising a cell adhesion compound, but otherwise comprising no library member or other test compound.

One method of selecting resin beads using FABS is illustrated in FIG. 1A.

In one preferred embodiment selection is performed manually with the aid of a fluorescence microscope. In this embodiment the fluorescence intensity or other fluorescence properties are judged manually.

Figure 1B:
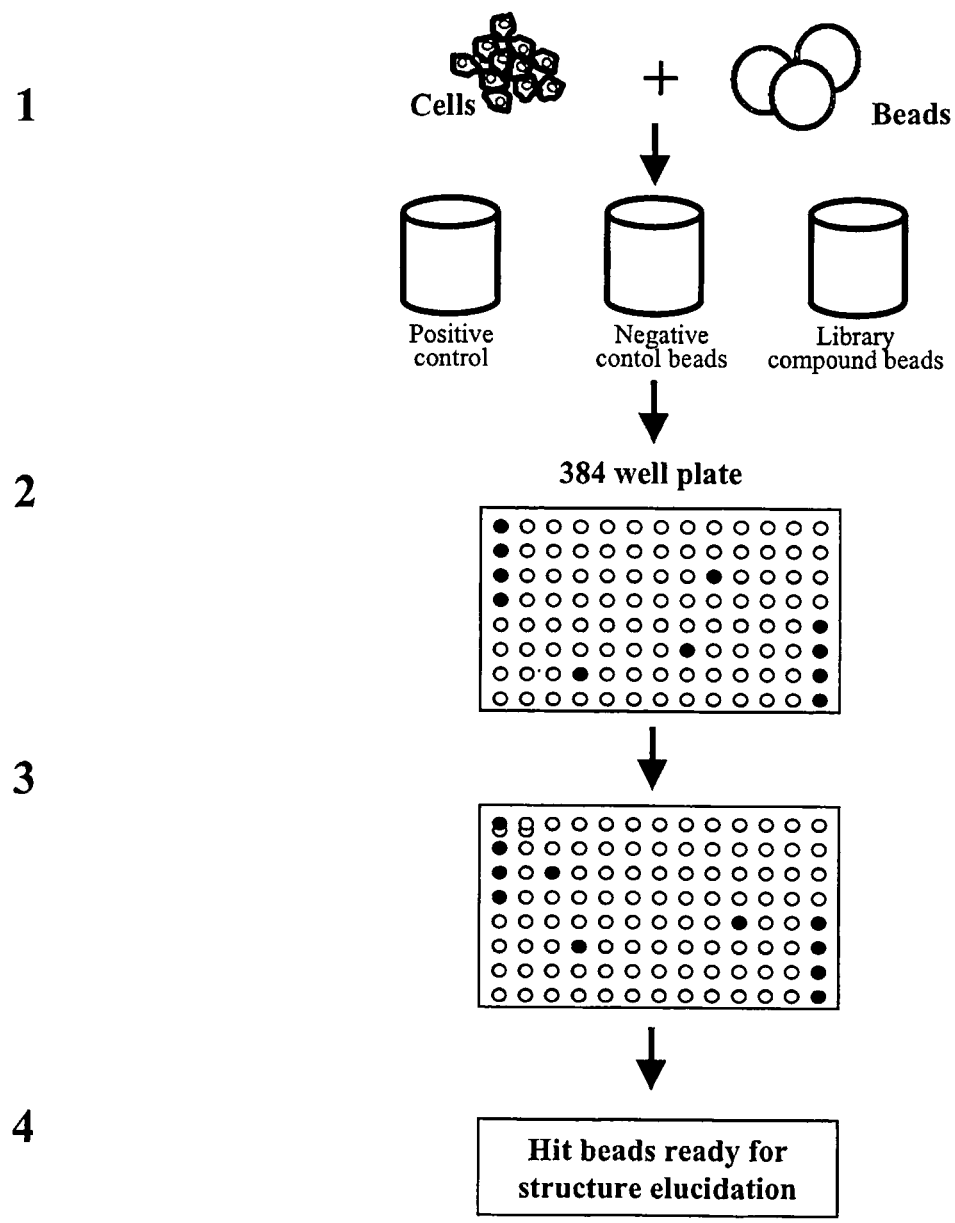
FIG. 1B illustrates a method of identifying a resin bead comprising a compound influencing a cellular response linked to a reporter system generating a fluorescent output detectably using a plate reader or image acquisition analysis. The method involves 1) Grow cells on beads for 24 hrs and Fix cells in EtOH, 2) Add app. 20 beads to each well and Identify hit wells using plate reader or image acquisition/analysis and 3) Transfer beads from hit wells to a new 384 well plate—one bead/well and identify hit wells using plate reader or image acquisition. If for example 500,000 beads are screened with 20 beads/well, approx. 25,000 wells, i.e. approx. 68 plates must be screened. With a 0.1% hit rate, there will be approx. 500 hit wells comprising approx. 10,000 beads, which amounts to analysis of approx. 27 plates in the second round. Alternatively, positive beads may be picked directly (preferably without fixation) after the first identification using image acquisition analysis. The method may for example be used for analysis of expression of a Cre-YFP construct.

When the selection criterion is fluorescence intensity of localisation, the resin beads may also be analysed using a plate reader or image acquisition. An example of such an analysis is given in FIG. 1B.

If the selection criterion is localisation, then resin beads are generally analysed by a fluorescence or imaging microscope. Said microscope may optionally be equipped with a micromanipulator capable of picking out single beads. Resin beads are scanned for cells where the fluorescence signal is located at the desired intracellular location and these resin beads are selected. The selection may be manually or it may be automated.

In embodiments of the invention, wherein the detectable output is light emission or the detectable output may be linked to a light signal, then the predetermined selection criterion could be any property of the light. For example the selection criteria could be light intensity above or below a predetermined threshold value. Light can be detected for example by the eye, in a microscope, and if the light is emitted via bioluminescence it can be measured by a luminometer In embodiments of the invention, wherein the detectable output is a radioactive signal or the detectable output may be linked to a radioactive signal, then the selection criterion could be any property of said radioactive signal, such as intensity above or below a predetermined threshold value or localisation of the radioactive signal.

In embodiments of the invention, wherein the detectable output is a colour signal or the detectable output may be linked to a colour signal, then the selection criterion could be any property or said colour signal. For example the predetermined selection criterion could be a colour intensity above or below a specific threshold value or it could be a specific colour. The colour signal could be detected using any suitable colorimetric method, such as a spectrophotometer or a microscope.

Resin beads comprising cells meeting at least one selection criterion, such as any of the selection criteria mentioned herein above are selected. In certain embodiments of the invention resin beads comprising cells meeting at least two, for example 2, such as 3, for example 4, such as in the range of 5 to 10, for example of in the range of 10 to 25 selection criteria are selected.

It is also possible within the present invention to select resin beads comprising cells meeting one or more predetermined selection criteria and subsequently to subject said beads to one or more additional selection rounds, wherein resin beads comprising cells meeting one or more additional selection criteria are selected.

Resin beads meeting said at least one predetermined selection criteria may be selected by manually sorting for example with the aid of a microscope, or for example by sorting by fluorescence or by colour or by morphology depending on the detectable output and the selection criterion. Positive beads may be picked directly under the microscope, such as under a fluorescence microscope for example manually or with the aid of a micromanipulator. Frequently, in the range of 100 to 1,000,000, for example in the range of 1000 to 100,000, such as in the range of 5000 to 50,000 resin beads may be placed on a suitable surface, such as in a dish or on a coverglass and subsequently examined by microscopy. Alternatively, the sorting process may be automated with the use of specially designed, commercially available bead sorters (Union Biometrica, Sommerville, Mass.) and detecting for example fluorescence intensity (Meldal, 2002, Biopolymers, 66: 93-100). In general, resin beads can be sorted at a rate of up to 100 beads per second, or even faster depending on the equipment used and its reading capacity. A range of about 5-30 beads per second is generally used with known instruments. Slower rates may be used to increase accuracy, however any suitable rate may be used with the present invention, such as much higher rates. Preferred, is a rate where only one resin bead passes through the detector at a time. It is also comprised within the present invention to select resin beads using a plate reader. In general in the range of 1 to 1000, such as 10 to 500, for example 50 to 100 resin beads are placed in each well of a multiter plate and analysed. Beads from positive wells may then be further examined.

In one embodiment of the invention resin beads may be selected by comparing the detectable output, with the detectable output generated by control resin beads, for example positive and/or negative control resin beads. Positive control resin beads are beads comprising a compound capable of inducing the desired cellular response, whereas negative control resin beads comprises no such compound. By way of example, if the cellular response is activation of an intracellular signal transduction pathway with a known natural ligand, the positive control resin bead may comprise said ligand, whereas the negative control resin bead comprises no compound except optionally a cell adhesion compound.

If the detectable output is a quantifiable signal, then resin beads may be selected, comprising cells where the detectable output is higher or lower than the detectable output from cells attached to the positive or negative control resin bead. By way of example, if the detectable output is fluorescence intensity, then resin beads comprising cells displaying a fluorescence intensity which is higher than the negative control and lower than the positive control could for example be selected.

Figure 2A:
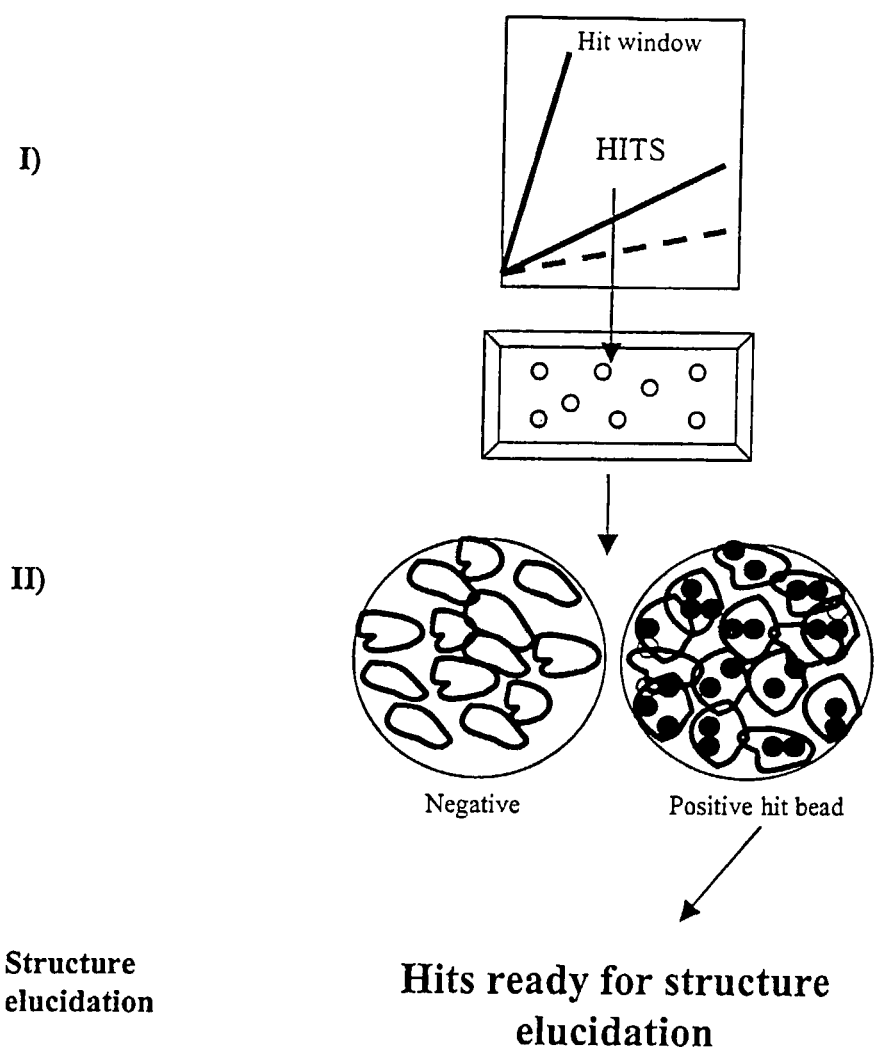
FIG. 2A illustrates a multiplexed screen involving FABS and microscopy. The screen involves I) identification of positive hits by FABS as displayed in FIG. 1, followed by II) a step of microscopy identifying resin beads comprising cells with an internal fluorescent signal.
Figure 2B:
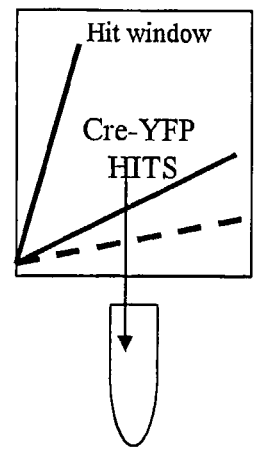
FIG. 2B illustrates a multiplexed screen involving two FABS analysis. The screen involves I) identification of positive hits by FABS as displayed in FIG. 1, followed by II) a second FABS analysis.
Figure 2B:
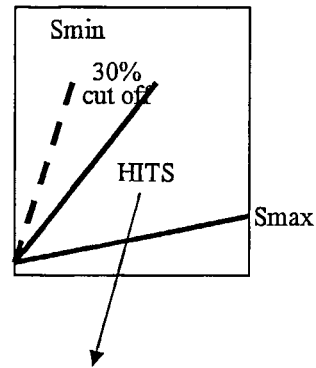

Non-limiting examples of methods of selecting resin beads are illustrates in FIGS. 1 and 2.

Identification of Compound

Once a resin bead has been selected, the compound that is remaining after partial release on said bead may be identified. Preferably, only one resin bead is used at a time. Thus if said resin bead only comprises one library member in one or more copies, then only one compound is identified at a time.

The process for identification of the library member depends on the type of library used. For a library of primarily oligomeric compounds, the library member can be analysed by Mass Spectroscopy (MS), particularly if the library was synthesized in such a way that the synthetic history of the compound is captured, for example, using a capping procedure to generate fragments of the compound that differ in mass by one building block (see, for example, Youngquist et al., 1995, J. Am Chem. Soc., 117: 3900-06). This capping procedure is most efficient when the cap and the building block are reacted at the same time. The capping agent can be any class of compound that has at least one functional group in common with the building block used to generate the oligomer, so that both the capping agent and the building block can react when added to the resin in an appropriate ratio. Alternatively, the capping agent can have two functional groups in common with the building block where one of the groups in common, such as the group in the building block that is used for the elongation of the oligomer, is orthogonally protected. For example, in a synthesis of a peptide using the Fmoc strategy, the capping agent could be the same as the building block but with a Boc group protecting the reactive amine instead of the Fmoc group (see St. Hilaire et al., 1998, J. Am. Chem. Soc., 120: 13312-13320). In another example, if the building block is a protected haloamine, the capping agent could be the corresponding alkylhalide.

Where the library is synthesized by parallel synthesis (a parallel array), the compound can be identified simply by the knowledge of what specific reaction components were reacted in a particular compartment. The structure can be confirmed by cleavage of a small portion of compound from the solid support and analyzed using routine analytical chemistry methods such as infrared (IR), nuclear magnetic resonance (NMR), mass spectroscopy (MS), and elemental analysis. For a description of various analytical methods useful in combinatorial chemistry, see: Fitch, 1998-99, Mol. Divers., 4: 39-45; and Analytical Techniques in Combinatorial Chemistry, M. E. Swartz (Ed), 2000, Marcel Dekker: New York.

In a preferred embodiment however the library has been synthesised by a split-mix approach where the precise structure of the compound of a specific bead is unknown. In this embodiment, the library member can be identified using a variety of methods. The compound may be cleaved off the resin bead, for example by cleaving the cleavable linker and then analyzed using IR, MS, or NMR. For NMR analysis, larger beads containing approximately 5 nmoles of material are preferably used for the acquisition of 1-dimensional (1-D) and 2-dimensional (2-D) NMR spectra. Furthermore, these spectra can be attained using high-resolution MAS NMR (magic angle spinning nuclear magnetic resonance) techniques.

Alternatively, high resolution-MAS NMR spectra can be acquired while the ligand is still bound to the solid support, as described for example, in Gotfredsen et al., 2000, J. Chem. Soc., Perkin Trans., 1: 1167-71. The compound may also be identified by release of the compound and fragmentation by MS-MS in MALDI or electrospray mode.

Frequently, resin beads used for library synthesis contain about 100 to 500 pmoles of material, which is generally insufficient for direct analysis using NMR techniques. In such situations, the libraries can be synthesised with special encoding to facilitate identification of the library member. For a review of encoding strategies employed in combinatorial chemistry see: Barnes et al., 2000, Curr. Opin. Chem. Biol., 4: 346-50. Most coding strategies include the parallel synthesis of the encoding molecule (for example, DNA. PNA, or peptide) along with the library compounds. This strategy requires a well-planned, time consuming, orthogonal protecting group scheme. Furthermore, the encoding molecule itself can sometimes influence the cell leading to false positives. Alternatively, the library members can be encoded using radiofrequency tags or using optical encoding, such as quantum dot encoding, spherical encoding or distance encoding. These methods alleviates the problem of false positives stemming from the coding tags, but is generally only useful for small libraries in a one-bead-one-compound system due to the sheer bulk of the radiofrequency tag. Alternatively, single beads can be analyzed in a non-destructive manner using infrared imaging. This method gives limited information and while useful for pre-screening, is not recommended for conclusive structural determination.

In a preferred embodiment of the invention the library member(s) comprised within selected resin beads are identified using mass spectrometry (MS). MS can be used alone to identify the library member. The library member can be cleaved from the resin bead, the molecular mass determined, and subsequently fragmented into sub-species to conclusively determine the structure by combination with knowledge of contained structures in the library. MS-based methods of compound identification are useful in this invention, as they require very little material, and can utilise pico- to femtomole amounts of compound.

After identification of the compound it may be desirable to confirm the activity of said compounds by further in vitro and/or in vivo assays. For example, resin beads comprising the identified compound and optionally an adhesion compound may be synthesized and the cellular response confirmed. It is also possible to test identified compounds in in vitro assays in the absence of beads. Cells may for example be grown directly in a tissue culture dish, flask or coverglass and the identified compound can be added directly to the medium of said cells. If several reporter systems are available for the particular cellular response then preferably several different reporter assays may be tested in vitro, in order to identify very useful compounds. By way of example, if the cellular response is induction of apoptosis, then for example activity of caspases, cell growth/cell death and/or interaction between Smac and inhibitors of apoptosis may be tested.

Multiplexing

The methods disclosed by the present invention may also be used in multiplexing methods.

For example, the methods may be used to identify compounds modifying at least two cellular responses, such as 2, for example 3, such as 4, for example in the range of 5 to 10, such as in the range of 10 to 25 cellular responses.

In such methods step c) of the method outlined above (see the section "Summary of the invention") preferably involves screening resin beads for beads comprising cells meeting at least two, such as 2, for example 3, such as 4, for example in the range of 5 to 10, such as in the range of 10 to 25 predetermined selection criteria, wherein each selection criterion is preferably related to a different detectable output.

In such a method more than one kind of cell may be attached to each resin bead and the different cellular responses may be detected in different kinds of cells. For example, a first cell line comprising a first reporter system linked to a first cellular response and a second cell line comprising a second reporter system linked to a second cellular response and optionally additional cell line(s) comprising additional reporter system(s) linked to additional cellular response(s) may all be attached to a single bead. Resin beads comprising cells meeting selection criteria linked to all the different reporter systems may then be selected.

Depending on the detectable outputs, said detectable output may be determined using any of the methods described herein above. In one preferred embodiment at least two detectable outputs are fluorescent outputs, preferably of different excitation and/or emmission. Thus resin beads meeting said at least two selection criteria may be selected in one step using a FABS with at least 2 channels in both excitation and emmission. Similarly, more than two different fluorescent properties may be selected for in an suitable FABS. The at least two detectable outputs may be in the same cell line or they may be in different cell lines.

Examples of multiplexing methods are illustrated in FIGS. 2A and 2B.

EXAMPLES

Example 1

General Methods for Solid Phase Peptide Synthesis (SPPS) General for Chemical Synthesis:

All chemicals described, commercially available and used without further purification. All solvents were HPLC-grade. PEGA-resins were purchased from VersaMatrix A/S, Copenhagen. Each washing step lasted 2 min unless otherwise stated. Purifications were performed on a standard reverse phase HPLC using gradients of acetonitrile-Water with various amounts of TFA.

Coupling of HMBA Linker to PEGA—Resin:

Dry PEGA-resin was swelled in DCM and washed with DMF (3×). 3.0 eq. HMBA, 2.9 eq. TBTU and 3.0 eq. NEM were mixed in appropriate DMF and allowed to react for 10 min. The mixture was added to resin and after 2 h the resin was washed with DMF (6×), DCM (6×) and lyophilised.

General Procedure for Coupling of Amino Acid to HMBA-Linker:

Dry PEGA-resin with HMBA-linker was swelled in DCM. 3.0 eq. Fmoc-protected amino acid, 2.25 eq. MeIm and 3.0 eq. MSNT were mixed in appropriate amount of DCM and added to resin. After 1 h the resin was washed with DCM (3×) and the coupling was repeated as above once. After coupling for 1 h the resin was washed with DCM (6×), DMF (6×), DCM (6×) and lyophilised.

General SPPS Coupling Procedure:

The terminal amino acid on the resin was Fmoc-deprotected by treatment with 20% piperidine in DMF (1×2 min+ 1×18 min) followed by washing with DMF (6×). 3.0 eq. Fmoc-protected amino acid, 2.9 eq. TBTU and 3.0 eq. NEM were mixed in appropriate amount of DMF and allowed to react for 10 min. The mixture was added to the resin and after 2 h the resin was washed with DMF (6×).

I. General Side Chain Deprotection Procedure:

Dry PEGA-resin with linker, usually acid stable linker(s) and peptide or optionally compound was swelled in $H_2O$ and the side chains was deprotected with 95% TFA (aq) (2×15 min). (If Pmc groups were present cleavage time was 6 h). The resin was washed with $H_2O$ until washing water had pH=5-7. The resin was then washed with DMF (6×), DCM (6×) and lyophilised.

General HMBA Cleavage Procedure:

Dry PEGA-resin with HMBA linker and attached compound was swelled in water and NaOH (aq.) 0.1 M was added. After 2 h HCl (aq.) 0.1 M was used for neutralisation and then AcN was added until the $H_2O$/AcN ratio was 1:1 by volume. The resin was filtered off and the liquid was used direct for RP-HPLC or/and Q-TOF MS analysis.

The above general procedures are used for solid phase peptide synthesis in the following examples unless otherwise specified.

Example 2a

Screening of Adhesion Peptide Library

Approx. 100 adhesion peptide library beads were mixed with 1×10E6 cells (BHK, CHO, U2OS, Hek) in each well of a Falcon 12 well plate using 2 ml growth medium. The adhesion peptide library was prepared according to the general methods for solid phase peptide synthesis outlined above. The library consisted of heptamers of D-amino acids. The peptide library beads were PEGA beads each coupled to a potential adhesion peptide. The cells and beads were mixed gently every 15 min for 2 hrs. Supernatant with non-attached cells were removed and new growth medium added. Cells/beads were incubating for another 16 hrs. (37° C., 5% $CO_2$). Cell adhesive beads were identified using a microscope with 10× objective and positive beads were transferred to a filter paper (to suck off medium). Peptides were identified by amino acid sequencing. Examples of useful peptides are given in table 2.

Example 2b

Identification of an Adhesion Peptide with Low Absorption of Fluorescent Components from Growth Medium and High Adhesion Properties An adhesion D-amino peptide library was synthesized (500.000 members) as described above in Example 2a and screened for low fluorescence/high adherence properties. This was done in 4 steps:

1) Selection of low fluorescent beads by Fluorescence Activated Bead Sorting (FABS). The 500.000 member adhesion peptide library was FABSorted and 150.000 low fluorescent beads were isolated.
2) Selection of beads with good cell adhesion properties. The 150.000 low fluorescent beads were incubated with GFP expressing U2OS cells followed by FABS sorting for high fluorescence (high cell adhesion). 536 beads were isolated.
3) Identification and isolation of beads with high Hek293 cell adherence properties. The 536 beads were cleared for U2OS cells and incubated with GFP expressing Hek293 cells. 47 beads with high cell adhesion properties were isolated using a fluorescence microscope.
4) Sequence elucidation and re-synthesis of selected peptides. 22 peptides were sequenced and six of them were re-synthesized. Based on Structure-Activity of the six peptides, four additional ones were synthesized. The peptide defined by SEQ ID 35 showed the best overall performance.

Example 3

Synthesis of Peptides Binding to the ML-IAP BIR Domain

This example describes the preparation of 6 peptides known to interact with the BIR domain of ML-IAP (livin). The syntheses were performed according to the "general SPPS coupling Procedure" above.

Synthesis of H-Ala-Val-Pro-Ile-Ala-Gln-Lys-Ser-Glu-OH (SEQ ID NO. 82), H-Ala-Val-Pro-Phe-Ala-Val-Lys-Ser-Glu-OH (SEQ ID NO. 83), and H-Ala-Glu-Ala-Val-Pro-Trp-Lys-Ser-Glu-OH (SEQ ID NO. 84)

Coupling 1-3: HMBA modified PEGA 800 beads (600 mg, Versabeads A-800, 315-500 µm, 0.32 mmol NH2/g) were coupled under standard MSNT coupling conditions (Example 1) with Fmoc-Glu(O'Bu)OH followed by standard TBTU coupling of FmocSer(O'Bu)OH and FmocLys(Boc)OH.

Coupling 4-8: The resin was separated into three 200 mg portions and three parallel couplings were performed with the respective amino acids according to the "general SPPS coupling procedure in Example 1 (Trp, Glu and Gln were side chain protected as the N-Boc, O-'Bu and N-trityl derivatives respectively). After the last coupling side chain deprotection was performed according to the general procedure (Example 1).

The peptides were detached according to the general HMBA cleavage procedure (Example 1) and the peptides purified with preparative HPLC.

H-Ala-Val-Pro-Ile-Ala-Gln-Lys-Ser-Glu-OH (SEQ ID NO. 82): Yield after purification: 30 mg (>98% pure according to HPLC). MALDI-MS Calcd. $(M+H)^+$ 942.5; Found 942.7. 25 NMR data were in accordance with the predicted structure.

H-Ala-Val-Pro-Phe-Ala-Val-Lys-Ser-Glu-OH (SEQ ID NO. 83): Yield after purification: 32 mg (>98% pure according to HPLC). MALDI-MS. Calcd. (M+H)+ 947.5; Found 948.0. NMR data were in accordance with the predicted structure.

H-Ala-Glu-Ala-Val-Pro-Trp-Lys-Ser-Glu-OH (SEQ ID NO. 84): Yield after purification: 38 mg (>98% pure according to HPLC). MALDI-MS. Calcd. (M+H)+ 1016.5; Found 1016.5. NMR data were in accordance with the predicted structure.

Synthesis of H-Ala-Val-Pro-Ile-OH (SEQ ID NO. 85)

Synthesis performed according to the general SPPS procedure on 200 mg of HMBA modified PEGA 800 beads. Yield after HMBA cleavage and purification: 17 mg. (>98% pure according to HPLC). ES-MS. Calcd. (M+H)+ 399.2. Found 399.2. NMR data were in accordance with the predicted structure.

Synthesis of H-Ala-Glu-(1-amino-cyclopentanecarboxyl)-Phe-OH (SEQ ID NO. 86)

Synthesis performed according to the general SPPS procedure on 200 mg of HMBA modified PEGA 800 beads. Yield after HMBA cleavage and purification: 22 mg. (>98% pure according to HPLC). ES-MS. Calcd. (M+H)+ 477.2. Found 477.2. NMR data were in accordance with the predicted structure.

Synthesis of H-Ala-Glu-(azetidine-1-carboxyl)-(homo-Phe)-OH (SEQ ID NO. 87)

Synthesis performed according to the general SPPS procedure on 200 mg of HMBA modified PEGA 800 beads. Yield after HMBA cleavage and purification: 21 mg. (>98% pure according to HPLC). ES-MS. Calcd. (M+H)+ 463.2. Found 463.2. NMR data were in accordance with the predicted structure.

The structures of the 6 synthesized peptides are given below.

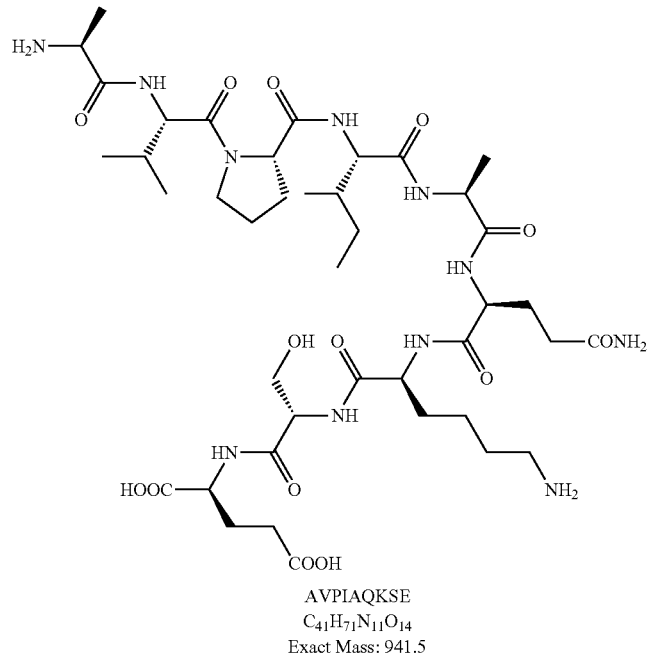

AVPIAQKSE
$C_{41}H_{71}N_{11}O_{14}$
Exact Mass: 941.5

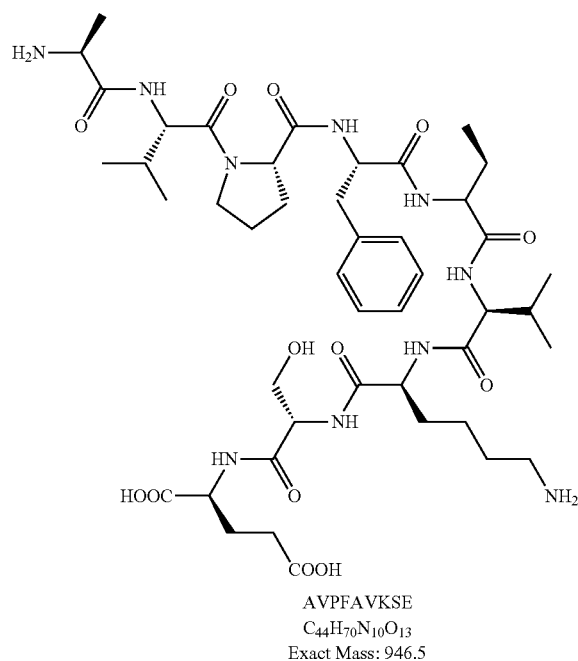

AVPFAVKSE
$C_{44}H_{70}N_{10}O_{13}$
Exact Mass: 946.5

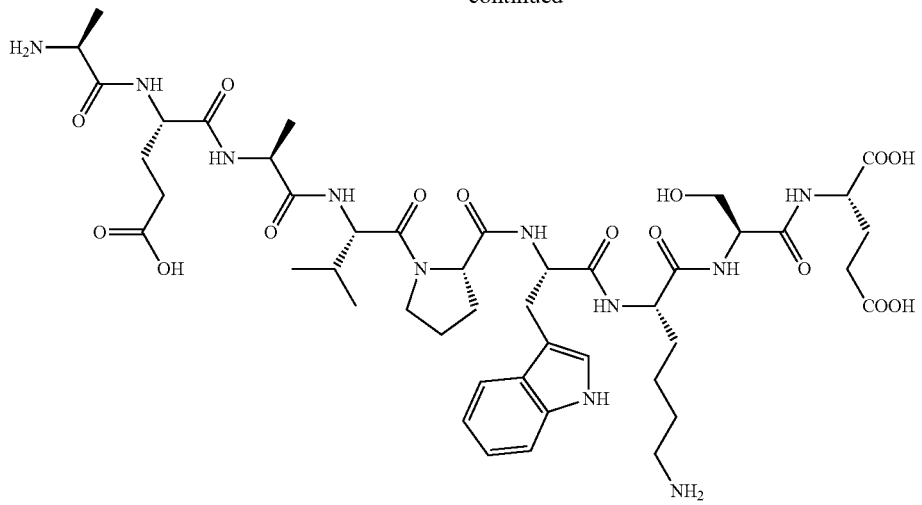

AEAVPWKSE
$C_{46}H_{69}N_{11}O_{15}$
Exact Mass: 1015.5

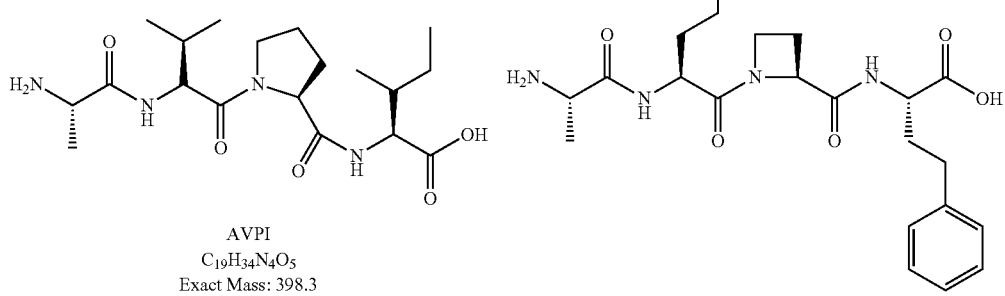

AVPI
$C_{19}H_{34}N_4O_5$
Exact Mass: 398.3

AEXX
$C_{22}H_{30}N_4O_7$
Exact Mass: 462.2

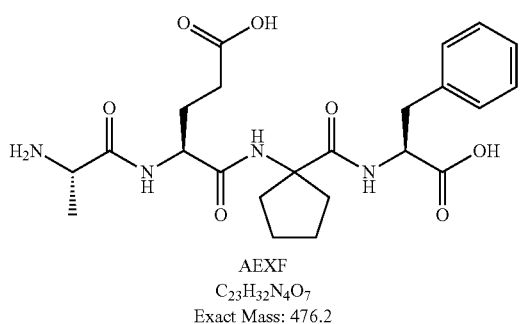

AEXF
$C_{23}H_{32}N_4O_7$
Exact Mass: 476.2

Example 4

Synthesis of a 44,000 Member Tetrapeptide Library on Beads with Fixed Adhesion Peptide This example describes the preparation of a library of tetrapeptides (44.000 members) on resin beads containing a "cell adhesive peptide". This "two compound one bead" (TCOB) library may be used for in vivo screening of the tetrapeptides for e.g. antagonists action on the ML-IAP receptor.

FmocLys(Fmoc)/BocVal (~1:1) Modification of Pega 1900 Beads

Dry Versabeads A-1900 (315-500 μm, 0.2 mmol NH2/g) (1.20 g) were dissolved in dry DMF (10 mL) and coupled with FmocLys(Fmoc)OH (0.24 mmol, 1 eq) and Boc-ValOH (0.48 mmol, 2 eq) using the general SPPS coupling procedure.

Fmoc to Alloc Transformation of Lys Protecting Groups

The beads were Fmoc deprotected using the standard procedure. The beads were washed several times with DCM (−10° C.) and finally added DCM (10 mL) with the same temperature. DIPEA (0.9 mL) was added followed by dropwise addition of AllocCl (allyloxycarbonylchloride) (0.26 mL). The reaction mixture was kept under N₂ and stirred at RT for 2 h (Kaiser test was negative). The resin was washed with DCM (6×), DMF (6×) and DCM (6×) and lyophilised overnight.

Attachment of Photolabile Linker (PLL) to Val

The dried beads (~1.2 g) were Boc deprotected with 30% TFA in DCM (2+45 min). The resin was washed with DCM (3×), 20% pip in DMF (2×) and DMF (6×). The photo cleavable linker (4-[(1-Fmoc-aminoethyl)-2-methoxy-5-nitrophenoxy]butanoic acid) (187 mg, 0.36 mmol, 3 eq) was dissolved in DMF followed by NEM (100 µL, 0.72 mmol, 6 eq) and TBTU (111 mg, 0.35 mmol, 2.9 eq). After stirring for 5 minutes the mixture was added to the beads and left with occasional stirring for 3.5 h. (Kaiser test neg). Wash with DMF (10×), DCM (6×) and lyophilised overnight in the dark.

Preparation of Tetrapeptide Library with 44,000 Members

The beads containing the Fmoc protected photo linker (1.00 g) were placed in a custom made 20 well synthesizer. Four couplings using the general SPPS TBTU coupling procedure were performed using a split and mix protocol. Amino acids (20×20×10×10) used for couplings are given in Tables 3 to 6. For the $3^{rd}$ and $4^{th}$ coupling each amino acid is added to 2 wells. Protection groups are left on the peptides after end couplings.

TABLE 3

Amino acids used for the 1st coupling.

| Member number | 1 | 2 | 3 | 4 |
|---|---|---|---|---|
| Structure | (4-F-Phe, FmocHN) | (3-F-Phe, FmocHN) | (4-CF$_3$-Phe, FmocHN) | (4-CN-Phe, FmocHN) |
| Mw | Mol. Wt.: 405.42 | Mol. Wt.: 405.42 | Mol. Wt.: 455.43 | Mol. Wt.: 412.44 |
| micromol | 10 | 10 | 10 | 10 |
| Weight (mg) | 4.05 | 4.05 | 4.55 | 4.12 |

| Member number | 5 | 6 | 7 | 8 |
|---|---|---|---|---|
| Structure | (3-CN-Phe, FmocHN) | (benzothiophene-Ala, FmocHN) | (thiophene-Ala, FmocHN) | (3,4-dimethoxy-Phe, NHFmoc) |
| Mw | Mol. Wt.: 412.44 | Mol. Wt.: 443.51 | Mol. Wt.: 393.46 | Mol. Wt.: 447.48 |
| micromol | 10 | 10 | 10 | 10 |
| Weight (mg) | 4.12 | 4.43 | 3.93 | 4.47 |

| Member number | 9 | 10 | 11 | 12 |
|---|---|---|---|---|
| Structure | (anthranilic acid, NHFmoc) | (1-amino-cyclopentane-COOH, FmocHN) | (1-amino-cyclohexane-COOH, FmocHN) | (Gln(Trt), FmocHN) |
| Mw | Mol. Wt.: 359.37 | Mol. Wt.: 351.4 | Mol. Wt.: 365.42 | Mol. Wt.: 610.7 |
| micromol | 10 | 10 | 10 | 10 |
| Weight (mg) | 3.59 | 3.51 | 3.65 | 6.11 |

TABLE 3-continued

Amino acids used for the 1st coupling.

| Member number | 13 | 14 | 15 | 16 |
|---|---|---|---|---|
| Structure | 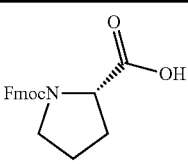 | 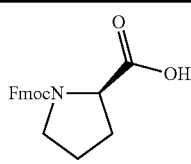 | 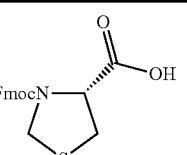 | 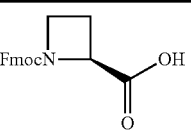 |
| Mw | Mol. Wt.: 411.45 | Mol. Wt.: 387.43 | Mol. Wt: 417.45 | Mol. Wt.: 421.87 |
| micromol | 10 | 10 | 10 | 10 |
| Weight (mg) | 4.11 | 3.87 | 4.17 | 4.22 |

| Member number | 17 | 18 | 19 | 20 |
|---|---|---|---|---|
| Structure | 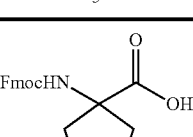 | 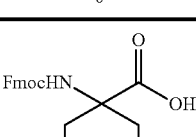 | 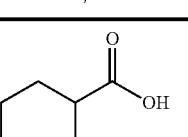 | 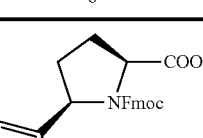 |
| Mw | Mol. Wt.: 413.47 | Mol. Wt.: 427.49 | Mol. Wt.: 648.77 | Mol. Wt: 355.41 |
| micromol | 10 | 10 | 10 | 10 |
| Weight (mg) | 4.13 | 4.27 | 6.49 | 3.55 |

TABLE 4

Amino acids used for the 2nd coupling.

| Member number | 1 | 2 | 3 | 4 |
|---|---|---|---|---|
| Structure | | | | |
| Mw | Mol. Wt.: 337.37 | Mol Wt.: 337.37 | Mol.Wt.: 355.41 | Mol. Wt.: 323.34 |
| micromol | 10 | 10 | 10 | 10 |
| Weight (mg) | 3.37 | 3.37 | 3.55 | 3.23 |

| Member number | 5 | 6 | 7 | 8 |
|---|---|---|---|---|
| Structure | | | | |
| Mw | Mol. Wt.:351.4 | Mol. Wt.: 365.42 | Mol. Wt.: 351.4 | Mol. Wt.: 413.47 |
| micromol | 10 | 10 | 10 | 10 |
| Weight (mg) | 3.51 | 3.65 | 3.51 | 4.13 |

TABLE 4-continued

Amino acids used for the 2nd coupling.

| Member number | 9 | 10 | 11 | 12 |
|---|---|---|---|---|
| Structure | (4-F-Phe, FmocHN-CH(CH2-C6H4-F)-COOH) | (Phe, FmocHN-CH(CH2-Ph)-COOH) | (2-thienyl-Ala, FmocHN-CH(CH2-thienyl)-COOH) | (Gln(Trt), FmocHN-CH(CH2CH2-C(O)NHTrt)-COOH) |
| Mw | Mol Wt.: 405.42 | Mol. Wt.: 387.43 | Mol. Wt.: 393.46 | Mol. Wt.: 610.7 |
| micromol | 10 | 10 | 10 | 10 |
| Weight (mg) | 4.05 | 3.87 | 3.93 | 6.11 |

| Member number | 13 | 14 | 15 | 16 |
|---|---|---|---|---|
| Structure | (Val, FmocHN-CH(iPr)-COOH) | (Ile, FmocHN-CH(sBu)-COOH) | (Asp(OtBu), FmocHN-CH(CH2-C(O)OtBu)-COOH) | (4-phenyl-piperidine-4-carboxylic acid, Fmoc-protected) |
| Mw | Mol. Wt.: 339.39 | Mol. Wt.: 353.41 | Mol. Wt.: 411.45 | Mol. Wt.: 477.49 |
| micromol | 10 | 10 | 10 | 10 |
| Weight (mg) | 3.39 | 3.53 | 4.11 | 4.27 |

| Member number | 17 | 18 | 19 | 20 |
|---|---|---|---|---|
| Structure | (Arg(Pbf), FmocHN-CH(CH2CH2CH2-NH-C(=NH)-NH-Pbf)-COOH) | (Thr(tBu), FmocHN-CH(CH(OtBu)CH3)-COOH) | (His(Boc), FmocHN-CH(CH2-imidazole-Boc)-COOH) | (Ala, FmocHN-CH(CH3)-COOH) |
| Mw | Mol. Wt.: 648.77 | Mol. Wt.: 397.46 | Mol. Wt.: 477.51 | Mol. Wt.: 311.33 |
| micromol | 10 | 10 | 10 | 10 |
| Weight (mg) | 6.48 | 3.97 | 4.77 | 3.11 |

TABLE 5

Amino acids used for the 3rd coupling.

| Member number | 1 | 2 | 3 | 4 |
|---|---|---|---|---|
| Structure | (Val, FmocHN-CH(iPr)-COOH) | (Leu, FmocHN-CH(iBu)-COOH) | (Ile, FmocHN-CH(sBu)-COOH) | (Thr(tBu), FmocHN-CH(CH(OtBu)CH3)-COOH) |
| Mw | Mol. Wt.: 339.39 | Mol. Wt.: 353.41 | Mol. Wt.: 353.41 | Mol. Wt.: 397.46 |
| micromol | 10 | 10 | 10 | 10 |
| Weight (mg) | 3.39 | 3.53 | 3.53 | 3.97 |

TABLE 5-continued

Amino acids used for the 3rd coupling.

| Member number | 5 | 6 | 7 | 8 |
|---|---|---|---|---|
| Structure | Fmoc-Asp(Ot-Bu)-OH | Fmoc-Asn(Trt)-OH | Fmoc-Glu(Ot-Bu)-OH | Fmoc-Gln(Trt)-OH |
| Mw | Mol. Wt.: 411.45 | Mol. Wt.: 596.67 | Mol. Wt.: 425.47 | Mol. Wt.: 610.7 |
| micromol | 10 | 10 | 10 | 10 |
| Weight (mg) | 4.11 | 5.97 | 4.25 | 6.11 |

| Member number | 9 | 10 | 11 | 12 |
|---|---|---|---|---|
| Structure | Fmoc-His(Boc)-OH | Fmoc-Dab(Boc)-OH | | |
| MW | Mol. Wt.: 477.51 | Mol. Wt.: 440.49 | | |
| micromol | 10 | 10 | | |
| Weight (mg) | 4.78 | 4.40 | | |

TABLE 6:

Amino acids used for the 4th coupling.

| Member number | 1 | 2 | 3 | 4 |
|---|---|---|---|---|
| Structure | Boc-Gly-OH | Boc-Ala-OH | Boc-Val-OH | Boc-Ser(t-Bu)-OH |
| Mw | Mol. Wt.: 175.18 | Mol. Wt.: 189.21 | Mol. Wt.: 217.26 | Mol. Wt.: 261.31 |
| micromol | 10 | 10 | 10 | 10 |
| Weight (mg) | 3.50 | 3.78 | 4.35 | 5.22 |

| Member number | 5 | 6 | 7 | 8 |
|---|---|---|---|---|
| Structure | Boc-Thr(t-Bu)-OH | Boc-Aze-OH | Boc-Aib-OH | Boc-Dap(Boc)-OH · DCHA |
| Mw | Mol. Wt.: 275.34 | | Mol. Wt.: 203.24 | Mol. Wt.: 485.66 |
| micromol | 10 | 10 | 10 | 10 |
| Weight (mg) | 5.51 | 4.02 | 4.06 | 9.71 |

TABLE 6:-continued

Amino acids used for the 4th coupling.

| Member number | 9 | 10 | 11 | 12 |
|---|---|---|---|---|
| Structure | (Boc-Pro-OH) | (BocN-His(Boc)-OH) | | (dicyclohexylammonium salt structure) |
| Mw | Mol. Wt.: 215.25 | Mol. Wt.: 535.7 | | |
| micromol | 10 | 10 | | |
| Weight (mg) | 4.30 | 10.71 | | |

Attachment of "adhesion peptide":

Adhesion peptides were synthesized on the alloc-protected lysine. One batch of the library was attached adhesion peptide A, and a second batch with adhesion peptide B.

Adhesion peptide A: (Boc-D-Ala-D-Arg(Pmc)-D-Lys(Boc)-D-Arg(Pmc)-D-Ile-D-Arg(Pmc)-D-Gln(Trt)-Gly-)

Alloc deprotection of lysine residues: The library beads were treated under $N_2$ with 3 eq Pd(PPh$_3$)$_4$ in 10 mL degassed CHCl$_3$ containing 5% HOAc and 2.5% NEM for 2h at RT. The resin was washed with CHCl$_3$ (6x), DMF containing 0.5% sodium diethyl-dithiocarbamat and 0.5% DIPEA (2x), and DMF (10x).

Coupling: The adhesive peptide was synthesized directly (stepwise) on the library beads using the general SPPS coupling procedure.

Alternative method: The purified peptide (Boc-D-Ala-D-Arg(Pmc)-D-Lys(Boc)-D-Arg(Pmc)-D-Ile-D-Arg(Pmc)-D-Gln(Trt)-L-Gly-OH) (SEQ ID NO. 88) (3 eq) was coupled to the lysine NH$_2$ groups using the general SPPS coupling procedure.

Adhesion peptide B: (Fmoc-D-Arg(Pmc)-D-Ile-D-Arg (Pmc)-D-Gln(Trt)-D-Arg(Pmc)-  (SEQ ID NO. 89):

Analogous to synthesis of adhesion peptide A.
Adhesion Peptide B: (Fmoc-D-Arg(Pmc)-D-Gln(Trt)-D-Arg (Pmc)-D-Ile-D-Arg(Pmc)- (SEQ ID NO. 36)

Analogous to synthesis of adhesion peptide A.

Deprotection of Adhesion and Library Peptides

Final deprotection of protecting groups was performed according to the general procedure described above yielding the TCOB library ready for testing Example 5a Preparation of TAT Appended "Tetrapeptide" Library The peptide library of example 4 is modified to include a TAT sequence appended to the C-terminal end of the peptide library in order to enhance the cell permeation properties of the tetrapeptides.

Synthesis of TAT sequence (GGYGRKKRRQRRR; SEQ ID NO. 90) on Val residues.

Method A: Beads (1.00 g) containing FmocPLL-Val and AllocLys(Alloc) (as prepared in example 3) are subjected to stepwise SPPS using the general TBTU protocol giving the sequence FmocGGYGRKKRRQRRR (SEQ ID NO. 90) attached to the photo labile linker (Arg is side chain protected as Pmc. Gln protected as Trt, Lys protected as Boc, and Tyr as $^t$Bu).

Method B: Beads (1.00 g) containing FmocPLL-Val and AllocLys(Alloc) (as prepared in example 3) are coupled to the side chain protected and purified TAT sequence FmocG-GYGRKKRRQRRR (SEQ ID NO. 90) using the general SPPS coupling procedure. Protection of side chains as in method A.

Formation of TAT Appended Tetrapeptide Library

Using the FmocTAT-Val derivatized beads a tetrapeptide library is build according to the description in Example 3. The resulting library is derivatized with the cell adhesive peptide and followingly all protection groups are removed as described in example 4.

Example 5b

Preparation of Tetrapeptide Library with 44,000 Members with Base Labile Adhesion Peptide In certain preferred embodiments it might be advantageous to be able to clear selected beads from both cells and adhesion peptide before either analysis of active compound or further processing. This example describes the synthesis of the above described library on beads where the adhesion peptide is linked to the bead via an HMBA linker.

Synthesis of FmocGly/AllocGly (Ratio ~1:1) Modified PEGA 1900 Beads

PEGA 1900 beads (300-500 µm, 0.24 mmol NH$_2$/g) (4 g, 0.96 mmol~1 eq)) were treated with a 1:1 TBTU coupling mixture of FmocGlyOH (2 eq) and AllocGlyOH (2 eq), NEM (17 eq) and TBTU (3.8 eq). Coupling time 3.5 h. Beads washed 10× with DMF.

Coupling of Holmes Photolinker to the "Core" Fmoc-Glycine

FmocGly/AllocGly beads were standard Fmoc deprotected with 20% piperidine in DMF leaving the Alloc glycine untouched. Then standard TBTU coupling of the Holmes photolinker (4-(1-aminoethyl-2-methoxy-5-nitrophenoxy) butanoic acid) to the deprotected glycine (1 eq=0.48 mmol). After coupling, the beads were washed with DMF and DCM and lyophilized.

Tetrapeptide Library Synthesis on the Photo Linker

Performed analogous to example 4

Alloc Deprotection of Second "Core" Glycine:

The beads from the 20 wells were all combined in a 50 mL syringe and washed with CHCl$_3$ (5×) and with Ar-degassed CHCl$_3$ containing 5% HOAc and 2.5% NEM (5×). A solution of Pd(PPh$_3$)$_4$ (3 eq, 0.72 mmol) in Ar-degassed CHCl$_3$ containing 5% HOAc and 2.5% NEM (10 mL) was added to the beads and after a few minutes bobbling with Ar the syringe was sealed with parafilm and left for 2 h. The beads were washed with CHCl$_3$ (10×), DMF (10×), MeOH (10×), DMF (20% pip) (2×), DMF/10×). Kaiser test was positive.

Attachment of HMBA Linker

According to standard procedure above.

MSNT Coupling of FmocGlyOH

According to standard procedure above.

TBTU Coupling of FmocLys(Fmoc)OH

According to standard procedure above.

Adhesion Peptide Synthesis

After deprotection of the lysine Fmoc groups performed analogous to example 4.

Example 5c

Formation of a "Tetrapeptide" Library Linked Via an Internal Amide Nitrogen

Synthesis of FmocGly/AllocGly (Ratio ~1:1) Modified PEGA 1900 Beads

PEGA 1900 beads (300-500 µm, 0.24 mmol NH$_2$/g) (4 g, 0.96 mmol~1 eq)) were treated with a 1:1 TBTU coupling mixture of FmocGlyOH (2 eq) and AllocGlyOH (2 eq), NEM (17 eq) and TBTU (3.8 eq). Coupling time was 3.5 h. Beads were washed 10× with DMF.

Coupling of Aldehyde Photolinker to the "Core" Fmoc-Glycine.

FmocGly/AllocGly beads were standard Fmoc deprotected with 20% piperidine in DMF leaving the Alloc glycine untouched. Then standard TBTU coupling of the aldehyde photolinker (4-(4-formyl-2-methoxy-5-nitrophenoxy)butanoic acid) to the deprotected glycine (1 eq=0.48 mmol). After coupling, the beads were washed with DMF and DCM and lyophilized.

TABLE 7

5 Phenylethylamines used for reductive amination of aldehyde linker

| 1 | 2 | 3 | 4 | 5 |
|---|---|---|---|---|
| phenethylamine | 4-F-phenethylamine | 3-F-phenethylamine | 3-Cl-phenethylamine | 3-MeO-phenethylamine |
| 121.18 g/mol | 139.17 g/mol | 139.17 g/mol | 155.63 g/mol | 151.21 g/mol |
| d: 0.965 | d: 1.061 | d: 1.066 | d: 1.119 | d: 1.033 |

TABLE 8

Compounds used for BTC coupling

| Well number | 1 | 2 | 3 | 4 |
|---|---|---|---|---|
| Structure | BocHN-pyrrolidine-FmocN-COOH | BocHN-pyrrolidine-FmocN-COOH | BocHN-pyrrolidine-FmocN-COOH | BocHN-pyrrolidine-FmocN-COOH |
| Mw (g/mol) | 452.50 | 452.50 | 452.50 | 452.50 |
| Mol × 10$^6$ | 36 | 36 | 36 | 36 |
| Weight (mg) | 16.3 | 16.3 | 16.3 | 16.3 |
| Well number | 5 | 6 | 7 | 8 |
| Structure | BocHN-pyrrolidine-FmocN-COOH | BocHN-pyrrolidine-FmocN-COOH | BocHN-pyrrolidine-FmocN-COOH | BocHN-pyrrolidine-FmocN-COOH |
| Mw (g/mol) | 452.50 | 452.50 | 452.50 | 452.50 |
| Mol × 10$^6$ | 36 | 36 | 36 | 36 |
| Weight (mg) | 16.3 | 16.3 | 16.3 | 16.3 |

TABLE 8-continued

Compounds used for BTC coupling

| Well number | 9 | 10 | 11 | 12 |
|---|---|---|---|---|
| Structure | BocHN-pyrrolidine-Fmoc-COOH | BocHN-pyrrolidine-Fmoc-COOH | FmocN-pyrrolidine-COOH | FmocN-pyrrolidine-COOH |
| Mw (g/mol) | 452.50 | 452.50 | 337.67 | 337.67 |
| Mol × 10$^6$ | 36 | 36 | 36 | 36 |
| Weight (mg) | 16.3 | 16.3 | 12.1 | 12.1 |

| Well number | 13 | 14 | 15 | 16 |
|---|---|---|---|---|
| Structure | FmocN-azetidine-COOH | piperidine-3-COOH-NFmoc (R/S) | tetrahydroisoquinoline-COOH-NFmoc | FmocHN-cyclopentane-COOH |
| Mw (g/mol) | 323.34 | 351.40 | 399.44 | 351.40 |
| Mol × 10$^6$ | 36 | 36 | 36 | 36 |
| Weight (mg) | 11.6 | 12.7 | 14.4 | 12.7 |

| Well number | 17 | 18 | 19 | 20 |
|---|---|---|---|---|
| Structure | FmocN-piperidine-phenyl-COOH | phenyl-pyrrolidine-COOH-NFmoc | cyclohexyl-FmocHN-COOH | BocHN-cyclohexylmethyl-pyrrolidine-FmocN-COOH |
| Mw (g/mol) | 427.49 | 413.47 | 379.46 | 565.72 |
| Mol × 10$^6$ | 36 | 36 | 36 | 36 |
| Weight (mg) | 15.4 | 14.9 | 13.7 | 20.4 |

TABLE 9

Compounds used for acylation in wells 1-10.

| 1 | 2 | 3 | 4 | 5 |
|---|---|---|---|---|
| cyclopentanecarbonyl chloride | furan-2-carbonyl chloride | phenylacetyl chloride | 4-fluorobenzoyl chloride | cyclohexanecarbonyl chloride |
| Mw: 132.59 d: 1.091 | Mw: 130.53 d: 1.324 | Mw: 154.60 d: 1.167 | Mw: 158.56 d: 1.342 | Mw: 146.62 d: 1.096 |

TABLE 9-continued
Compounds used for acylation in wells 1-10.
| 6 | 7 | 8 | 9 | 10 |
|---|---|---|---|---|
| 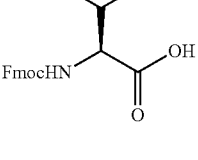 | | | | |
| Mw: 120.58 | Mw: 134.61 | Mw: 106.55 | Mw: 104.54 | Mw: 78.50 |
| d: 0.980 | d: 0.969 | d: 1.017 | d: 1.151 | d: 1.104 |
TABLE 10
Compounds used for TBTU coupling
| Member number | 1 | 2 | 3 | 4 |
|---|---|---|---|---|
| Structure | 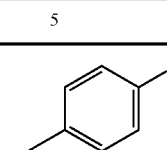 | | | |
| Mw (g/mol) | 353.41 | 379.46 | 393.48 | 411.45 |
| Mol × $10^6$ | 36 | 36 | 36 | 36 |
| Weight (mg) | 12.7 | 13.7 | 14.1 | 14.8 |
| Member number | 5 | 6 | 7 | 8 |
|---|---|---|---|---|
| Structure | | | | |
| Mw (g/mol) | 405.42 | 387.43 | 397.46 | 351.40 |
| Mol × $10^6$ | 36 | 36 | 36 | 36 |
| Weight (mg) | 14.6 | 13.9 | 14.3 | 12.6 |
| Member number | 9 | 10 | 11 | 12 |
|---|---|---|---|---|
| Structure | 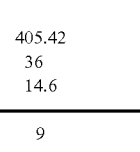 | | | |
| Mw (g/mol) | 353.41 | 477.51 | 425.47 | 596.67 |
| Mol × $10^6$ | 36 | 36 | 36 | 36 |
| Weight (mg) | 12.7 | 17.2 | 15.3 | 21.5 |

TABLE 10-continued

Compounds used for TBTU coupling

| Member number | 13 | 14 | 15 | 16 |
|---|---|---|---|---|
| Structure | FmocHN-C(cyclohexyl)-COOH | FmocN-azetidine-COOH | Fmoc-Gln(Trt)-OH | Fmoc-3,4-dimethoxyPhe-OH |
| Mw (g/mol) | 565.42 | 323.34 | 610.70 | 447.49 |
| Mol × 10$^6$ | 36 | 36 | 36 | 36 |
| Weight (mg) | 20.4 | 11.6 | 22.0 | 16.1 |

| Member number | 17 | 18 | 19 | 20 |
|---|---|---|---|---|
| Structure | Fmoc-Aib-OH | Fmoc-Ser(tBu)-OH | Fmoc-(2-thienyl)Ala-OH | Fmoc-Ala-OH |
| Mw (g/mol) | 325.36 | 383.44 | 393.46 | 311.33 |
| Mol × 10$^6$ | 36 | 36 | 36 | 36 |
| Weight (mg) | 11.7 | 13.8 | 14.2 | 11.2 |

TABLE 11

Compounds used for TBTU coupling of amino acids and acylation with acyl chlorides

| Member number | 1 | 2 | 3 | 4 |
|---|---|---|---|---|
| Structure | N-Me-Boc-Ala-OH | Boc-azetidine-COOH | Boc-D-Ala-OH | Boc-Ala-OH |
| Mw | 203.24 | 201.22 | 189.21 | 189.21 |
| Mol × 10$^6$ | 36 | 36 | 36 | 36 |
| Weight (mg) | 7.3 | 7.2 | 6.8 | 6.8 |

| Member number | 5 | 6 | 7 | 8 |
|---|---|---|---|---|
| Structure | Boc-Abu-OH | Boc-Aib-OH | Boc-Ser(tBu)-OH·DCHA | Boc-D-Ser(tBu)-OH·DCHA |
| Mw (g/mol) | 203.24 | 203.24 | 442.63 | 442.63 |
| Mol × 10$^6$ | 36 | 36 | 36 | 36 |
| Weight (mg) | 7.3 | 7.3 | 15.9 | 15.9 |

| Member number | 9 | 10 | 11 | 12 |
|---|---|---|---|---|
| Structure | Boc-Gly-OH | Boc-Dap(Boc)-OH·DCHA | Boc-Ile-OH | Boc-Leu-OH |

TABLE 11-continued

Compounds used for TBTU coupling of amino acids and acylation with acyl chlorides

| | | | | |
|---|---|---|---|---|
| Mw (g/mol) | 175.18 | 485.66 | 231.29 | 231.29 |
| Mol × 10$^6$ | 36 | 36 | 36 | 36 |
| Weight (mg) | 6.3 | 17.5 | 8.3 | 8.3 |

| Member number | 13 | 14 | 15 | 16 |
|---|---|---|---|---|
| Structure | BocHN-Val-OH | Boc-Pro-OH | t-BuO-Thr(BocHN)-OH | tBu-CH2-C(O)Cl |
| Mw (g/mol) | 217.26 | 215.25 | 275.34 | 134.60 |
| Mol × 10$^6$ | 36 | 36 | 36 | 120 |
| Weight (mg) | 7.8 | 7.7 | 9.9 | 16.2 (0.017 mL) |

| Member number | 17 | 18 | 19 | 20 |
|---|---|---|---|---|
| Structure | iBu-C(O)Cl | cyclopropyl-C(O)Cl | iPr-C(O)Cl | CH3-C(O)Cl |
| Mw (g/mol) | 120.58 | 104.53 | 106.55 | 78.50 |
| Mol × 10$^6$ | 120 | 120 | 120 | 120 |
| Weight (mg) | 14.4 (0.015 mL) | 12.6 (0.011 mL) | 12.8 (0.013 mL) | 9.4 (0.009 mL) |

Library Synthesis:

Step 1, Reductive Amination of Photo Linker Aldehyde:

5 portions of the above beads (0.8 g dry beads) were placed in 5 syringes of 5 mL.

The beads were swollen in DMF and phenylethylamines (see Table 7) were coupled to the free aldehyde on the photolinker by reductive amination as follows: 0.8 g dry beads is 96 μmols~1 eq were pre-treated with the reaction solvent (DMF/HOAc/TEOF/EtOH, 1:1:1:1). Then to each syringe was added one of the five phenylethylamines (20 eq) dissolved in the reaction solvent (400 μL), and the same solvent was added so the beads were covered. After 0.5 h NaBH$_3$CN (20 eq) was added and the beads stirred cautiously until all dissolved. After 1 h another portion of NaBH$_3$CN (20 eq) was added and the mixture left for additional 2 h. The beads were washed with DMF (10×), DCM (10×), MeOH (10% HOAc) (2×), MeOH (10×), DMF (20% pip) (2×), and DMF (10×), DCM (10×). The 5 samples were lyophilized over night.

Step 2, Mix and Split of Phenylethyl Amines:

0.4 g of each of the 5 bead samples from above were swelled in DMF, mixed and transferred to a custom made 20-well library synthesizer such that each well contained approximate equal amounts of beads.

Step 3, BTC Coupling of First Amino Acid:

Total amount of beads=2.0 g~0.24 mmol gives 12 μmol NH/well ~1 eq.

20 BTC-couplings from 11 different amino acids as shown in Table 8 was made as follows: Beads were pre-treated with a 1:1 vol % THF/DIPEA solution for 5 minutes and drained. Of each amino acid in Table 2, 3 eq (36 μmol) was dissolved in dry THF (200 μL) and BTC (1.67 eq) added as 200 μL of a freshly made stock solution in dry THF. Then 2,4,6-collidine (14 eq), as 200 μL of a freshly made stock solution in dry THF, was added and the resulting 20 suspensions left for 5 minutes. Each suspension was added to the respective well and after short mixing the synthesizer was sealed and left over night with gentle shaking. Next morning the beads were washed with THF (10×) and DMF (10×) without mixing the wells.

Step 4, Acylation of Well 1-10:

Beads in well 1-10 were washed with DCM (10×) and Boc deprotected with 30% TFA in DCM followed by wash with DCM (10×), DCM (5% DIPEA), DMF, and DCM (10×). From each of the 10 acyl chlorides in Table 9 was made a solution of 10 eq acyl chloride (120 μmol) and DIPEA (20 eq) in dry DCM (400 μL) containing catalytic amounts of DMAP. The resulting solutions were added to well 1-10 and left with gentle shaking for 1 h. The reaction was repeated. After end reactions the beads were washed with DCM (10×), and DMF (10×).

Step 5, Removal of Fmoc Protection Groups:

Well 1-20 were standard Fmoc deprotected, followed by wash with DMF (10×).

Step 6, Mix and Split of the 20 Wells

The content of the 20 wells was thoroughly mixed and re-distributed equally into the wells.

Step 7, Coupling of Second Amino Acid (20 Amino Acids):

To each well was coupled an amino acid according to Table 10 by a standard TBTU coupling. Coupling time 5 h. After end reaction the beads were washed with DMF (10×).

Step 8, Coupling of Third Amino Acid/Acyl Chloride (15 Amino Acids-5 Acyl Chlorides):

The beads in all wells were standard Fmoc deprotected and for well 1-15 standard TBTU coupled with the Boc-protected amino acids in Table 11. For wells 16-20 the beads were first washed with DCM (10×) and the N-terminal amines acylated with the five acyl chlorides listed in Table 11 (entry 16-20) analogous to step 4. After couplings all wells were washed with DMF (10×).

Step 9, Alloc Deprotection of Second "Core" Glycine:

The beads from the 20 wells were all combined in a 50 mL syringe and washed with CHCl$_3$ (5×) and with Ar-degassed CHCl$_3$ containing 5% HOAc and 2.5% NEM (5×). A solution of Pd(PPh$_3$)$_4$ (3 eq, 0.72 mmol) in Ar-degassed CHCl$_3$ containing 5% HOAc and 2.5% NEM (10 mL) was added to the beads and after bobbling a few minutes with Ar the syringe was sealed with parafilm and left for 2 h. The beads were washed with CHCl$_3$ (10×), DMF (10×), DMF (5% DIPEA, 5% sodium diethyldithiocarbamate) (5×), MeOH (10×), DMF DMF (20×). Kaiser test was positive.

Step 10, Attachment of HMBA Linker:
According to the standard procedure above.

Step 11, MSNT Coupling of FmocGlyOH:
According to the standard procedure above.

Step 12, TBTU Coupling of FmocLys(Fmoc)OH
According to the standard procedure above.

Step 13, Attachment of Adhesion Peptides
Adhesion peptides were synthesized on the Fmoc-protected lysine such that the final beads had two adhesion peptides pr. library molecule. One batch of the library was attached adhesion peptide A, and a second batch with adhesion peptide B.

Adhesion peptide A: (Boc-D-Ala-D-Arg(Pmc)-D-Lys (Boc)-D-Arg(Pmc)-D-Ile-D-Arg(Pmc)-D-Gln(Trt)-Gly- (SEQ ID NO. 88):

Fmoc deprotection of lysine residues: According to the standard procedure.

Coupling: The adhesive peptide was synthesized directly (stepwise) on the library beads using the general SPPS coupling procedure.

Alternative method: The purified peptide (Boc-D-Ala-D-Arg(Pmc)-D-Lys(Boc)-D-Arg(Pmc)D-Ile-D-Arg(Pmc)-D-Gln(Trt)-L-Gly-OH) (SEQ ID NO. 88) (3 eq) was coupled to the lysine NH$_2$ groups using the general SPPS coupling procedure.

Adhesion peptide B: (Fmoc-D-Arg(Pmc)-D-Gln(Trt)-D-Arg(Pmc)-D-Ile-D-Arg(Pmc)-: (SEQ ID: 35)

Analogous to synthesis of adhesion peptide A.

Deprotection of Adhesion and Library Peptides
Final deprotection of protecting groups was performed according to the general procedure described above yielding the TCOB libraries ready for testing.

Example 6

Partial Release of Library Compounds from Beads

The library beads of Examples 4 and 5 are swelled in the assay medium and illuminated with an OMNILUX E-40 (400 W UV lamp, 365 nm, #89514005, Steinigke Showtechnic GmbH, Germany) for 15 min. The beads could be placed in any environment (for example plates, wells etc. used for the assays). This treatment releases appropriate amounts of active peptide for assay use and the beads withholds enough active peptide for subsequent identification.

Example 7

Clearance of Cells and Adhesion Peptide

A portion of the library beads with cells attached were drained from medium and treated with a 0.1 M NaOH solution for 1 h. Beads were gently spinned down and the supernatant removed. The beads were washed with water (10×) to ensure complete removal of cells and proteins.

Example 8

Functional assay for identification of compounds that stimulate a Gs coupled signal transduction pathway (Cre-GFP reporter assay detected with a Fluorescence Activated Bead Sorter)

Figure 3:
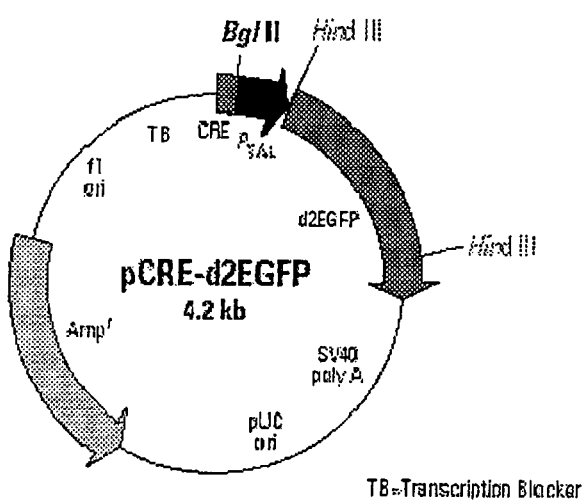
FIG. 3 illustrates a plasmid map of pCRE-d2EGFP

Cre-GFP:
Cre-GFP is commercially available from clontech (pCred2eGFP) The vector contains three copies of Cre-binding sequence fused to a TATA-like promoter. The vector is holding a neomycin resistance gene. A map of the vector is shown in FIG. 3. MC4R:

PCR amplified MC4R encoding DNA is introduced into the gateway Entry Vector (pENTR) by topoisomarase-mediated ligation. The DNA is subsequently recombined into Destination Vector pDEST12.2. (pDEST12.2MC4R)

Cell Line Establishment:
HEK cells are transfected with pDEST1.2.2MC4R using standard procedure for Fugene6 transfection. Cells are put under G418 selection for 4 weeks to obtain a cell line stably expressing MC4R.

The U2OS cell line stably expressing the human MC4R (melanocortin4 receptor) is further transfected with Cre-GFP the day before culturing them on PEGA beads displaying adhesion peptide and respectively 1) Negative control (PEGA beads with adhesion peptide, but no library compound), 2) Positive control (PEGA beads with adhesion peptide but no library compound) and 3) Library compounds. The three cultures are handled separately in each their culture flask.

Bead/Cell Preparation:
Cells are trypsinized and mixed with the PEGA beads in growth medium (DMEM containing 10% FCS, in the proportion 4000 cells/bead and app. 50 ml growth medium/5000 beads.

1) Positive control: 50 ml Growth medium+5000 positive control beads+2×10E7 cells+10 µM Forskolin.
2) Negative control: 50 ml Growth medium+5000 negative control beads+2×10E7 cells.
3) Screening library (eg. 100.000 compounds): 1000 ml Growth medium+100.000 library beads+4×10E8 cells was illuminated with an OMNILUX E-40 UV light (365 nm) for 30 min for obtaining a partial release of the library compounds (as described in example 6) The three culture flasks are placed on a Magnetic stirring platform (Techne) designed for cell culture in suspension and incubated at 37°, 5% CO2 for 16-24 hrs using spinning interval 30 rpm, 3 min stirring, 10 min pause.

Beads, now covered with cells, are allowed to sediment for 10 min (no centrifugation needed) and the growth medium is removed using a 50 ml pipette. 10 ml 99% EtOH per 5000 beads is added, mixed gently and left for 15 min. Beads are washed w. 10 ml PBS/5000 beads×3 by allowing sedimentation for 10 min between each wash. Cells are now preserved and fixed to the beads Bead Sorting:
A Fluorescence Activated Bead Sorter (FABS) equipped with a multiline Argon laser 488 nm excitation line and 500-650 nm emission filter and sorting capability into 96 well plate is used to identify and isolate positive hit beads.

The FABS is calibrated to identify and isolate positive hit beads (increased GFP fluorescence) by determining the dynamic range of the assay using positive control beads prepared as described above as Smax (maximum response) and negative control beads comprising only cell adhesion peptide as 5 min (minimum response). A cut off at 30% response compared to negative control beads is set as threshold for a positive hit bead.

Positive hits are separated into each their well of a 96 well plate and are hereafter ready for compound elucidation, re-synthesis and re-test as well as test for effects in other assays.

Example 9

Functional Assay for Identification of Compounds that Inhibit a Gq Coupled Receptor (Muscarinic M1) Signal Transduction Pathway (Ca++ Mobilization using Fluo-4)

Ca++ Antagonist Assay:

This assay is designed to identify muscarinic M1 antagonist compounds. The read out is changes in intracellular Ca++ conc. detected using the Fluo-4 probe from Molecular probes (see description elsewhere). Positive hits are compounds that inhibit Carbacol (muscarinic M1 agonist) induced increase in intracellular Ca++.

U2OS cells are transfected with Muscarinic M1 receptor using standard procedure for Fugene6 transfection. Cells are put under zeocin selection for 4 weeks to obtain a cell line stably expressing the Muscarinic M1 receptor.

U2OS cells expressing the Muscarinic M1 receptor are cultured on PEGA beads displaying adhesion peptide and respectively 1) Negative control (Beads comprising only cell adhesion compound), 2) Positive control (beads comprising cell adhesion compound and Atropine) and 3) Library compounds. The three cultures are handled separately in each their culture flask.

Bead/Cell Preparation:

Cells are trypsinized and mixed with beads in DMEM containing 10% FCS in the proportion 4000 cells/bead and app. 50 ml growth medium/5000 beads.

1) Positive control: 50 ml Growth medium+5000 positive control beads+2×10E7 cells.
2) Negative control: 50 ml Growth medium+5000 negative control beads+2×10E7 cells.
3) Screening library (eg. 100.000 compounds): 1000 ml Growth medium+100.000 library beads+4×10E8 cells was illuminated with an OMNILUX E-40 UV light (365 nm) for 30 min for obtaining a partial release of the library compounds (as described in example 6)

The three culture flasks are placed on a Magnetic stirring platform (Techne) designed for cell culture in suspension and incubated at 37°, 5% CO2 for 16-24 hrs using spinning interval 30 rpm, 3 min stirring, 10 min pause.

Measurement of changes in the cytoplasmic free calcium concentration $[Ca^{2+}]_i$ Beads, now covered with cells, are allowed to sediment for 10 min (no centrifugation needed) and the growth medium is removed using a 50 ml pipette. 10 ml Krebs Ringer buffer (KRW; KrebsRingerWollheim, pH 7.4: NaCl 0.14 M, KCL 3.6 mM, $NaH_2PO_4$, $H_2O$ 0.5 mM, $MgSO_4$, $7H_2O$ 0.5 mM, $NaHCO_3$, $2H_2O$ 1.5 mM, D-Glucose 6 mM, $CaCl_2$ 1.5 mM, HEPES 10 mM) added 1 uM Fluo-4 (Molecular Probes F-14201)+0.02% Pluronic (Molecular Probes F-127) per 5000 beads is added, mixed gently and cells/beads are incubated at 37° C. for 30 min. Beads are hereafter washed w. 10 ml KRW/5000 beads×3 by allowing sedimentation for 10 min between each wash. The Fluo-4 loaded cells are now ready for detection of changes in $[Ca^{2+}]_i$.

The fluorescence is monitored in either a Fluorescence Activated Bead Sorter (FABS) (COPAS from Union Biometrica, US) that is equipped with multiple laser excitation lines (476 nm, 483 nm, 488 nm, 496 nm, 514 nm, 520 nm, 568 nm, 647 nm, 676 nm) or a fluorescence plate-reader (Polarstar Optima from BMG Labtech, Germany) that is equipped with a flash Xenon blitz lamp. Fluo4 fluorescence is detected in FABS by exciting with 488 nm and collecting the emitted light on to a PMT through a 530±30 nm emission filter, and on the plate-reader the cells were excited through a 490±5 nm excitation filter and the emission collected through a 510±5 nm emission filter. For calculation of the exact $[Ca^{2+}]_i$ the fluorescence intensity was converted to $[Ca^{2+}]_i$ by using the equation $[Ca^{2+}]_i = K_D[(F-F_{min})/(F_{max}-F)]$ where the dissociation constant $K_D$ is 345 nM, F is fluorescence intensity, $F_{min}$ is total fluorescence in the absence of $Ca^{2+}$ and $F_{max}$ is total fluorescence when Fluo3 is saturated with $Ca^{2+}$. To obtain $F_{min}$ the cells were pre-incubated in a calcium low buffer (pH 7.4: NaCl 0.14 M, KCL 3.6 mM, $NaH_2PO_4$, $H_2O$ 0.5 mM, $MgSO_4$, $7H_2O$ 0.5 mM, $NaHCO_3$, $2H_2O$ 1.5 mM, D-Glucose 6 mM, EGTA 1.5 mM, HEPES 10 mM) and was challenged with 1 uM ionomycin immediately before the fluorescence detection. Similarly $F_{max}$ was obtained by suspending the cells in a calcium saturated buffer (pH 7.4: NaCl 0.14 M, KCL 3.6 mM, $NaH_2PO_4$, $H_2O$ 0.5 mM, $MgSO_4$, $7H_2O$ 0.5 mM, $NaHCO_3$, $2H_2O$ 1.5 mM, D-Glucose 6 mM, $CaCl_2$ 1.5 mM, HEPES 10 mM) and challenged with 1 μM ionomycin immediately before detection.

In several of our screening assay we do not use exact ion $[Ca^{2+}]_i$, but express the response of screening compounds as relative to control compounds (see below).

Bead Sorting for Fluo-4 Signal:

A Fluorescence Activated Bead Sorter (FABS) equipped with 488 nm laser excitation line and 528-572 nm emission filter and injection capability is used to identify and isolate positive hit beads (=inhibition of Carbachol induced Ca++ response=decreased fluorescence compared to negative control).

The FABS is calibrated to identify and isolate positive hit beads by determining the dynamic range of the assay using positive control beads as Smax (maximum inhibition=minimal fluorescence) and negative control beads as Smin (minimum inhibition=maximal fluorescence). Carbacol 1 uM is injected into the flow stream resulting in an increase in fluorescence for negative control beads and an unchanged or minor increase in fluorescence for positive control beads. A cut off at 30% inhibition compared to negative control beads is set as threshold for a positive hit bead.

Positive hits are separated into each their well of a 96 well plate and are hereafter ready for compound elucidation, re-synthesis and re-test as well as test for effects in other assays.

Example 10

Functional assay for identification of compounds that stimulate a Gs coupled signal transduction pathway (Cre-GFP reporter assay detected with fluorescence plate reader or fluorescence imaging equipment)

Cre-GFP:

Cre-GFP is commercially available from clontech (pCre-d2eGFP) The vector contains three copies of Cre-binding sequence fused to a TATA-like promoter. The vector is holding a neomycin resistance gene. A map of the vector is shown in FIG. 3.

MC4R:

PCR amplified MC4R encoding DNA is introduced into the gateway Entry Vector (pENTR) by topoisomarase-mediated ligation. The DNA was subsequently recombined into Destination Vector pDEST12.2. (pDEST12.2MC4R)

Cell Line Establishment:

U2OS cells are transfected with pDEST1.2.2MC4R using standard procedure for Fugene6 transfection. Cells were put under G418 selection for 4 weeks to obtain a cell line stably expressing the MC4R.

The U2OS cell line stably expressing the human MC4R (melanocortin4 receptor) is further transfected with Cre-GFP the day before culturing them on PEGA beads displaying adhesion peptide and respectively 1) Negative control (PEGA beads with adhesion peptide, but no library compound), 2) Positive control (PEGA beads of example 2) and 3) Library compounds. The three cultures are handled separately in each their culture flask.

Bead/Cell Preparation:

Cells are trypsinized and mixed with the PEGA beads in growth medium (DMEM containing 10% FCS, in the proportion 4000 cells/bead and app. 50 ml growth medium/5000 beads.
1) Positive control: 50 ml Growth medium+5000 positive control beads+2×10E7 cells.
2) Negative control: 50 ml Growth medium+5000 negative control beads+2×10E7 cells.
3) Screening library (eg. 100.000 compounds): 1000 ml Growth medium+100.000 library beads+4×10E8 cells was illuminated with an OMNILUX E-40 UV light (365 nm) for 30 min for obtaining a partial release of the library compounds (as described in example 6)

The three culture flasks are placed on a Magnetic stirring platform (Techne) designed for cell culture in suspension and incubated at 37°, 5% CO2 for 16-24 hrs using spinning interval 30 rpm, 3 min stirring, 10 min pause.

Beads, now covered with cells, are allowed to sediment for 10 min (no centrifugation needed) and the growth medium is removed using a 50 ml pipette. 10 ml 99% EtOH per 5000 beads is added, mixed gently and left for 15 min. Beads are washed w. 10 ml PBS/5000 beads×3 by allowing sedimentation for 10 min between each wash. Cells are now preserved and fixed to the beads.

Plate Reader Assay:

Control beads as well as library beads are seeded in 384 well black plates (eg. Nunc) with clear bottom app. 20 beads per well. Positive and negative controls are placed in dedicated wells in 2 times 4 replicates in each end of the plate. Negative control=20 negative control beads, positive control=one positive control bead+19 negative control beads. The plates are measured in a fluorescence plate reader (PolarStar Optima from BMG) using 490+−6 nm excitation filter and 510+−5 nm emission filter. Positive control wells are used to determine Smax (maximum response)=100% activity and negative control wells to determine Smin (minimum response)=0% activity. Beads from wells showing activity >30% are collected in a tube for re-seeding in a new 384 well plate, this time having one bead per well. Smin=one negative control bead and Smax=one positive control bead. Read plates in plate reader and identify hits beads using same procedure as described above.

Image Acquisition and Analysis:

Control beads as well as library beads are seeded in 384 well black plates (eg. Nunc) with clear bottom app. 20 beads per well. Positive and negative control beads are placed in dedicated wells in 2 times 4 replicates in each end of the plate. Negative control=20 negative control beads, positive control=one positive control bead+19 negative control beads. Plates are placed on a microscope (Zeiss Axiovert 200M) equipped with filters allowing fluorescence imaging of eGFP (excitation: 490 nm, emission: 510 nm), 10× objective and motorized stage. One image is acquired for each well followed by image analysis (Metamorph) for identification of hit beads (green). Beads from hit wells are seeded in a new 384 well plate this time having one bead per well. Smin=one negative control bead and Smax=one positive control bead. Image acquisition and analysis described above is repeated and final hit beads are identified.

Alternatively, approximately 5000 beads are seeded into Lab-Tech Chambered Coverglass System (#155361; Nalge Nunc International), imaging acquisition analysis is performed using the fluorescence equipment described above, and individual beads that display the required fluorescence properties are isolated using a micromanipulator system (Eppendorf Injectman NK).

Example 11

Assay for Identification of Protein-Protein Interaction (ML-IAP:Smac) Modulators The present assay that is based on the principle: Bioluminescence Resonance Energy Transfer (BRET$^2$), commercially available from Perkin Elmer. One of two interacting proteins is fused to a bioluminescent donor (luciferase, Rluc) and the other protein is fused to a fluorescent acceptor (GFP). Melanoma Inhibitor of Apoptosis Protein (ML-IAP) Probe:

The probe is constructed by PCR amplification of the ML-IAP (GenBank Accession number: NM_139317 (alpha form); NM_022161 (beta form) (the accession number refer to the sequence available on 25 May 2005) from human cDNA libraries (Marathon-Ready cDNA Library of human kidney cell line and a human fetal brain cell line, Clontech Laboratories, Inc.) using the primers livin-F1 (5'-CCA GTG TTC CCT CCA TGG GAC CTA A-3') (SEQ ID 71) and livin-R1 (5'-TAA GCC ATC CCC CAC GCC AAG-3') (SEQ ID 72). The ML-IAP cDNA gene fragments are further modified to contain restriction sites by PCR amplification using the primers Livin-F3 (5'-GAT AAG CTT CCA GTG TTC CCT CCA TGG GA-3') (SEQ ID 73), Livin-R3 (5'-TAT GGA TCC AAG GTG CGC ACG CGG CT-3') (SEQ ID 74), and Livin-F4 (5'-GAG AAT TCT CCT AAA GAC AGT GCC AAG TG-3') (SEQ ID 75) for amplification of full-length ML-IAP. The primers Livin-BIR-F1 (5'-CAT GGTACC ATG ACA GAG GAG GAA GAG GAG-3') (SEQ ID 76) and Livin-BIR-R1 (5'-GC TGG ATC CGG GTC CCA GGA GCC CAG-3') (SEQ ID 77) are used for amplification of the BIR domain of ML-IAP. The restriction enzyme-treated amplificons are ligated in the BRET2 vectors (obtained from Perkin Elmer, Inc.) to produce N- and C-terminal in-frame fusions to GFP and Rluc.

Smac Probe:

The probe is constructed by ligating restriction enzyme treated PCR amplification products of the cDNA for human Smac (GenBank Accession NM_019887 (variant 1); NM_138929 (variant 3)) in to the BRET2 vectors (obtained from Perkin Elmer, Inc.) to produce C-terminal in-frame fusions to GFP and Rluc, respectively. The following primers are used for PCR: Smac-F1 (5'-GCG CTG CAC AAT GGC GGC TCT-3') (SEQ ID 78), Smac-R1 (5'-GCA CTC ACA GCT CAC AAA GGC GTC T-3') (SEQ ID 79), Smac-F3 (5'-GAT GGT ACC CGC TGC ACA ATG GCG GCT CT-3') (SEQ ID 80), and Smac-R3 (5'-CGT GGA TCC TCA CGC AGG TAG GCC TCC-3') (SEQ ID 81). Cytosolic expression of biologically Smac may be achieved by constructing an ubiquitin-smac fusion as described by Allison M. Hunter, Dan Kottachchi, Jennifer Lewis, Colin S. Duckett, Robert G. Korneluk, and P. Liston. A Novel Ubiquitin Fusion System Bypasses the Mitochondria and Generates Biologically Active Smac/DIABLO. J. Biol. Chem. 278 (9):7494-7499, 2003.

Cell Line Establishment:

Cells are co-transfected with the BRET fusions of ML-IAP and Smac using standard procedure for Fugene6 transfection. Cells are put under G418 and zeocin selection for 4 weeks to obtain a cell line stably expressing the two genes.

Selection of Stable Cells:

The HeLa cell line stably expressing both probes are sorted into a microtitre plate (one cell per well) for high GFP fluorescence using a Fluorescence Activated Cell Sorter. The sorted cells are grown for a week, and split into a plate that is optimized for bio-luminescence. Final cell-clones are selected, after addition of the luciferase substrate, Deep-BlueC (Perkin Elmer), for high luminescence (detected with a PolarStar, BMG).

Bead/Cell Preparation:

HeLa/mammalian cells are cultured on PEGA beads displaying adhesion peptide and respectively 1) Negative control (PEGA beads with adhesion peptide, and a compound with no activity as the library component), 2) Positive control (PEGA beads with adhesion peptide, and a control compound, which disrupts the ML-IAP:Smac interaction e.g. the compound of Example 20 of WO2004/005248, and 3) Library compounds (PEGA beads with adhesion peptide, and screening compounds prepared as described in example 5b or 5c). The three cultures are handled separately in each their culture flask.

Cells are trypsinized and mixed with the PEGA beads in growth medium (DMEM containing 10% FCS, in the proportion 4000 cells/bead and app. 50 ml growth medium/5000 beads. Culture flasks are placed on a Magnetic stirring platform (Techne) designed for cell culture in suspension and incubated at 37°, 5% $CO_2$ for 16-24 hrs using spinning interval 30 rpm, 3 min stirring, 10 min pause. Alternatively, the culture flasks are gently rocked a few times.

Cell-Coated Beads are Treated as Follows:
1) Positive control (low BRET signal): 50 ml Growth medium+approx. 5000 cell-coated control beads.
2) Negative control (high BRET signal): 50 ml Growth medium+approx. 5000 cell-coated control beads
3) Screening library (eg. 100.000 compounds): 1000 ml Growth medium+approx. 100.000 cell-coated library beads.

The cell-coated beads are transferred to assay buffer (either KRW (Krebs Ringer Wollheim) or PBS (phosphate buffered saline) and illuminated with UV light (365 nm) for 2-20 min for obtaining a partial release of the library compounds (as described in example 6). The illuminated beads are further incubated at 37°, 5% $CO_2$ for 15 min. Beads, now covered with cells, are allowed to sediment for 10 min (no centrifugation needed) and the growth medium is removed using a 50 ml pipette.

Positive beads may be indentified by analysing individual beads in a BRET-compatible microplate reader using 410-80 (370-450 nm) and 515-30 (500-530 nm) bandpass filters for dual emission measurements of Rluc-luminescence and GFP-fluorescence, respectively. The luciferase substrate, DeepBlueC, is added by an on-board injector in the microplate reader. The BRET-signal for the protein-protein interaction is calculated as the ratio of emission at 515 nm and emission at 410 nm.

Alternatively Positive Beads May be Identified by Bead Sorting:

A Fluorescence Activated Bead Sorter (FABS) equipped with filters for BRET detection and sorting capability into 96 well plate is used to identify and isolate positive hit beads.

The luciferase substrate, DeepBlueC is injected into the flow stream to emit luciferase-mediated luminescence.

The FABS is calibrated to identify and isolate positive hit beads (decreased BRET signal) by determining the dynamic range of the assay using positive control beads prepared as described in above as Smax (maximum response) and negative control beads comprising only cell adhesion peptide as Smin (minimum response).

Positive hits are separated into each their well of a 96 well plate and are hereafter ready for compound elucidation, re-synthesis and re-test as well as test for effects in other assays.

Example 12

Caspase Activity Assay

Inhibitor of apoptosis proteins (IAPs) interact with caspases to inhibit their activation and thereby cause a repression of apoptosis. We seek to identify compounds, which can bind to IAP with a higher affinity than caspase and, in turn, relieve IAP-mediated caspase-inhibition. A screening assay is established that measures caspase activation in response to an apoptosis inducing signal (e.g. staurosporine, STS) and in the presence of library compounds with putative IAP-binding activity.

The assay is based on measurements of caspase activity in whole mammalian cells (HeLa/MCF-7/MeWo), preferably HeLa/SK-MeI28 cultured on PEGA beads displaying adhesion peptide and respectively 1) Negative control (PEGA beads with adhesion peptide, and a compound with no activity as the library component), 2) Positive control (PEGA beads with adhesion peptide, and a control peptide that disrupts the ML-IAP:Smac interaction prepared as described in example 3 and 3) Library compounds (PEGA beads with adhesion peptide, and screening compounds prepared as described in example 5b or 5c). The three cultures are handled separately in each their culture flask.

Caspase activity is measured in bead-attached whole cells by incubating the cells with a fluorogenic caspase substrate with a quenching leaving group, e.g. DEVD-Rh1 10-C8 or the CellProbe HT Caspase 3/7 Whole Cell Assay, Beckman Coulter, Inc.). A fluorogenic counter stain with different emission properties is applied to correct for cellmass content on the individual beads.

Caspase substrate (DEVD-R-C8) is described in the following publication: Sui Xiong Cai, Han Zhong Zhang, John Guastella, John Drewe, Wu Yang, and Eckard Weber. Design and synthesis of Rhodamine 110 derivative and Caspase-3 substrate for enzyme and cell-based fluorescent assay. Bioorganic & Medicinal Chemistry Letters 11 (1):39-42, 2001 and in the patent: U.S. Pat. No. 6,342,611 B1 (Jan. 29, 2002, Cytovia, Inc. San Diego, Calif.)

Bead/Cell Preparation:

Cells are trypsinized and mixed with the PEGA beads in growth medium (DMEM containing 10% FCS, in the proportion 4000 cells/bead and app. 50 ml growth medium/5000 beads. The beads/cells are placed in three culture flasks and placed on a Magnetic stirring platform (Techne) designed for cell culture in suspension incubated at 37°, 5% CO2 for 16-24 hours using spinning interval 30 rpm, 3 min stirring, 10 min pause.

Cell-Coated Beads are Treated as Follows:
1) Positive control: 50 ml Growth medium+approx. 5000 Positive control beads.
2) Negative control: 50 ml Growth medium+approx. 5000 Negative control beads.
3) Screening library (eg. 100.000 compounds): 1000 ml Growth medium+approx. 100.000 cell-coated Library compound beads.

Screening Procedure:

The cell-coated beads are transferred to assay buffer (KRW or PBS and illuminated with UV light (365 nm) for 30 min for obtaining a partial release of the library compounds (as described in example 6). The three culture flasks are placed on a Magnetic stirring platform (Techne) designed for cell culture in suspension and incubated at 37°, 5% $CO_2$ for 3 to 6 hrs.

The beads are then allowed to sediment for 10 min (no centrifugation needed) and the growth medium is removed using a 50 ml pipette. 1 ml medium containing the fluorogenic caspase substrate and reagent buffer is added to the beads. The beads are incubated without stirring at 37°, 5% $CO_2$ for 0.5-5 hours. The beads are then fixed by treatment with 10 ml 99% EtOH per 5000 beads, gentle mixing whereafter they are left for 15 min. Beads are washed w. 10 ml PBS/5000 beads×3 by allowing sedimentation for 10 min between each wash. Alternatively, beads may be fixed with paraformaldehyde, acetone or zinc-based fixatives. Cells are now preserved and fixed to the beads.

Bead Sorting:

The beads are analysed in a fashion similar to the procedure described in example 11. The Fluorescence Activated Bead Sorter (FABS) is equipped with 488 nm excitation filters and 500-550 nm emission filter for rhodamine-110 measurements and sorting capability into 96 well plate is used to identify and isolate positive hit beads.

The FABS is calibrated to identify and isolate positive hit beads (increased caspase activity) by determining the dynamic range of the assay using positive control beads with apoptosis induced cells to determine the Smax (maximum response) and negative control beads with uninduced cells as Smin (minimum response).

Positive hits are separated into each their well of a 96 well plate and are hereafter ready for compound elucidation, re-synthesis and re-test as well as test for effects in other assays.

Microscopy:

An alternative to FABS-based selection of positive hit beads is epifluorescence microscopy using standard FITC filters (excitation 480±15 nm, emission 535±20 nm) for visualization of rhodamine 110 fluorescence. The microscope is equipped with micromanipulators for extraction of positive hit beads.

Example 12b

Detection of Caspase Activity Using Proximity Ligation-Based Assay

Caspase activity is detected with an assay based on the proximity ligation technology described by S. Fredriksson, M. Gullberg, J. Jarvius, C. Olsson, K. Pietras, S. M. Gustafsdottir, A. Ostman, and U. Landegren. Protein detection using proximity-dependent DNA ligation assays. Nat. Biotechnol. 20 (5):473-477, 2002. This assay allows direct detection of both active caspases and cleaved caspase substrates for example PAPR. Furthermore, the assay can be applied to fixed samples of primary tissue.

We have developed the proximity ligationtechnique to emcompass a high volume discovery platform that allow identification of primary hit compounds in a screening system that because of the ability to conduct the screening in primary cells closely resembles the conditions observed directly in the patient.

The assay employs two antibodies, an antibody specific for cleaved caspase-3 and an antibody for recognizing both the pro-enzyme and the cleaved form of caspase-3. Both antibodies are conjugated with an oligo nucleotide. Coordinated and proximal binding of the two antibodies to an activated caspase allows hybridisation and ligation of DNA probes which can be amplified by rolling circle amplification using fluorescently labelled oligonucleotides or molecular beacons. The quantitative incorporation of a fluorescence label may thus be done like in quantitative real-time PCR. Detection and selection of beads with a positive fluorescence signal is conducted either with the Fluorescence-Activated-Bead-Sorter or a fluorescence microscope or a plate reader.

Example 13

Identification of Compound

Figure 5:
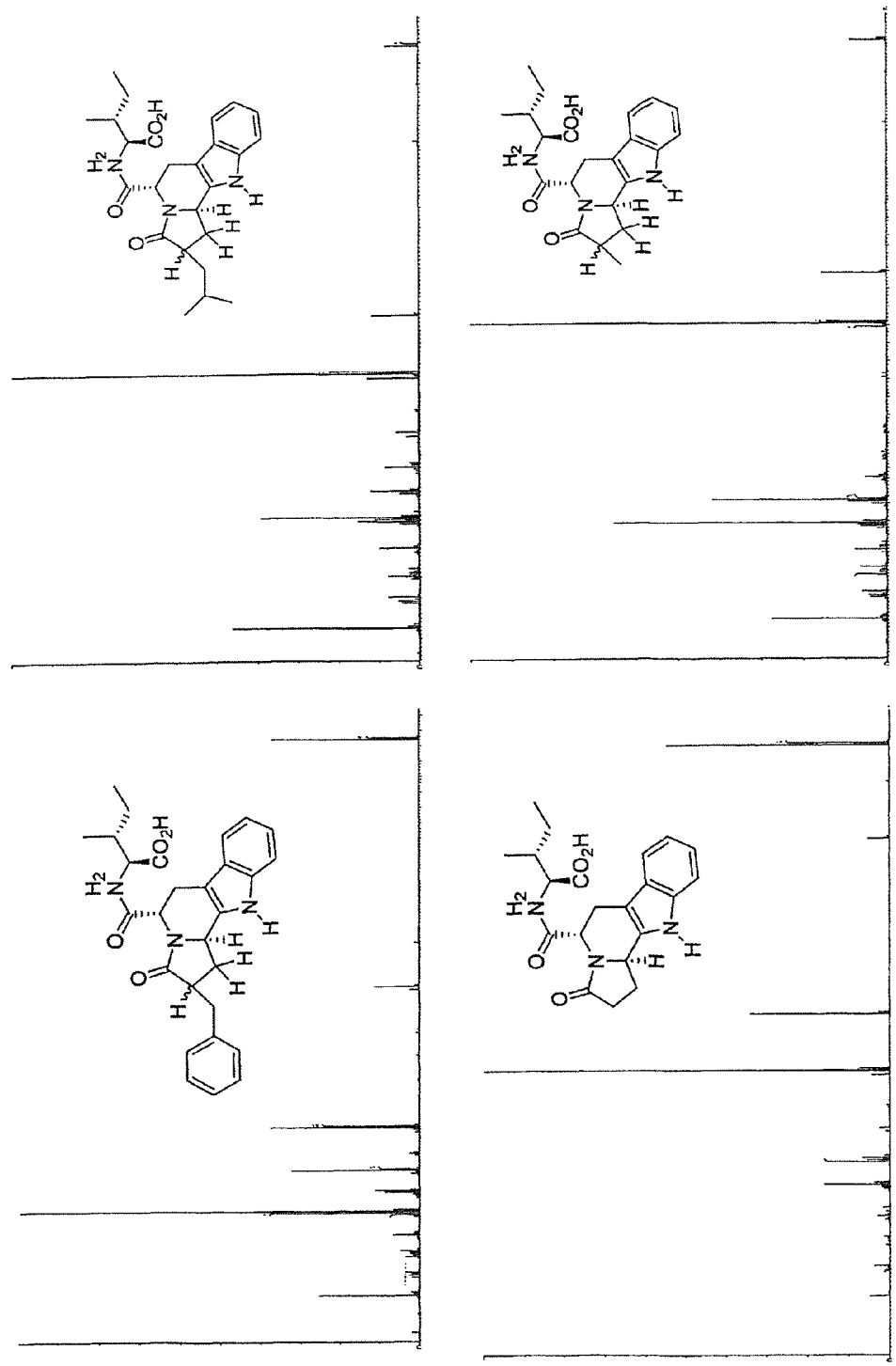
FIG. 5 illustrates spectra and structure determination by accurate mass differences from single beads
Figure 6:
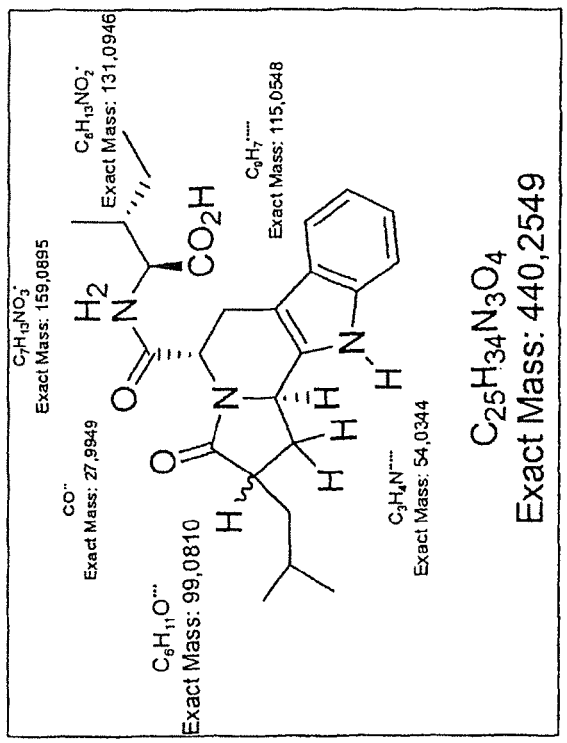
FIG. 6 illustrates structure determination by accurate mass differences from single beads
Figure 7:
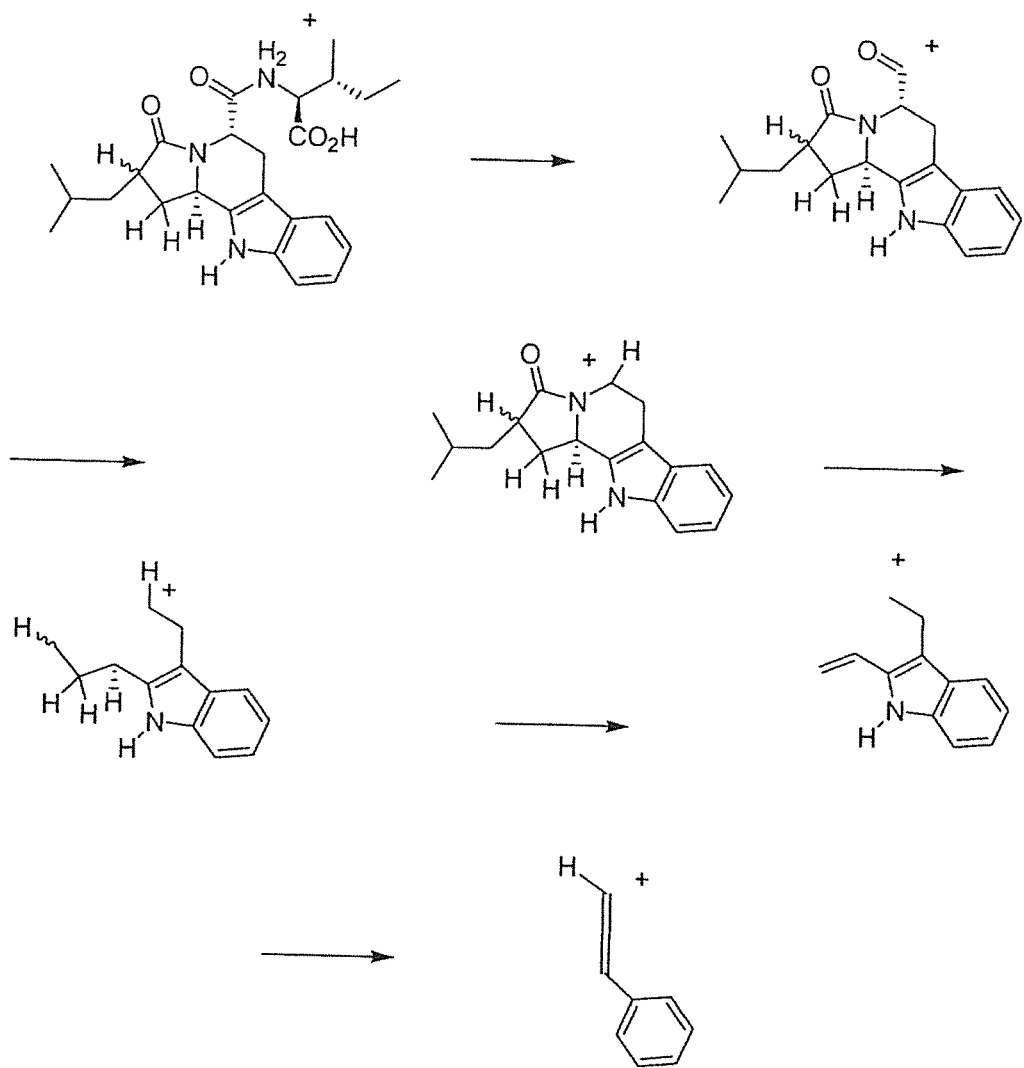
FIG. 7 illustrates a fragmentation pathway
Figure 8:
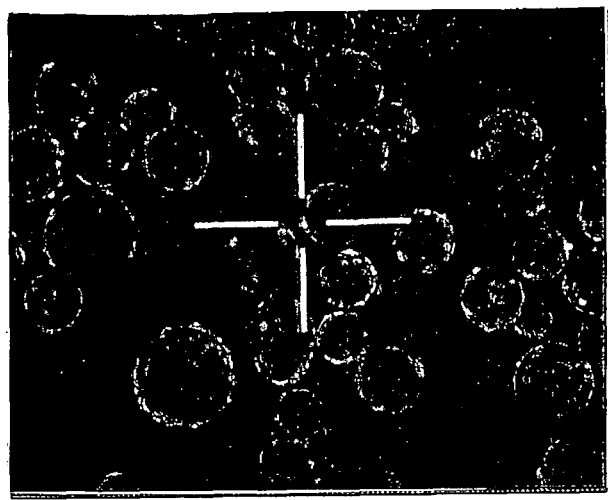
FIG. 8 illustrates examples of an adhesion peptide displaying bead covered with cells (U2OS).
Figure 8:
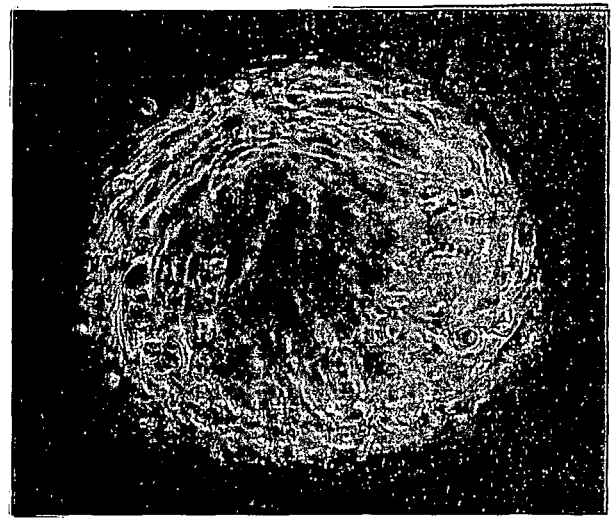

Once a resin bead is selected, the cells may be cleared off the beads either by extensive washing or in case of HMBA-linked adhesion peptides by treatment with 0.1 M NaOH followed by washing (example 7). The library compound comprised within the bead may then be identified. Selected bead(s) are washed and swelled in a small drop of pure water and irradiated for 30 min. with an OMNILUX E-40 (400 W UV lamp, 365 nm, #89514005, Steinigke Showtechnic GmbH, Germany). The compound is identified with advanced mass spectrometry combined with single bead and/or nano-scale NMR techniques. For example advanced MS may be ES MS-MS analysis on a MicroMass QTOF Global Ultima mass spectrometer (mobile phase 50% $CH_3CN$ (aq), 0.1 μL/min) employing a linear ramping of the collision energy. The spectra are analyzed by generating the exact mass differences between fragment ions and tabulated to provide the fragmentation pathway and from that the structure of the compound released from the selected bead is elucidated. Examples of spectra, mass differences and fragmentation pathways are given in FIGS. 5 to 7.

Abbreviations

HGF: Hepatocyte Growth Factor
NGF: Nerve Growth Factor
PDGF: Platelet Derived Growth Factor
FGF: Fibroblast Growth Factor
EGF: epidermal Growth Factor
GH: Growth hormone
TRE: TPA Response Element
SRE: serum response element
CRE: cAMP response element
AcN: acetonitril;
Boc: tert-butoxycarbonyl; 'Bu: tert-butyl;
DCM: dichloromethane;
DMF: dimethylformamide;
Fmoc: 9-fluorenylmethoxycarbonyl;
HMBA: 4-hydroxymethylbenzoic acid;
Q-TOF MS: quadrupole time-of-flight mass spectrometry;
MeIm: N-methyl imidazole;
MSNT: 1-(mesitylene-2-sulphonyl)-3-nitro-1H-1,2,4-triazole;
NEM: N-ethyl morpholine;
PEGA: polyethylene glycol-polydimethyl acrylamide resin;
Pfp: pentafluorophenyl;
Pmc: 2,2,5,7,8-pentamethylchroman-6-sulfonyl;
RP-HPLC: reversed phase high pressure liquid chromatography;
SPPS: solid phase peptide synthesis;
TBTU: O-(benzotriazol-1-yl-N,N,N',N'-tetramethyluronium tetrafluoroborate;
TCOB: Two-compound-one-bead
TFA: trifluoro acetic acid;
Trt: Trityl.

The invention claimed is:

1. A method of identifying a compound modifying in the range of 1 to 5 cellular responses, wherein each cellular response is linked to a reporter system generating a detectable output, wherein if there is more than one cellular response, then each reporter system is different, and wherein the cellular response is selected from the group consisting of:
   i. change in morphology;
   ii. change in viability;
   said method comprising the steps of:
      (a) Providing multiple solid supports capable of supporting adherence and growth of human primary cells, wherein the solid supports are compartmentalized mini-reaction vessels and wherein each compartmentalized mini-reaction vessel is linked to multiple copies of a member of a library of test compounds via cleavable linkers and wherein at least two solid supports comprise different library members; and
      (b) Attaching human primary cells endogenously comprising said reporter system(s) onto said solid support, and
      (c) Releasing a proportion of said library member from the solid support; and
      (d) Screening said solid supports for solid supports comprising cells meeting at least one predetermined selection criterion, wherein said selection criterion is linked directly or indirectly to said detectable output; and
      (e) Selecting solid supports comprising cells meeting said at least one selection criterion; and
      (f) Identifying said library member, thereby identifying a compound modifying in the range of 1 to 5 cellular response.

2. The method according to claim 1, wherein said cellular response is a change in viability.

3. The method according to claim 1, wherein said cellular response is change in morphology.

4. The method according to claim 1, wherein said cells are primary cells from neoplastic tissues.

5. The method according to claim 1, wherein the library is selected from the group consisting of peptides, glycopeptides, lipopeptides, nucleic acids (DNA or RNA), oligosaccharides; chemically modified peptides, oligomers of amino acids glycopeptides, and small organic molecules.

6. The method according to claim 1, wherein at least one cleavable linker is selected from the group consisting of acid-labile, base-labile, fluoride-labile and photo-labile linkers.

7. The method according to claim 1, wherein step c) comprises releasing in the range of 5 to 95% of the copies of the library members.

* * * * *

SEQUENCE LISTING

<160> NUMBER OF SEQ ID NOS: 81

<210> SEQ ID NO 1
<211> LENGTH: 7

```
<212> TYPE: PRT
<213> ORGANISM: Artificial Sequence
<220> FEATURE:
<223> OTHER INFORMATION: Randomly synthesized cell adhesion peptide

<400> SEQUENCE: 1

Ala Arg Ile Arg Ile Gln His
1               5

<210> SEQ ID NO 2
<211> LENGTH: 7
<212> TYPE: PRT
<213> ORGANISM: Artificial Sequence
<220> FEATURE:
<223> OTHER INFORMATION: Randomly synthesized cell adhesion peptide

<400> SEQUENCE: 2

Ala Lys Cys Arg Trp Cys Met
1               5

<210> SEQ ID NO 3
<211> LENGTH: 7
<212> TYPE: PRT
<213> ORGANISM: Artificial Sequence
<220> FEATURE:
<223> OTHER INFORMATION: Randomly synthesized cell adhesion peptide

<400> SEQUENCE: 3

Ala Lys Ala Arg Cys Lys Ser
1               5

<210> SEQ ID NO 4
<211> LENGTH: 7
<212> TYPE: PRT
<213> ORGANISM: Artificial Sequence
<220> FEATURE:
<223> OTHER INFORMATION: Randomly synthesized cell adhesion peptide

<400> SEQUENCE: 4

Ala Lys Tyr Trp Ser Tyr Lys
1               5

<210> SEQ ID NO 5
<211> LENGTH: 7
<212> TYPE: PRT
<213> ORGANISM: Artificial Sequence
<220> FEATURE:
<223> OTHER INFORMATION: Randomly synthesized cell adhesion peptide

<400> SEQUENCE: 5

Ala Tyr Tyr Cys Gln Gln Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Randomly synthesized cell adhesion peptide

<400> SEQUENCE: 6

Ala Arg Arg Cys Phe Arg Asp
1               5

<210> SEQ ID NO 7
<211> LENGTH: 7
<212> TYPE: PRT
```

```
<213> ORGANISM: Artificial Sequence
<220> FEATURE:
<223> OTHER INFORMATION: Randomly synthesized cell adhesion peptide

<400> SEQUENCE: 7

Ala Ala Arg His Cys Tyr Tyr
1               5

<210> SEQ ID NO 8
<211> LENGTH: 7
<212> TYPE: PRT
<213> ORGANISM: Artificial Sequence
<220> FEATURE:
<223> OTHER INFORMATION: Randomly synthesized cell adhesion peptide

<400> SEQUENCE: 8

Ala Tyr Tyr Cys Gln Gln Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Randomly synthesized cell adhesion peptide

<400> SEQUENCE: 9

Ala Asp Leu Lys Arg Pro Met
1               5

<210> SEQ ID NO 10
<211> LENGTH: 7
<212> TYPE: PRT
<213> ORGANISM: Artificial Sequence
<220> FEATURE:
<223> OTHER INFORMATION: Randomly synthesized cell adhesion peptide

<400> SEQUENCE: 10

Ala Gly Gly Lys Arg Lys Phe
1               5

<210> SEQ ID NO 11
<211> LENGTH: 7
<212> TYPE: PRT
<213> ORGANISM: Artificial Sequence
<220> FEATURE:
<223> OTHER INFORMATION: Randomly synthesized cell adhesion peptide

<400> SEQUENCE: 11

Ala Pro Arg Lys Arg Cys Gly
1               5

<210> SEQ ID NO 12
<211> LENGTH: 7
<212> TYPE: PRT
<213> ORGANISM: Artificial Sequence
<220> FEATURE:
<223> OTHER INFORMATION: Randomly synthesized cell adhesion peptide

<400> SEQUENCE: 12

Ala Thr Arg Arg Val Ala Arg
1               5

<210> SEQ ID NO 13
<211> LENGTH: 7
<212> TYPE: PRT
<213> ORGANISM: Artificial Sequence
```

```
<220> FEATURE:
<223> OTHER INFORMATION: Randomly synthesized cell adhesion peptide

<400> SEQUENCE: 13

Ala Gly Lys Lys Asn Lys Asn
1               5

<210> SEQ ID NO 14
<211> LENGTH: 7
<212> TYPE: PRT
<213> ORGANISM: Artificial Sequence
<220> FEATURE:
<223> OTHER INFORMATION: Randomly synthesized cell adhesion peptide

<400> SEQUENCE: 14

Ala Ala Lys Arg Trp Lys Phe
1               5

<210> SEQ ID NO 15
<211> LENGTH: 7
<212> TYPE: PRT
<213> ORGANISM: Artificial Sequence
<220> FEATURE:
<223> OTHER INFORMATION: Randomly synthesized cell adhesion peptide

<400> SEQUENCE: 15

Ala Arg Trp Pro Tyr Arg Gly
1               5

<210> SEQ ID NO 16
<211> LENGTH: 7
<212> TYPE: PRT
<213> ORGANISM: Artificial Sequence
<220> FEATURE:
<223> OTHER INFORMATION: Randomly synthesized cell adhesion peptide

<400> SEQUENCE: 16

Ala Leu Tyr Trp Thr Trp Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Randomly synthesized cell adhesion peptide

<400> SEQUENCE: 17

Ala Ala Tyr Arg Trp Tyr Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Randomly synthesized cell adhesion peptide

<400> SEQUENCE: 18

Ala Arg Cys Ile Arg Gly Asp
1               5

<210> SEQ ID NO 19
<211> LENGTH: 7
<212> TYPE: PRT
<213> ORGANISM: Artificial Sequence
<220> FEATURE:
```

<223> OTHER INFORMATION: Randomly synthesized cell adhesion peptide

<400> SEQUENCE: 19

Ala Thr Lys Cys Lys Gly Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Randomly synthesized cell adhesion peptide

<400> SEQUENCE: 20

Ala Val Tyr Met Arg Asn Ile
1               5

<210> SEQ ID NO 21
<211> LENGTH: 7
<212> TYPE: PRT
<213> ORGANISM: Artificial Sequence
<220> FEATURE:
<223> OTHER INFORMATION: Randomly synthesized cell adhesion peptide

<400> SEQUENCE: 21

Ala Arg Lys Arg Ile Arg Gln
1               5

<210> SEQ ID NO 22
<211> LENGTH: 7
<212> TYPE: PRT
<213> ORGANISM: Artificial Sequence
<220> FEATURE:
<223> OTHER INFORMATION: Randomly synthesized cell adhesion peptide

<400> SEQUENCE: 22

Ala Lys Ile Arg Glu Lys Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Randomly synthesized cell adhesion peptide

<400> SEQUENCE: 23

Ala Arg Arg Phe Lys Met Tyr
1               5

<210> SEQ ID NO 24
<211> LENGTH: 4
<212> TYPE: PRT
<213> ORGANISM: Artificial Sequence
<220> FEATURE:
<223> OTHER INFORMATION: Randomly synthesized cell adhesion peptide

<400> SEQUENCE: 24

Arg Arg Phe Lys
1

<210> SEQ ID NO 25
<211> LENGTH: 4
<212> TYPE: PRT
<213> ORGANISM: Artificial Sequence
<220> FEATURE:
<223> OTHER INFORMATION: Randomly synthesized cell adhesion peptide

```
<400> SEQUENCE: 25

Arg Arg Ile Arg
1

<210> SEQ ID NO 26
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 26

Leu Arg His Arg Leu Lys
1               5

<210> SEQ ID NO 27
<211> LENGTH: 5
<212> TYPE: PRT
<213> ORGANISM: Artificial Sequence
<220> FEATURE:
<223> OTHER INFORMATION: Randomly synthesized cell adhesion peptide

<400> SEQUENCE: 27

Lys Phe Gly Gln Lys
1               5

<210> SEQ ID NO 28
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 28

Lys Val Tyr Met His Lys
1               5

<210> SEQ ID NO 29
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 29

Ile Arg Tyr Arg Leu Arg
1               5

<210> SEQ ID NO 30
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 30

Ala Gln Arg Pro Arg Trp
1               5

<210> SEQ ID NO 31
<211> LENGTH: 6
<212> TYPE: PRT
<213> ORGANISM: Artificial Sequence
<220> FEATURE:
<223> OTHER INFORMATION: Randomly synthesized cell adhesion peptide
```

```
<400> SEQUENCE: 31

Trp Tyr Ala Lys Arg Arg
1               5

<210> SEQ ID NO 32
<211> LENGTH: 8
<212> TYPE: PRT
<213> ORGANISM: Artificial Sequence
<220> FEATURE:
<223> OTHER INFORMATION: Randomly synthesized cell adhesion peptide

<400> SEQUENCE: 32

Lys Arg Ile Arg Gln Arg Leu Arg
1               5

<210> SEQ ID NO 33
<211> LENGTH: 7
<212> TYPE: PRT
<213> ORGANISM: Artificial Sequence
<220> FEATURE:
<223> OTHER INFORMATION: Randomly synthesized cell adhesion peptide

<400> SEQUENCE: 33

Lys Arg Ile Arg Gln Arg Lys
1               5

<210> SEQ ID NO 34
<211> LENGTH: 5
<212> TYPE: PRT
<213> ORGANISM: Artificial Sequence
<220> FEATURE:
<223> OTHER INFORMATION: Randomly synthesized cell adhesion peptide

<400> SEQUENCE: 34

Arg Ile Arg Gln Arg
1               5

<210> SEQ ID NO 35
<211> LENGTH: 5
<212> TYPE: PRT
<213> ORGANISM: Artificial Sequence
<220> FEATURE:
<223> OTHER INFORMATION: Randomly synthesized cell adhesion peptide

<400> SEQUENCE: 35

Arg Gln Arg Ile Arg
1               5

<210> SEQ ID NO 36
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 36

Lys Phe Gly Gln Lys Cys
1               5

<210> SEQ ID NO 37
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 37
```

```
Arg Arg Leu Leu Pro Ile
1               5

<210> SEQ ID NO 38
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 38

Pro Phe Arg Lys Lys Cys
1               5

<210> SEQ ID NO 39
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 39

Tyr Arg Trp Arg Ile Ala
1               5

<210> SEQ ID NO 40
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 40

Arg Ser Lys Arg Ile Asn
1               5

<210> SEQ ID NO 41
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 41

Arg Ser Ala Lys Arg Cys
1               5

<210> SEQ ID NO 42
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 42

Lys Lys Gln Phe Trp Phe
1               5

<210> SEQ ID NO 43
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 43
```

```
Arg Met Lys Leu His Lys
1               5

<210> SEQ ID NO 44
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 44

Arg His Trp Gly Arg Ile
1               5

<210> SEQ ID NO 45
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 45

Thr Lys Arg Leu Lys Thr
1               5

<210> SEQ ID NO 46
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 46

Thr Lys Gly Lys Ala Lys
1               5

<210> SEQ ID NO 47
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 47

Ala Lys Thr Arg His Arg
1               5

<210> SEQ ID NO 48
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 48

Asn Arg Pro Arg Val Arg
1               5

<210> SEQ ID NO 49
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 49

Val Pro Arg Lys Val Gln
```

```
<210> SEQ ID NO 50
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 50

Lys Met Arg Tyr Cys Gln
1               5

<210> SEQ ID NO 51
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 51

Ile Arg Lys His Leu Ile
1               5

<210> SEQ ID NO 52
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 52

Pro Arg Arg Val Val Ile
1               5

<210> SEQ ID NO 53
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 53

Lys Arg Glu Ser Lys Arg
1               5

<210> SEQ ID NO 54
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 54

Ser Arg Lys Asp Arg Lys
1               5

<210> SEQ ID NO 55
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 55

Arg Cys Lys Lys Leu Ile
1               5
```

```
<210> SEQ ID NO 56
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 56

Arg Lys Leu Arg Val Asn
1               5

<210> SEQ ID NO 57
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 57

Val Arg Thr Val Arg Val
1               5

<210> SEQ ID NO 58
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 58

Arg Ala Phe Lys Tyr Tyr
1               5

<210> SEQ ID NO 59
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 59

Ile Thr Arg Arg Thr Gln
1               5

<210> SEQ ID NO 60
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 60

Lys Met Pro Lys Lys Asn
1               5

<210> SEQ ID NO 61
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 61

Lys Pro Lys Met Met Cys
1               5
```

<210> SEQ ID NO 62
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 62

Lys Lys Met Arg Phe Trp
1               5

<210> SEQ ID NO 63
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 63

Lys Lys Lys Phe Tyr Tyr
1               5

<210> SEQ ID NO 64
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 64

Lys Ser Asn Lys Val Arg
1               5

<210> SEQ ID NO 65
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 65

Lys Trp Pro His His Arg
1               5

<210> SEQ ID NO 66
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 66

Arg His Ile Gln Trp Tyr
1               5

<210> SEQ ID NO 67
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 67

Leu Arg Leu Lys Pro Lys
1               5

```
<210> SEQ ID NO 68
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 68

Glu Arg Lys Arg Cys Thr
1               5

<210> SEQ ID NO 69
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 69

Arg Arg Ala Arg Gln Asp
1               5

<210> SEQ ID NO 70
<211> LENGTH: 6
<212> TYPE: PRT
<213> ORGANISM: Artificial Sequence
<220> FEATURE:
<223> OTHER INFORMATION: Randomly synthesized cell adhesion peptide

<400> SEQUENCE: 70

Arg Glu Lys Gly Ala Arg
1               5

<210> SEQ ID NO 71
<211> LENGTH: 25
<212> TYPE: DNA
<213> ORGANISM: Artificial Sequence
<220> FEATURE:
<223> OTHER INFORMATION: Primer

<400> SEQUENCE: 71
ccagtgttcc ctccatggga cctaa                                         25

<210> SEQ ID NO 72
<211> LENGTH: 21
<212> TYPE: DNA
<213> ORGANISM: Artificial Sequence
<220> FEATURE:
<223> OTHER INFORMATION: Primer

<400> SEQUENCE: 72
taagccatcc cccacgccaa g                                             21

<210> SEQ ID NO 73
<211> LENGTH: 29
<212> TYPE: DNA
<213> ORGANISM: Artificial Sequence
<220> FEATURE:
<223> OTHER INFORMATION: Primer

<400> SEQUENCE: 73
gataagcttc cagtgttccc tccatggga                                     29

<210> SEQ ID NO 74
<211> LENGTH: 26
<212> TYPE: DNA
<213> ORGANISM: Artificial Sequence
```

```
<220> FEATURE:
<223> OTHER INFORMATION: Primer

<400> SEQUENCE: 74
tatggatcca aggtgcgcac gcggct                                           26

<210> SEQ ID NO 75
<211> LENGTH: 29
<212> TYPE: DNA
<213> ORGANISM: Artificial Sequence
<220> FEATURE:
<223> OTHER INFORMATION: Primer

<400> SEQUENCE: 75
gagaattctc ctaaagacag tgccaagtg                                        29

<210> SEQ ID NO 76
<211> LENGTH: 30
<212> TYPE: DNA
<213> ORGANISM: Artificial Sequence
<220> FEATURE:
<223> OTHER INFORMATION: Primer

<400> SEQUENCE: 76
catggtacca tgacagagga ggaagaggag                                       30

<210> SEQ ID NO 77
<211> LENGTH: 26
<212> TYPE: DNA
<213> ORGANISM: Artificial Sequence
<220> FEATURE:
<223> OTHER INFORMATION: Primer

<400> SEQUENCE: 77
gctggatccg ggtcccagga gcccag                                           26

<210> SEQ ID NO 78
<211> LENGTH: 21
<212> TYPE: DNA
<213> ORGANISM: Artificial Sequence
<220> FEATURE:
<223> OTHER INFORMATION: Primer

<400> SEQUENCE: 78
gcgctgcaca atggcggctc t                                                21

<210> SEQ ID NO 79
<211> LENGTH: 25
<212> TYPE: DNA
<213> ORGANISM: Artificial Sequence
<220> FEATURE:
<223> OTHER INFORMATION: Primer

<400> SEQUENCE: 79
gcactcacag ctcacaaagg cgtct                                            25

<210> SEQ ID NO 80
<211> LENGTH: 29
<212> TYPE: DNA
<213> ORGANISM: Artificial Sequence
<220> FEATURE:
<223> OTHER INFORMATION: Primer

<400> SEQUENCE: 80
gatggtaccc gctgcacaat ggcggctct                                        29
```

```
<210> SEQ ID NO 81
<211> LENGTH: 24
<212> TYPE: DNA
<213> ORGANISM: Artificial Sequence
<220> FEATURE:
<223> OTHER INFORMATION: Primer

<400> SEQUENCE: 81
ggatcctcac gcaggtaggc ctcc                                              24
```